(12) United States Patent
Ayyub et al.

(10) Patent No.: US 10,392,646 B2
(45) Date of Patent: Aug. 27, 2019

(54) DEVICE AND METHODS OF USING DEVICE FOR DETECTION OF AMINOACIDOPATHIES

(71) Applicants: UNIVERSITY OF MARYLAND, OFFICE OF TECHNOLOGY COMMERCIALIZATION, College Park, MD (US); CHILDREN'S NATIONAL MEDICAL CENTER, Washington, DC (US); THE UNITED STATES OF AMERICA, as represented by the Secretary, Department of Health and Human, Washington, DC (US)

(72) Inventors: Omar Bilal Ayyub, Potomac, MD (US); Adam Michael Behrens, Olney, MD (US); Peter Kofinas, Bethesda, MD (US); Marshall Lynn Summar, Washington, DC (US); Juan Manuel Cabrera-Luque, Rockville, MD (US); Gary Cunningham, Washington, DC (US); Anton Simeonov, Bethesda, MD (US); Juan Marugan, Gaithersburg, MD (US)

(73) Assignees: University of Maryland, College Park, College Park, MD (US); Children's National Medical Center, Washington, DC (US); The United States of America, as Represented by The Secretary, Department of Health and Human Services, Bathesda, MD (US)

( * ) Notice: Subject to any disclaimer, the term of this patent is extended or adjusted under 35 U.S.C. 154(b) by 376 days.

(21) Appl. No.: 14/436,844
(22) PCT Filed: Oct. 17, 2013
(86) PCT No.: PCT/US2013/065548
§ 371 (c)(1),
(2) Date: Apr. 17, 2015
(87) PCT Pub. No.: WO2014/062985
PCT Pub. Date: Apr. 24, 2014

(65) Prior Publication Data
US 2016/0168613 A1    Jun. 16, 2016

Related U.S. Application Data

(60) Provisional application No. 61/714,870, filed on Oct. 17, 2012, provisional application No. 61/776,371, filed on Mar. 11, 2013.

(51) Int. Cl.
| | |
|---|---|
| *G01N 33/68* | (2006.01) |
| *C12N 9/02* | (2006.01) |
| *C12N 9/06* | (2006.01) |
| *C12Q 1/00* | (2006.01) |
| *C12N 11/04* | (2006.01) |
| *C12N 11/10* | (2006.01) |
| *G01N 27/327* | (2006.01) |

(52) U.S. Cl.
CPC .......... *C12Q 1/005* (2013.01); *C12N 9/0018* (2013.01); *C12N 9/0071* (2013.01); *C12N 11/04* (2013.01); *C12N 11/10* (2013.01); *G01N 27/3277* (2013.01); *G01N 33/6812* (2013.01); *G01N 2800/04* (2013.01); *G01N 2800/52* (2013.01)

(58) Field of Classification Search
CPC ...... C12N 11/04; C12N 11/10; C12N 9/0018; C12N 9/0071; C12Q 1/005; G01N 27/3277; G01N 2800/52; G01N 33/68121; G01N 2800/04; G01N 33/6812
See application file for complete search history.

(56) References Cited

U.S. PATENT DOCUMENTS

| | | |
|---|---|---|
| 4,254,222 A | 3/1981 | Owen |
| 4,351,899 A | 9/1982 | Owen |
| 4,806,343 A | 2/1989 | Carpenter et al. |
| 4,849,345 A | 7/1989 | Asano et al. |
| 4,963,814 A | 10/1990 | Parks et al. |
| 4,966,856 A | 10/1990 | Ito et al. |
| 4,999,582 A | 3/1991 | Parks et al. |
| 4,999,632 A | 3/1991 | Parks |
| 5,243,516 A | 9/1993 | White |
| 5,326,697 A | 7/1994 | Magers |
| 5,353,351 A | 10/1994 | Bartoli et al. |
| 5,366,609 A | 11/1994 | White et al. |
| 5,405,511 A | 4/1995 | White et al. |
| 5,438,271 A | 8/1995 | White et al. |

(Continued)

FOREIGN PATENT DOCUMENTS

| | | |
|---|---|---|
| EP | 1314786 A1 | 5/2003 |
| JP | 2003-065951 | 3/2003 |

(Continued)

OTHER PUBLICATIONS

"Alginic Acid", Wikipedia, <https://en.wikipedia.org/w/index.php?title=Alginic_acid&oldid=507468262>, archived online Aug. 15, 2012, 3 pages (Year: 2012).*

(Continued)

*Primary Examiner* — Aaron J Kosar
(74) *Attorney, Agent, or Firm* — Ballard Spahr LLP; John A. Zurawski

(57) ABSTRACT

The present invention relates to a biosensor capable of measuring the total concentration of one or a plurality of amino acids with the use of a reagentless system comprising an electrode modified by hydrogel that comprises at least one enzyme that oxidizes at least one substrate that is at least one amino acid. In some embodiments, the biosensor comprises a hydrogel comprising alginate. In some embodiments, the biosensor comprises use of a thermophilic bacterial metabolic enzyme immobilized or attached to the hydrogel.

19 Claims, 23 Drawing Sheets
Specification includes a Sequence Listing.

(56) References Cited

U.S. PATENT DOCUMENTS

| | | | |
|---|---|---|---|
| 5,510,245 | A | 4/1996 | Magers |
| 5,670,031 | A | 9/1997 | Hintsche et al. |
| 5,762,770 | A | 6/1998 | Pritchard et al. |
| 5,912,139 | A | 6/1999 | Iwata et al. |
| 6,541,216 | B1 | 4/2003 | Wilsey et al. |
| 6,645,359 | B1 | 11/2003 | Bhullar et al. |
| 6,662,439 | B1 | 12/2003 | Bhullar |
| 6,736,957 | B1 | 5/2004 | Forrow et al. |
| 7,381,538 | B2 * | 6/2008 | Reardon ............... C12Q 1/002 435/23 |
| 7,914,460 | B2 * | 3/2011 | Melker ............... A61B 5/083 600/365 |
| 2001/0053849 | A1 | 12/2001 | Kreek et al. |
| 2002/0127623 | A1 | 9/2002 | Minshull et al. |
| 2003/0176183 | A1 | 9/2003 | Drucker et al. |
| 2006/0223729 | A1 | 10/2006 | Hamblin et al. |
| 2007/0077567 | A1 | 4/2007 | Kim et al. |
| 2007/0122867 | A1 | 5/2007 | Shunnarah et al. |
| 2008/0045825 | A1 | 2/2008 | Melker et al. |
| 2008/0242738 | A1 | 10/2008 | Marks et al. |
| 2012/0129710 | A1 | 5/2012 | McCafferty et al. |
| 2012/0164627 | A1 | 6/2012 | Battrell et al. |
| 2012/0231489 | A1 | 9/2012 | Lenhert |
| 2013/0201049 | A1 | 8/2013 | Sugimoto |

FOREIGN PATENT DOCUMENTS

| | | |
|---|---|---|
| JP | 2006-271379 | 10/2006 |
| WO | 03/025627 A2 | 3/2003 |
| WO | WO 2004091376 A2 | 10/2004 |

OTHER PUBLICATIONS

IUBMB "[EC 1.4.1] Oxidoreductases: with NAD or NADP as Acceptor" IUBMB Enzyme Nomenclature, <http://www.sbcs.gmul.ac.uk/iubmb/enzyme/EC1/4/1/>, ECs established/archived 1961-1989, retrieved online Jan. 22, 2018, 1 page. (Year: 2018).*

Pasco N, et al "Characterisation of a thermophilic L-glutamate dehydrogenase biosensor for amperometric determination of L-glutamate by flow injection analysis" Biosensors & Bioelectronics 14 (1999) 171-178. (Year: 1999).*

Lobo MJ, et al "Amperometric Biosensors Based on NAD(P)-Dependent Dehydrogenase Enzymes" Electroanalysis, 1997, 9(3), pp. 191-202. (Year: 1997).*

Rocha-Martin J, et al "New Biotechnological Perspectives of a NADH Oxidase Variant from Thermus thermophilus HB27 as NAD+-recycling Enzyme" BMC Biotechnology, 2011, 11:101, 11 pages. (Year: 2011).*

Cock LS, et al, "" Chilean Journal of Agricultural Research, Apr.-Jun. 2009, 69(2), pp. 270-280. (Year: 2009).*

Azmi et al., Biosensor based on glutamate dehydrogenase immobilized in chitosan for the determination of ammonium in water samples, Analytical Biochem 2009 388(1):28-32.

Cui et al., Development of an interference-free biosensor for l-glutamate using a bienzyme salicylate hydroxylase/l-glutamate dehydrogenase system, Enzyme and Microbial Tech 2007 41(6-7):689-693.

Huang et al., Determination of L-phenylalanine based on an NADH-detecting biosensor, Analytical Chem 1998 70:991-997.

Ionescue et al., Improved enzyme retention from an electroploymerized polypyrrole-alginate matrix in the development of biosensors, Electrochem Comm 2005 7(12):1277-1282.

Kwan et al., Amperometric determination of ammonium with bienzyme/poly(carbamoyl) sultanate hydrogel-based biosensor, Sensors and Actuators B 2005 107:616-622.

Qin et al., Amperometric enzyme electrodes of glucose and lactate based on poly(diallyldimethylammonium)-alginate-metal ion-enzyme biocomposites, Analytica Chimica Acta 2012 720:49-56.

Villalonga et al., Supramolecular-mediated immobilization of L-phenylalanine dehydrogenase on cyclodextrin-coated Au electrodes for biosensor application, Biotech Lett 2007 29(3):447-452.

Weiss et al., Dehydrogenase based reagentless biosensor for monitoring phenylketonuria, Biosens Bioelectron 2007 22(11):2436-41.

Uniprot FBCXT3, Geobacillus themoglucosidasius C56-YS93 phenylalanine dehydrogenase [online] May 16, 2012 [retrieved Dec. 27, 2013] http://www.uniprot.org/uniprot/F8CXT3.txt?version=9.

Forrow et al., Development of a commercial amperometric biosensor electrode for the ketone D-3-hydroxybutyrate, Biosens Bioelectron 2005 20(8):1617-25.

Hay, I.D. et al., Microbial Alginate Production, Modification and Its Applications. Microbial Biotechnol. 2013; 6:637-50.

"Microcomputer." Britannica Academic, Encyclopeadia Britannica. 2016; [Retrieved on Sep. 2, 2018] [Retrieved from the Internet—URL: <http://academic.eb.com/levels/collegiate/article/microcomputer/52500>. 2016 (1 page).

Yetisen, A.K., et al., Paper-based microfluidic point-of-care diagnostic devices, Lab Chip, 2013, 13, 2210.

* cited by examiner

DEVICE AND METHODS OF USING DEVICE FOR DETECTION OF AMINOACIDOPATHIES

CROSS-REFERENCE TO RELATED APPLICATIONS

This application claims priority to and is a United States National Stage filing under 35 U.S.C. § 371 of International PCT Application Serial No. PCT/US2013/065548, filed Oct. 17, 2013, which claims priority to U.S. Provisional Ser. No. 61/714,870, filed Oct. 17, 2012, and U.S. Provisional Ser. No. 61/776,371, filed Mar. 11, 2013, each of which is incorporated herein by reference in its entirety.

GOVERNMENT SUPPORT

This invention was made jointly with support form the United States government as represented by the Secretary of Health and Human Services and the National Institutes of Health (NIH) under NIH grant number # HHSN268201200360P. The United States government has certain rights in the invention.

FIELD OF THE INVENTION

The invention relates generally to devices that quantify and identify the presence or absence of amino acids in a sample of bodily fluid. In some embodiments, the invention relates to diagnosing a subject with an aminoacidopathy by detecting the presence, absence, or quantity of amino acids in a sample of bodily fluid. In some embodiments, the device is a reagentless biosensor only requiring a sample of bodily fluid for detection and/or quantification of one or more amino acids.

BACKGROUND OF THE INVENTION

Numerous metabolic disorders, such as hyperammonemia and aminoacidopathies, are characterized by a chronic elevation of a specific metabolite due to dysfunction of enzymes involved in metabolic regulation, process and clearance. These high levels of metabolites can be biochemically evaluated by measuring plasma levels using well defined analytical methods and result in specific tissue toxicity, which define the symptomatology of each disease. It would be of great utility and convenience to develop sensors able to detect specific plasma metabolites in real-time in similar fashion of what, for example, has been done with glucose and diabetes. Point of care sensors would allow doing immediate blood level evaluation of specific metabolites, facilitating the management, treatment and follow up of metabolic disorders. Recent estimations of the prevalence of metabolic and endocrine disorders in USA reveal that at least 5% of the population suffers from an endocrine disorder and more than 47 million of US residents have a metabolic syndrome. Besides the tremendous human suffering and the high impact on the health care costs, the management of these diseases is difficult and expensive not only in terms of medications, analytical monitoring, and follow-up of patients, but in many cases results in unnecessary procedures and hospitalizations. Although important advances have been made in specific disorders such as diabetes or hypercholesterolemia, advances in others with lower prevalence have been delayed. For example, not much advance has been made in obtaining new diagnostic or therapeutic solutions for patients with Hyperammonemia and Aminoacidopathies. Currently the monitoring of metabolite levels has to be done in a hospital equipped with a specialized mass spectrometry instrumentation, and therefore every time that these patients have an appearance of a crisis, whether related or unrelated to the elevation of the corresponding metabolite, they need to visit the hospital in order for the specialized testing to be performed. It would thus be extremely advantageous, from both a patient quality-of-life and a financial management standpoint, to develop devices capable of detecting and quantifying these metabolites in real time.

SUMMARY OF INVENTION

The present invention encompasses the recognition that aminoacidopathies can be identified and/or characterized by identifying the levels or quantities of amino acids in bodily fluid including human and non-human blood samples. In some embodiments, the present invention relates to identifying the quantity, presence, or absence of amino acids in bodily fluids by contacting a bodily fluid to a device disclosed herein. In some embodiments, the methods disclosed herein do not comprise contacting the bodily fluid with any reagent or external stimuli prior to identifying or quantifying whether or how much one or more amino acids are present in the bodily fluid.

The present invention relates to a biosensor capable of measuring the total concentration of one or a plurality of amino acids in a sample with the use of a reagentless system comprising an electrode modified by hydrogel that comprises at least one enzyme that oxidizes at least one substrate that is at least one amino acid. The invention provides an amino acid biosensor for measuring the total concentration of one or multiple specified amino acids, comprising at least a first electrically conductive surface (for measuring) and at least a second electrically conductive surface (counter electrode), wherein the first electrically conductive surface having, as constituent factors, mediators as well as enzymes selectively utilizing the multiple specified amino acids as substrates, wherein the one or plurality of enzymes have respective substrate affinities with the one or plurality of specified amino acids. The one or plurality of enzymes produce reaction products by reactions with the specified amino acids as substrates, wherein the mediators transport electrons between the reaction products and the measuring electrode at the measuring of amino acid concentrations, and wherein applied voltages at measuring between the first and second electrically conductive surfaces include such an applied voltage that, on a working curve representing the relationship between current value and applied voltage with respect to each of the one or plurality of specified amino acids, the distribution of current value at unchanged applied voltage as to individual amino acids.

We envisioned the achievement of this goal immobilizing specific enzymes within a polymer attached to an electrode able to measure the electron flow produced by the redox transformation of the metabolite being analyzed. The concentration of the metabolite in blood linearly correlates with the electron flow or current measurements on the circuit that comprise the at least one electrically conductive surfaces. The invention relates to the reduction to practice of this concept, showing how to select the metabolite, how to choose the immobilized enzyme, how to do the immobilization (what polymer, what additives, etc), how to attach the components to the electrode, how to make a measurement and how do develop a prototype. This invention is used to measure metabolites in blood of patients in real time. Aside from the sensor disclosed herein, there are no known sensors able to measure the proposed metabolites in real time.

The invention relates to a device comprising at least one electrically conductive surface (such as an electrode) operably connected to a voltmeter and/or amperometer, the electrode comprising components that, when combined and in the presence of an amino acid, causes a electrochemical reaction to take place that releases at least one or a series of electrons. In some embodiments, the device comprises at least a first and second electrically conductive surface, wherein the first electrically conductive surface comprises a hydrogel comprising an enzyme disclosed herein and the second electrically conductive surface does not comprise a hydrogel or an enzyme; wherein the voltmeter and/or amperometer are configured in a circuit such that the voltmeter can detect a voltage differential between the first and second electrodes in the presence of an amino acid and/or wherein the amperometer can detect an increased current in the first electrode as compared to the second electrode. The at least one or a series of electrons are released after one or more enzymes within the hydrogel catalyzes the oxidation of the amino acid in a bodily sample in the presence of the one or more amino acids.

Hydrogel formulations are used to entrap one or more enzymes (that utilizes the metabolite/analyte as a specific substrate for its reaction) along with, in some embodiments, a requisite cofactor in close proximity to the at least first electrode surface, with the hydrogel providing a simultaneous exclusion of interfering ions and macromolecules (contained within the patient's blood sample) from the electrode sensor. The coated electrode is contained within a electrochemical detection device capable of converting redox equivalents generated by the enzyme reaction into electron flow which in turn is measured as a current or voltage differential. Analyte concentration is derived using a calibration curve that correlates amperage or voltage differential to concentration of amino acid in the sample of bodily fluid. In one embodiment, a small volume of whole blood is applied to the electrode and the result is reported within minutes of the application or contact to the electrode. Depending on the exact analyte, specific enzyme(s) and cofactor(s) are incorporated into the electrode in order to achieve analyte-specific reaction and response. For example, to detect elevated phenylalanine, the enzyme phenylalanine dehydrogenase is immobilized to the at least one electrically conductive surface optionally contained within a hydrogel.

The invention provides a method of sorting a mixture of samples of bodily fluid comprising: contacting a plurality of blood samples to a device or system disclosed herein. In some embodiments, the method of sorting or cataloguing a mixture of samples of bodily fluid further comprises the step of determining one or more concentrations of amino acid in a bodily fluid sample based upon a current value or voltage differential value measured by the device. In some embodiments, the method further comprises the step of comparing the one or more concentration of amino acids in the sample of bodily fluid with one or more concentrations of amino acids in sample of bodily fluid obtained from subject who does not have or is not suspected of having one or more aminoacidopathies, and cataloging, compiling, or identifying whether a sample of bodily fluid from a subject has an aminoacidopathy based upon their similarities or differences in concentration value to a sample of bodily fluid from a subject without an aminoacidopathy. The invention provides a method of diagnosing a subject with an aminoacidopathy comprising: contacting at least one sample of bodily fluid from the subject to a device or system disclosed herein. In some embodiments, the method of diagnosing further comprises the step of determining one or more concentrations of amino acid in a bodily fluid sample based upon a current value or voltage differential value measured by the device. In some embodiments, the method further comprises the step of comparing the one or more concentration of amino acids in the one or more samples from the subject with one or more concentrations of amino acids in sample of bodily fluid obtained from subject who does not have or is not suspected of having one or more aminoacidopathies, identifying whether a sample of bodily fluid from a subject has an aminoacidopathy based upon their similarities or differences in concentration value to the sample of bodily fluid from a subject without an aminoacidopathy.

The invention also provides a method of monitoring the concentrations of one or more amino acids in subject over time in a sample of bodily fluid from a subject diagnosed or suspected as having one or more aminoacidopathies, the method comprising: contacting one or more samples of bodily fluid from a subject to a device or system disclosed herein and measuring the concentration of the one or more amino acid in samples of bodily fluid from the subject at one time point and performing a repeating of the measurement at least once at a different time point. In some embodiments, the method of monitoring the concentrations of one or more amino acids in subject over time in a sample of bodily fluid from a subject diagnosed or suspected as having one or more aminoacidopathies further comprises the step of cataloguing the concentration values of the one or more amino acids over time. In some embodiments, the method further comprises the step of comparing the one or more concentration of amino acids from the plurality of samples of bodily fluid from the subject over time and, optionally notifying a subject if the concentration of one or more amino acids reaches or exceeds or drops below a threshold value that requires medical treatment or modification of diet.

In some embodiments, samples of bodily fluid are isolated from a subject having been diagnosed with or suspected as having one or more aminoacidopathies. For example, in some embodiments, a sample of bodily fluid such as a urine sample or a blood sample is isolated from the subject. The sample of bodily fluid is contacted to at least one electrode comprising at least one enzyme disclosed herein and the amino acid concentration in the sample of bodily fluid is measured based upon the magnitude of the voltage differential or current detected by the device comprising the at least one electrode. In further embodiments, method of the present invention comprises contacting a sample of bodily fluid to at least one electrode comprising an immobilized enzyme disclosed herein, measuring the current or voltage difference between the at least one electrode and an electrically conductive surface that does not comprise an immobilized enzyme disclosed herein, determining the concentration of one or more amino acids in the sample of bodily fluid, and optionally, providing a readout of one or more concentration values to a subject from which the sample of bodily fluid was obtained.

In some embodiments, the present disclosure provides methods comprising contacting a sample of bodily fluid from a subject to a first electrode having one or more enzymes immobilized thereon, optionally distributed or immobilized in a gel. In some embodiments, the gel is a hydrogel comprising alginate. In some embodiments, the present disclosure provides methods comprising detecting presence or level amino acids in a sample of bodily fluid between cells in the sample. In some embodiments, provided methods comprise determining that a particular set of detected interactions defines an threshold value that is characteristic of an increased severity of aminoacidopathy in that it distinguishes them from elevated or non-elevated amino acid levels in another sample of bodily fluid from the subject or from a sample of bodily fluid that is a reference or control sample such that, if the threshold value is reached, the device or system disclosed herein provides the subject with a signal or notification that treatment or diet modification should be sought. In some embodiments, the step of detecting comprises detecting presence or level of amino acid concentrations in a sample of bodily fluid that is characteristic of particular severity of disease in the sample in that it distinguishes them from a sample of bodily fluid that is a reference or control sample.

In some embodiments, any of the methods disclosed herein do not comprise pre-treating the sample of bodily fluid prior to contacting the sample with the at least one electrically conductive surface. In some embodiments, any of the methods disclosed herein do not comprise using at step of treating the sample with liquid chromatography and/or electrophoresis before, simultaneously with or after contacting the sample to the at least one electrode. In some embodiments, any of the methods disclosed herein comprise contacting the sample to at least one electrode that does not comprise an enzyme obtained from an organism other than a bacteria or a plant.

In some embodiments, the present disclosure provides a system comprising one or more devices disclosed herein optionally in operable connection to a electronic storage medium that compiles amino acid concentration values of a subject. In some embodiments, the electronic storage medium comprises compiled amino acid concentration values of a subject over time. In some embodiments, the system comprises at least one electrically conductive surface that comprises an enzyme disclosed herein, a mediator, and optionally a gel or hydrogel. In some embodiments, the system comprises an electronic circuit that is in operable connection to the at least one electrodes and a voltmeter and/or amperomter which measures the respective voltage and/or amperage of the circuit across the at least one electrode when the at least one electrode is in the presence of one or more amino acids. In some embodiments, system comprising one or more devices disclosed herein optionally in operable connection to a electronic storage medium that compiles amino acid concentration values of a subject determines one or a plurality of concentration values of amino acids in a sample of bodily fluid when the sample of bodily fluid is in contact with the at least one electrode and under conditions and for a time sufficient for the one or more enzymes disclosed herein to oxidize its amino acid substrate, create a voltage differential or current change in the circuit and the device to display the concentration value on one or more displays.

In some embodiments, the invention provides for a method comprising steps of: contacting a sample comprising cells with an electrode. The invention further provides for a method comprising steps of: contacting a sample comprising bodily fluid under conditions and for a time sufficient for a set of interactions to occur between particular amino acids in the sample and the one or plurality of hydrogel component described herein. The invention relates to a biosensor comprising: at least one electrically conductive support, the electrically conductive support attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support or surface.

In some embodiments, the biosensor comprises at least three electrically conductive supports. In some embodiments, the at least one electrically conductive support is a silver and silver chloride wire. In some embodiments, the at least one electrically conductive support comprises at least one or a combination of metabolic enzymes chosen from: leucine dehydrogenase, tyrosine dehydrogenase, phenylalanine dehydrogenase, leucine oxidoreductase, tyrosine monooxygenase, alanine dehydrogenase, or glutamate dehydrogenase; or functional fragments thereof. In some embodiments, the biosensor comprises at least a first and a second electrically conductive support, wherein the first electrically conductive support is attached to a hydrogel, the hydrogel comprising at least one electron mediator, at least one reduction agent, and at least one metabolic enzyme or functional fragment thereof, wherein said first and second electrically conductive supports being operably connected to said voltmeter and/or amperometer to apply a voltage therebetween.

In some embodiments, the at least one electrically conductive support comprises an electronegative or anionic chemical component. In some embodiments, the at least one hydrogel comprises trehalose. In some embodiments, the biosensor does not comprise one or more of the following: (i) uricase or a functional fragment thereof; (ii) a hydrogel comprising dextran or a derivative thereof; (iii) a bacterial cell; (iv) an electronic dipole configured for electrophoresis; and (v) 3, 4-DHB. In some embodiments, the biosensor is at least 70% biologically active after about sixteen days in storage at 4 degrees Celsius. In some embodiments, the biosensor is at least 70% biologically active after about thirty days in storage at 4 degrees Celsius. In some embodiments, the biosensor is not functionally dependent upon exposure to UV light or addition of any stimulus external to the biosensor. In some embodiments, the at least one enzyme or functional fragment thereof is derived from a bacterial species and is immobilized in the hydrogel. In some embodiments, the at least one enzyme or functional fragment thereof is derived from a thermophilic bacterial species and is immobilized in the hydrogel. In some embodiments, the at least one enzyme or functional fragment thereof comprises at least about 70% sequence identity to SEQ ID NO:1 or SEQ ID NO:2.

In some embodiments, the at least one enzyme is phenyalanine dehydrogenase or a functional fragment thereof obtained from a thermophilic bacterial cell; wherein the hydrogel comprises trehalose, wherein the alginate concentration of the hydrogel is from about 1% to about 3% weight to volume of the total volume attached to the at least one electrically conductive support; and wherein the electrically conductive support comprises a wire comprising silver and silver chloride in operable connection to the voltmeter and/or amperometer.

In some embodiments, the alginate comprises a block polymer with a formula

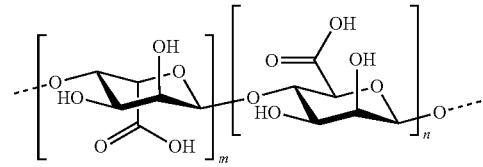

wherein m and n are any positive integer.

In some embodiments, the biosensor the at least one electrically conductive support is not covered by a membrane comprising cellulose or a derivative thereof. In some embodiments, the at least one electron mediator is selected from: thionine, o-phenylenediamine, methylene blue, and toluidine blue. In some embodiments, the at least one reduction agent is chosen from: NAD+ or FAD+.

The invention also relates to a biosensor comprising: at least one electrically conductive support, the electrically conductive support attached to at least one hydrogel, the hydrogel comprising at least one electron mediator, at least one reduction agent, and at least one metabolic enzyme or functional fragment thereof; wherein the at least one enzyme or functional fragment thereof is at least 70% homologous to a phenylalanine dehydrogenase from *Geobacillus thermoglucosidiasus*; and an amperometer and/or voltmeter operably connected to the at least one electrically conductive support. In some embodiments, the enzyme or functional fragment thereof is at least 70%, 80%, 85%, 90%, 95%, 96%, 97%, 98%, 99% homologous to SEQ ID NO:1 or at least 70%, 80%, 85%, 90%, 95%, 96%, 97%, 98%, 99% homologous to a functional fragment of SEQ ID NO:1. In some embodiments, the enzyme or functional fragment thereof is not derived from a species other than a bacterial cell. In some embodiments, the enzyme or functional fragment thereof is at least 70%, 80%, 85%, 90%, 95%, 96%, 97%, 98%, 99% homologous to SEQ ID NO:2 or at least 70%, 80%, 85%, 90%, 95%, 96%, 97%, 98%, 99% homologous to a functional fragment of SEQ ID NO:2.

The invention relates to a system comprising a biosensor comprising: at least one electrically conductive support, the electrically conductive support attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support or surface. The invention also relates to a system comprising a biosensor comprising: at least one electrically conductive support, the electrically conductive support attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support or surface; wherein the biosensor is in operable connection to at least one computer storage memory. In some embodiments, the system further comprises a sample of bodily fluid. In some embodiments, the system further comprises a digital display in operable connection to the at least one electrically conductive support (or surface) by an electrical circuit capable of carrying an a electrical signal corresponding to a measurement of current and/or voltage differential from the voltmeter and/or amperometer to the digital display, wherein the digital display is a configured to display one or more concentration values of an amino acid in a sample over time when the at least one electrically conductive support (or surface) is in contact with the sample for a time period sufficient for the at least one metabolic enzyme to catalyze the oxidation of its amino acid substrate.

In some embodiments, the system further comprises a computer processor in operable connection with the at least one computer storage memory. In some embodiments, the metabolic enzyme is a phenylalanine dehydrogenase immobilized within the hydrogel and wherein the alginate concentration of the hydrogel is from about 1% to about 3% weight to volume of the total volume attached and/or contacted to the at least one electrically conductive support.

The invention also relates to a kit comprising a biosensor comprising a voltmeter and/or amperometer and a display configured in an electrical circuit that, upon contact with at least one removable electrically conductive support, becomes closed such that the voltmeter and/or amperometer are in operable communication with at least one electrically conductive support, the electrically conductive support comprising a hydrogel; wherein the hydrogel comprises at least one electron mediator, at least one reduction agent, at least one metabolic enzyme or functional fragment thereof, and alginate.

In some embodiments, the kit comprises at least one of the following: a plurality of test strips comprising one or a plurality of electrically conductive supports, wherein the one or plurality of electrically conductive supports comprises a hydrogel comprising alginate; a control or reference sample of bodily fluid; a set of data comprising threshold values; and a set of instructions, wherein the set of instructions or the set of data optionally accessible remotely through an electronic medium. In some embodiments, the kit comprises a solid support that comprises at least a first and a second electrode, wherein the first electrode comprises a hydrogel, the hydrogel comprising at least one electron mediator, at least one reduction agent, and at least one metabolic enzyme or functional fragment thereof; and wherein the second electrode is a control or reference electrode. In some embodiments, the kit comprises a test strip comprising a solid support attached to a first and a second electrode described herein.

The invention also relates to a method of determining or identifying a concentration of an amino acid in a sample of bodily fluid comprising: (a) contacting a sample of bodily fluid to: (i) a biosensor comprising at least one electrically conductive support, the electrically conductive support attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support; or (ii) a system comprising a biosensor comprising: at least one electrically conductive support, the electrically conductive support attached to at least one hydrogel, the hydrogel comprising at least one electron mediator, at least one reduction agent, and at least one metabolic enzyme or functional fragment thereof; wherein the at least one enzyme or functional fragment thereof is at least 70% homologous to a phenylalanine dehydrogenase from *Geobacillus thermoglucosidiasus*; and an amperometer and/or voltmeter operably connected to the at least one electrically conductive support; or (iii) a test strip disclosed herein; or (b) determining a quantity of amino acid in the sample. In some embodiments, the sample of bodily fluid contains blood or serum from a subject.

The invention also relates to a method of quantifying a concentration of an amino acid in a sample of bodily fluid comprising: (a) contacting a sample of bodily fluid to: (i) a biosensor comprising at least one electrically conductive support or surface, the electrically conductive support or surface attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support or surface; or (ii) a system comprising a biosensor comprising: at least one electrically conductive support or surface, the electrically conductive support or surface attached to at least one hydrogel, the hydrogel comprising at least one electron mediator, at least one reduction agent, and at least one metabolic enzyme or functional fragment thereof; wherein the at least one enzyme or functional fragment thereof is at least 70% homologous to a phenylalanine dehydrogenase from *Geobacillus thermoglucosidiasus*; and an amperometer and/or voltmeter operably connected to the at least one electrically conductive support; or (iii) a test strip disclosed herein; or (b) determining a quantity of amino acid in the sample. In some embodiments, the method further comprises comparing a concentration value obtained by the quantifying or identifying steps to a threshold value associated with one or more metabolic diseases.

The invention further relates to a method comprising a step of contacting, wherein the step of contacting a sample of bodily fluid of a subject to any of the disclosed biosensors, systems, or test strips comprises contacting the sample for a sufficient period of time to allow oxidation of at least one amino acid in the sample of bodily fluid by the metabolic enzyme or functional fragment thereof. In some embodiments, the method does not comprise exposing the sample of bodily fluid to any external stimuli or reagent prior to contacting the sample to the at least one electrically conductive supports. In some embodiments, the method does not comprise exposing the sample of bodily fluid to iron ions and/or hydrozide ions prior to, simultaneously with, or after exposing the sample to the at least one electrode comprising a hydrogel. In some embodiments, the sample of bodily fluid contains blood or serum from a subject. In some embodiments, the sample of bodily fluid does not contain urine. In some embodiments, the sample of bodily fluid does not contain bodily fluid other than blood or blood serum.

The invention further relates to a method of diagnosing a metabolic disease in a subject comprising: (a) contacting a sample of bodily fluid to one or a combination of: (i) a biosensor comprising at least one electrically conductive support or surface, the electrically conductive support or surface attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support or surface; or (ii) a system comprising a biosensor comprising: at least one electrically conductive support or surface, the electrically conductive support or surface attached to at least one hydrogel, the hydrogel comprising at least one electron mediator, at least one reduction agent, and at least one metabolic enzyme or functional fragment thereof; and an amperometer and/or voltmeter operably connected to the at least one electrically conductive support; or (iii) a test strip disclosed herein; (b) quantifying one or more concentration values of amino acids in the sample; (c) comparing the one or more concentration values of amino acids in the sample to a threshold value of amino acid concentration identified as being in a healthy range or not within a range or concentration indicative or a aminoacidopathy; and (d) identifying the subject as having a metabolic disease if the one or more concentration values of amino acids in the sample exceed or fall below the threshold value. In some embodiments, the metabolic disease is chosen from at least one or a combination of: phenylketonuria, hyperammonemia, and maple syrup urine disease.

The invention also relates to a method of determining patient responsiveness to a therapy comprising: (a) contacting a sample of bodily fluid to one or a combination of: (i) a biosensor comprising at least one electrically conductive support or surface, the electrically conductive support or surface attached to a hydrogel, the hydrogel comprising at least one electron mediator, at least one reduction agent, and at least one metabolic enzyme or functional fragment thereof, wherein the hydrogel comprises alginate; and an amperometer and/or voltmeter operably connected to the at least one electrically conductive support or surface; or (ii) a system comprising a biosensor comprising: at least one electrically conductive support or surface, the electrically conductive support or surface attached to at least one hydrogel, the hydrogel comprising at least one electron mediator, at least one reduction agent, and at least one metabolic enzyme or functional fragment thereof; and an amperometer and/or voltmeter operably connected to the at least one electrically conductive support; or (iii) a test strip disclosed herein; (b) quantifying one or more amino acid concentration values; and (c) comparing the one or more concentration values to one or more threshold values associated with a metabolic disease.

The invention also relates to a test strip comprising a solid support and at least a first and a second electrode attached to the solid support, wherein the first electrode comprises a hydrogel, the hydrogel comprising either: (i) at least one electron mediator, at least one reduction agent, at least one metabolic enzyme or functional fragment thereof, and alginate; or (ii) at least one electron mediator, at least one reduction agent, at least one metabolic enzyme or functional fragment thereof chosen from a thermophilic bacterial species; wherein the second electrode is a control or reference electrode. In some embodiments, the test strip is adapted for a portable device comprising a voltmeter and/or amperometer and a digital display such that, when the test strip is contacted to the device, the first and second electrodes become operably connected to a closed electrical circuit comprising the voltmeter and/or amperometer and the digital display, and, upon contact with a sample of bodily fluid, the at least one metabolic enzyme or functional fragment thereof catalyzes oxidation of an amino acid resulting in a current on the first electrode corresponding to a concentration value of amino acid in the sample of bodily fluid, such concentration value readable on the display of the portable device. In some embodiments, the test strip comprises the at least one metabolic enzyme or functional fragment thereof that is at least 70% homolgous to SEQ ID NO:1 or SEQ ID NO:2.

The invention also relates to a method of manufacturing any of the disclosed biosensors, test strips, systems disclosed herein that comprise at least one electrode with a hydrogel, the method comprising: contacting the at least one electrode with a solution comprising at least one electron mediator, at least one reduction agent, at least one metabolic enzyme or functional fragment thereof, and alginate; subsequently contacting the at least one electrode with a calcium chloride solution with a concentration at or below about 150 mM. In some embodiments, the concentration of calcium chloride is at or below about 100 mM.

BRIEF DESCRIPTION OF THE DRAWINGS

FIG. 15 also depicts use of a molecular weight filter for filtration of sample components to reduce interference.

DETAILED DESCRIPTION OF THE INVENTION

Figure 1:
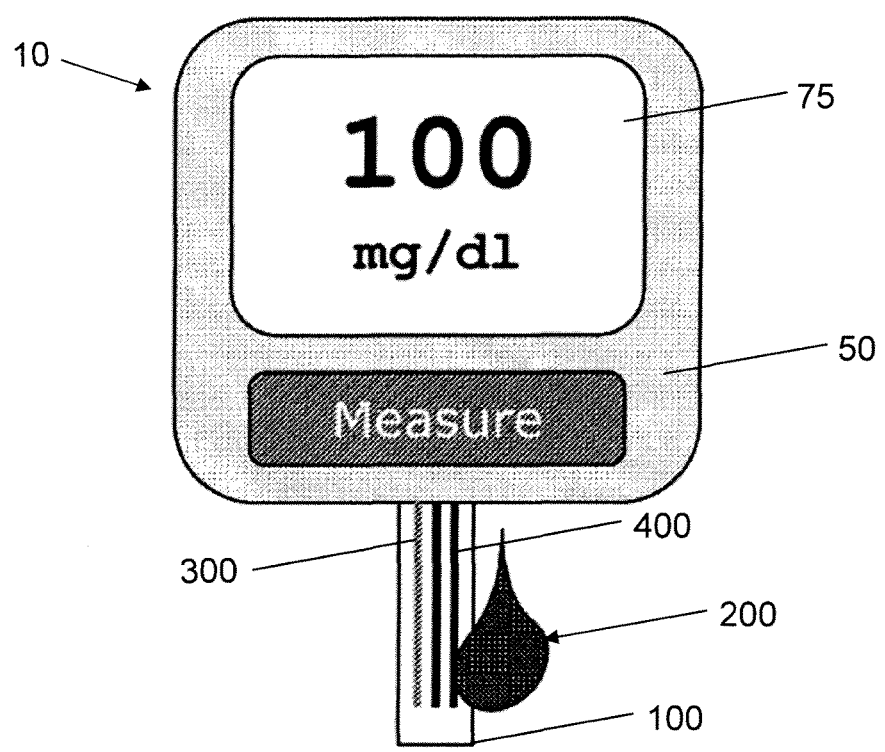
FIG. 1 depicts a schematic of a point-of-care device being placed in contact with a sample of bodily fluid.
Figure 2:
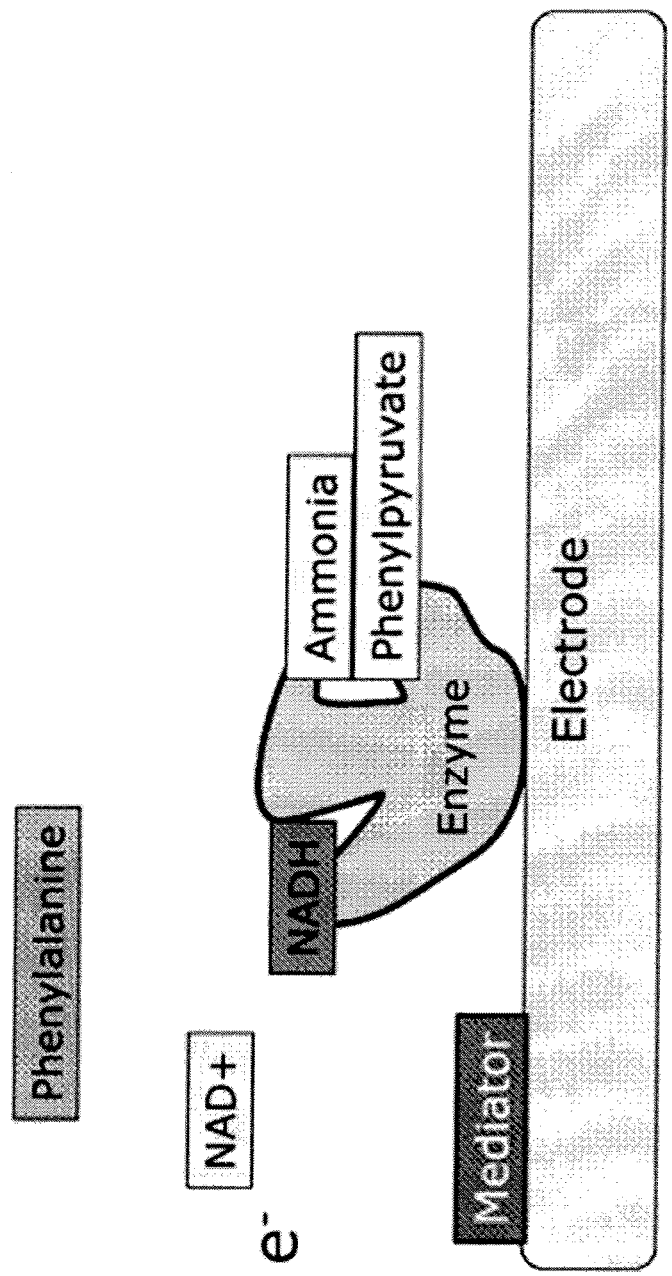
FIG. 2 depicts a schematic of a magnified surface of a first (measuring) electrode of the device. The embodiments illustrates immobilized enzyme capable of oxidizing phenylalanine into ammonia and phenylpyruvate. A reduction agent, in this case, NAD+, is reduced by the enzymatic reaction which causes electron (e−) transport to the conductive surface of the electrode.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "addressable location" as used herein means a discrete surface area or position on a solid support onto which one or a plurality of components are immobilized to functionalize the surface. In some embodiments, one or more components are immobilized or absorbed to a hydrogel attached to the surface of the at least one electrically conductive surface such that exposure of the one or plurality of components to a sample comprising an amino acid for a sufficient time period results in oxidation of the amino acids. In some embodiments, the invention relates to an electrode comprising one or a plurality of addressable locations of the electrode with a width or diameter from about 10 nanometers to about 10 centimeters. In some embodiments, the one or plurality of addressable locations of the array is spotted manually by a pipet or automatically by a robotic device.

As used herein, the terms "attach," "attachment," "adhere," "adhered," "adherent," or like terms generally refer to immobilizing or fixing, for example, a group, a compound or enzyme, to a surface, such as by physical absorption, chemical bonding, and like processes, or combinations thereof.

As used herein, the terms "biopsy" means a cell sample, collection of cells, or bodily fluid removed from a subject or patient for analysis. In some embodiments, the biopsy is a bone marrow biopsy, punch biopsy, endoscopic biopsy, needle biopsy, shave biopsy, incisional biopsy, excisional biopsy, or surgical resection.

As used herein, the terms "bodily fluid" means any fluid from a isolated from a subject including, but not necessarily limited to, blood sample, serum sample, urine sample, mucus sample, saliva sample, and sweat sample. The sample may be obtained from a subject by any means such as intravenous puncture, biopsy, swab, capillary draw, lancet, needle aspiration, collection by simple capture of excreted fluid.

As used herein the terms "electronic medium" mean any physical storage employing electronic technology for access, including a hard disk, ROM, EEPROM, RAM, flash memory, nonvolatile memory, or any substantially and functionally equivalent medium. In some embodiments, the software storage may be co-located with the processor implementing an embodiment of the invention, or at least a portion of the software storage may be remotely located but accessible when needed.

As used herein, the term "aminoacidopathy" is meant to refer to those diseases and disorders characterized by dysfunction of a metabolic catalysis of amino acids that results in over production or under production of amino acids in the body of a subject. Examples of aminoaciopathies are listed in the definition of a metabolic disease, terms that are used interchangeably in this application.

As used herein, "sequence identity" is determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). To use the term "homologus to" is synonymous with a measured "sequence identity."

The term "subject" is used throughout the specification to describe an animal from which a sample of bodily fluid is taken. In some embodiment, the animal is a human. For diagnosis of those conditions which are specific for a specific subject, such as a human being, the term "patient" may be interchangeably used. In some instances in the description of the present invention, the term "patient" will refer to human patients suffering from a particular disease or disorder. In some embodiments, the subject may be a human suspected of having or being identified as at risk to develop an aminoacidopathy. In some embodiments, the subject may be diagnosed as having at least one aminoacidopathy. In some embodiments, the subject is suspected of having or has been diagnosed with phenylketonuria. In some embodiments, the subject may be a human suspected of having or being identified as at risk to develop aminoacidopathy. In some embodiments, the subject may be a mammal which functions as a source of the isolated sample of bodily fluid. In some embodiments, the subject may be a non-human animal from which a sample of bodily fluid is isolated or provided. The term "mammal" encompasses both humans and non-humans and includes but is not limited to humans, non-human primates, canines, felines, murines, bovines, equines, and porcines.

As used herein, "conservative" amino acid substitutions may be defined as set out in Tables A, B, or C below. Metabolic enzymes include those amino acid sequences wherein conservative substitutions have been introduced by modification of polynucleotides encoding polypeptides of the invention. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A.

TABLE A

| Conservative Substitutions I | |
|---|---|
| Side Chain Characteristics | Amino Acid |
| Aliphatic | |
| Non-polar | G A P I L V F |
| Polar-uncharged | C S T M N Q |
| Polar-charged | D E K R |
| Aromatic | H F W Y |
| Other | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

| Conservative Substitutions II | |
|---|---|
| Side Chain Characteristic | Amino Acid |
| Non-polar (hydrophobic) | |
| Aliphatic: | A L I V P. |
| Aromatic: | F W Y |
| Sulfur-containing: | M |
| Borderline: | G Y |

TABLE B-continued

| Conservative Substitutions II | |
|---|---|
| Side Chain Characteristic | Amino Acid |
| Uncharged-polar | |
| Hydroxyl: | S T Y |
| Amides: | N Q |
| Sulfhydryl: | C |
| Borderline: | G Y |
| Positively Charged (Basic): | K R H |
| Negatively Charged (Acidic): | D E |

Alternately, exemplary conservative substitutions are set out in Table C.

TABLE C

| Conservative Substitutions III | |
|---|---|
| Original Residue | Exemplary Substitution |
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides comprising polypeptide sequences associated with the extracellular matrix described herein are intended to include polypeptides bearing one or more insertions, deletions, or substitutions, or any combination thereof, of amino acid residues as well as modifications other than insertions, deletions, or substitutions of amino acid residues.

As used herein, the term "prognosing" means determining the probable course and outcome of a disease.

As used herein, the term "functional fragment" means any portion of a polypeptide that is of a sufficient length to retain at least partial biological function that is similar to or substantially similar to the wild-type polypeptide upon which the fragment is based. In some embodiments, a functional fragment of a polypeptide associated with the function of a metabolic enzyme is a polypeptide that comprises at least 70, 75, 80, 85, 90, 95, 96, 97, 98, or 99% sequence identity of any polypeptide disclosed in Table 2 and has sufficient length to retain at least partial binding affinity to one or a plurality of ligands that bind to the polypeptide. In some embodiments, the fragment is a fragment of any polypeptide disclosed in Table 2 and has a length of at least about 10, about 20, about 30, about 40, about 50, about 60, about 70, about 80, about 90, or about 100 contiguous amino acids. In some embodiments, the fragment is a fragment of any polypeptide disclosed in Table 2 and has a length of at least about 50 amino acids. In some embodiments, the fragment is a fragment of any polypeptide disclosed in Table 2 and has a length of at least about 100 amino acids. In some embodiments, the fragment is a fragment of any polypeptide disclosed in Table 2 and has a length of at least about 150 amino acids. In some embodiments, the fragment is a fragment of any polypeptide disclosed in Table 2 and has a length of at least about 200 amino acids. In some embodiments, the fragment is a fragment of any polypeptide disclosed in Table 2 and has a length of at least about 250 amino acids.

As used herein, the terms "polypeptide sequence associated with the metabolic enzyme" means any polypeptide or fragment thereof, modified or unmodified by any macromolecule (such as a sugar molecule or macromolecule), that is produced naturally by cells in any multicellular organism and is a metabolic enzyme as disclosed herein or a functional fragment thereof. In some embodiments, a polypeptide sequence associated with the extracellular matrix is any polypeptide which sequence comprises any of the polypeptides disclosed in Table 2. In some embodiments, a polypeptide sequence associated with the metabolic enzyme is any polypeptide sequence comprising any of the polypeptides disclosed in Table 2 or a sequence that shares 85, 90, 95, 96, 97, 98, or 99% sequence identity with the polypeptides disclosed in Table 2 or a functional fragment thereof. In some embodiments, a polypeptide sequence associated with the metabolic enzyme consists of any of the polypeptides disclosed in Table 2 or a sequence that shares 85, 90, 95, 96, 97, 98, or 99% sequence identity with the polypeptides disclosed in Table 2.

As used herein, the term "antibody" refers to any immunoglobulin, whether natural or wholly or partially synthetically produced. In some embodiments, an antibody is a complex comprised of 4 full-length polypeptide chains, each of which includes a variable region and a constant region, e.g., substantially of the structure of an antibody produced in nature by a B cell. In some embodiments, an antibody is a single chain. In some embodiments, an antibody is cameloid. In some embodiments, an antibody is an antibody fragment. In some embodiments, an antibody is chimeric. In some embodiments, an antibody is bi-specific. In some embodiments, an antibody is multi-specific. In some embodiments, an antibody is monoclonal. In some embodiments, an antibody is polyclonal. In some embodiments, an antibody is conjugated (i.e., antibodies conjugated or fused to other proteins, radiolabels, cytotoxins). In some embodiments, an antibody is a human antibody. In some embodiments, an antibody is a mouse antibody. In some embodiments, an antibody is a rabbit antibody. In some embodiments, an antibody is a rat antibody. In some embodiments, an antibody is a donkey antibody. In some embodiments, the biosensor or system described herein comprises an antibody or plurality of antibodies.

Characteristic: As is used herein, the term "characteristic" refers to any detectable feature of a sample of bodily fluid that allows it to be distinguished from a comparable sample of bodily fluid. In some embodiments, a characteristic is an amount or identity of an amino acid. In some embodiments, a characteristic is an amount or sequence of a gene transcript. In some embodiments, a characteristic is an amount, sequence of, or modification of a amino acid. In some embodiments a characteristic is an amount of a carbohydrate. In some embodiments, a characteristic is an amount of a small molecule.

Comparable: As is used herein, the term "comparable" is used to refer to two entities that are sufficiently similar to permit comparison, but differing in at least one feature.

Metabolic Enzyme: As is used herein, the term "metabolic enzyme" means an enzyme responsible for catalysis of at least one step in the metabolic pathway of one or more amino acids. In some embodiments, the metabolic enzyme is phenylalanine dehydrogenase, glutamate dehydrogenase, respective functional fragments or a combination thereof or a fusion protein thereof.

As used herein the terms "metabolic disease" is any one of a group of disorders caused by a defect in an enzymatic step in the metabolic pathway of one or more amino acids or in a protein mediator necessary for transport of certain amino acids into or out of cells. In some embodiments, the metabolic disease is chosen from: Argininemia (ARG, arginase deficiency) Argininosuccinate acidemia (ASA, argininosuccinase) Citrullinemia type I (CIT-I, argininosuccinate synthetase) Citrullinemia type II (CIT-II, citrin deficiency) Defects of biopterin cofactor biosynthesis (BIOPT-BS) Defects of biopterin cofactor regeneration (BIOPT-RG) Homocystinuria (HCY, cystathionine beta synthase) Hyperphenylalaninemia (H-PHE) Hypermethioninemia (MET) Maple syrup urine disease (MSUD, branched-chain ketoacid dehydrogenase) Phenylketonuria (PKU, phenylalanine hydroxylase) Tyrosinemia type I (TYR-1, fumarylacetoacetate hydrolase), Tyrosinemia type II (TYR-II, tyrosine aminotransferase), and Tyrosinemia type III (TYR-III, hydroxyphenylpyruvate dioxygenase) where the parenthetical phrases after each disease state represent an abbreviation for the disease accompanies by the enzyme that is generally defective in the subject suffering from the disease state.

Polypeptide: The term "polypeptide", as used herein, generally has its art-recognized meaning of a polymer of at least three amino acids. Those of ordinary skill in the art will appreciate that the term "polypeptide" is intended to be sufficiently general as to encompass not only polypeptides having the complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying or significantly reducing activity. Thus, any polypeptide that retains activity and shares at least about 30-40% overall sequence identity, often greater than about 50%, 60%, 70%, 75%, 80%, or 85%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

As used herein, the term "threshold value" is the concentration of amino acid in a sample of bodily fluid that indicates whether the amount of amino acid in the sample is considered abnormally high or low resulting in a diagnosis or suspected diagnosis of a particular disorder, such as a metabolic disease. For instance, in the case of a blood sample, known threshold values for certain aminoacidopathies are indicated in Table 1 below:

TABLE 1

Aminoacidopathies and their associated amino acid markers detectable in a sample

| Disorder | Marker | Abnormal Range |
| --- | --- | --- |
| ARG | Arginine | >100 umol/L |
| ASA | Argininosuccinic acid | >4.0 umol/L |
| | ASA/Arg | >0.75 |
| CIT-I and CIT-II | Citrulline | >60 umol/L |
| | Cit/Tyr | >1.0 |
| | Cit/Arg | >6.0 |
| HCY and MET | Methionine | >70 umol/L |
| | Met/Phe | >1.2 |

TABLE 1-continued

Aminoacidopathies and their associated amino acid markers detectable in a sample

| Disorder | Marker | Abnormal Range |
| --- | --- | --- |
| MSUD | Leucine | >250 umol/L |
| | Valine | >250 umol/L |
| | Leu/Phe | >4.0 |
| | Val/Phe | >3.5 |
| PKU, H-PHE | Phenylalanine | >130 umol/L |
| BIOPT-BS and BIOPT-RG | Phe/Tyr | >2.0 |
| TYR-I, TYR-II, and TYR-III | Tyrosine | >250 umol/L |

In some embodiments, information about a threshold value or reference sample of bodily fluid is obtained prior to or simultaneously with information about an experimental sample of bodily fluid. In some embodiments, information about a reference cell or cell type is historical. In some embodiments, information about a threshold value or reference sample of bodily fluid is stored for example in a computer-readable storage medium. In some embodiments, comparison of a particular concentration value with a threshold value or reference sample of bodily fluid differentiates the concentration values of one or more amino acids in an experimental sample of bodily fluid with the threshold values thereby allowing a comparison that results in diagnosing a subject with one or more metabolic diseases or a change in severity of one or more metabolic diseases.

Reference Electrode: As will be understood from context, a reference electrode or control electrode is an electrically conductive support such as an electrode placed in a circuit with an at least one electrically conductive support comprising hydrogel and/or immobilized enzymes disclosed herein, to permit a relevant comparison of voltage difference between the reference or control electrode and the at least one electrically conductive support comprising hydrogel and/or immobilized enzymes disclosed herein.

Sample: As used herein, the term "sample" refers to a biological sample obtained or derived from a source of interest, as described herein. In some embodiments, a source of interest comprises an organism, such as an animal or human. In some embodiments, a biological sample comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or bronchioalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises bodily fluid. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc. in some embodiments, the methods disclosed herein do not comprise a processed sample.

The invention relates to an amino-acid biosensor for measuring a total concentration of a plurality of specific amino acids. The amino-acid biosensor comprises a measuring electrode which include as components, a mediator and an enzyme, which selectively act on the plurality of specific amino acids each serving as a substrate, and a counter electrode. In the amino-acid biosensor, the enzyme has a substrate affinity to each of the plurality of specific amino acids. The enzyme is operable to catalyze a reaction in each of the plurality of specific amino acids as a substrate so as to form a reaction product. The mediator is operable, during amino-acid concentration measurement, to carry electrons between the reaction product and the measuring electrode. Further, the amino-acid biosensor is designed to apply a voltage between the measuring electrode and the counter electrode at a measurement point in such a manner that, in an analytical curve representing a relationship between an applied voltage and a current value in a specific concentration for each of the plurality of specific amino acids, the applied voltage is a voltage allowing the variety of the current values for the amino acids in the same concentration and at the same applied voltage.

In some embodiments, the measuring electrode (at least a first electrode) further comprises a a hydrogel that comprises a coenzyme or reduction agent as a component. In some embodiments, the enzyme consists of a dehydrogenase. Further, the reaction product consists of a reduced coenzyme derived by reduction of the coenzyme, and the mediator is operable, during the amino-acid concentration measurement, to carry electrons from the reduced coenzyme to the measuring electrode.

In some embodiments, a biosensor or system disclosed herein is used in conjunction with the following:

1. a power source in electrical connection with the electrodes and capable of supplying an electrical potential difference between the electrodes sufficient to cause diffusion limited electro-oxidation of the reduced form of the mediator at the surface of the working electrode; and
2. at least one meter, (such as a voltmeter and/or amperometer) in electrical connection with the electrodes and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are hereby expressly incorporated by reference.

Many fluid samples may be analyzed. For example, human and non-human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues from humans and non-human animals can also be assayed, along with foods, fermentation products and environmental substances, which potentially contain environmental contaminants. In some embodiments, human serum is assayed with this invention.

After reaction is complete, a power source (e.g., a battery) applies a potential difference between electrodes. When the potential difference is applied, the amount of oxidized form of the mediator at the auxiliary electrode and the potential difference must be sufficient to cause diffusion-limited electro-oxidation of the reduced form of the at least one mediator at the surface of the working electrode. In some embodiments, the working electrode comprises a hydrogel disclosed herein. A current measuring meter (not shown) measures the diffusion-limited current generated by the oxidation of the reduced form of the mediator at the surface of the working electrode. The measured current may be accurately correlated to the concentration of one or more amino acids in sample when the following requirements are satisfied:

1. The rate of oxidation of the reduced form of the mediator is governed by the rate of diffusion of the reduced form of the mediator to the surface of the working electrode.
2. The current produced is limited by the oxidation of reduced form of the mediator at the surface of the working electrode.

To manufacture biosensor a roll of metallized film is fed through guide rolls into an ablation/washing and drying station. A laser system capable of ablating bottom plate element 14 is known to those of ordinary skill in the art. Non-limiting examples of which include excimer lasers, with the pattern of ablation controlled by mirrors, lenses, and masks. A non-limiting example of such a system is the LPX-300 or LPX-200 both commercially available from LPKF Laser Electronic GmbH, of Garbsen, Germany.

In the laser ablator, the metallic layer of the metallized film is ablated in a pre-determined pattern, to form a ribbon of isolated electrode sets. The metallized film is further ablated, after the isolated electrode sets are formed to create recesses positioned adjacent the electrochemical area. The ribbon is then passed through more guide rolls, with a tension loop and through an optional inspection camera. The camera is used for quality control in order to check for defects.

Reagent is compounded and applied in a liquid form to the center of the electrochemical area at a dispensing and drying station. Reagent application techniques are well known to one of ordinary skill in the art as described in U.S. Pat. No. 5,762,770, the disclosure of which is expressly incorporated herein by reference. It is appreciated that reagent may be applied to array in a liquid or other form and dried or semi-dried onto the center of the electrochemical area in accordance with this disclosure.

In addition, a roll or top plate element material is fed into an assembly station along with a roll of spacer material. Liners on either side of the spacer material are removed in that station and the top plate element or surface scaffold is applied to one side of the spacer material to form a top plate element/spacer subassembly. The top plate element/spacer subassembly is slit into the appropriate width for a row of biosensors. Next, a new release liner is added to the side of the spacer material opposite the cover and the subassembly is wound into a roll.

The ribbon of the reagent-coated bottom plate element is unwound and fed into a sensor assembly station along with the top plate element/spacer subassembly. The liner is removed from the spacer and the subassembly is placed on bottom plate element to cover reagent. Next, the assembled material is cut to form individual biosensors, which are sorted and packed into vials, each closed with a stopper, to give packaged sensor test strips.

Although ablating recesses is described herein, it is appreciated that the method of forming recesses in bottom plate element is also not limited. For example, the recesses may be formed by etching (e.g., using photoligographic methods) or otherwise removing a portion of the surface of top plate element. The nearest electrode edge is approximately 10 µm to 500 µm from the recess, preferably 100 µm to 400 µm from the recess, most preferably 200 µm to 300 µm from the recess. Biosensors that are formed with recesses in accordance with this disclosure yield a reagent profile with generally uniform thickness of chemistry. A generally uniform thickness of chemistry allows for more accurate sample analysis.

The processes and products described above include a disposable biosensor, especially for use in diagnostic devices.

Electrode

In some embodiments, the biosensor, system or test strip disclosed herein comprise one or more electrodes. In some embodiments, the one or more electrodes transmit current variation generated by the reaction between the metabolic enzyme or functional fragment thereof and its one or more substrates. In some embodiments, the one or more substrates are one or more amino acids. In some embodiments, the electrodes comprise metal. In some embodiments, the electrodes comprise a carbon scaffold upon which a metal is deposited. In some embodiments, the electrodes comprise a carbon scaffold of carbon nanotubes.

Electrode structures which are suitable for the present invention and methods for the production of such structures have already been suggested in biosensor technology for other purposes. In this regard, reference is made to U.S. Pat. No. 6,645,359 and its content is incorporated herein by reference in its entirety. Electrodes or Electrically conductive tracks are created or isolated on first surface. Tracks represent the electrodes of biosensor. As used herein, the phrase "electrode set" is a set of at least two electrodes, for example 2 to 200, or 3 to 20, electrodes. These electrodes may, for example, be a working (or measuring) electrode and an auxiliary electrode. In some embodiments, tracks cooperate to form an interdigitated electrode array positioned within the periphery of recesses and leads that extend from array and between recesses toward end.

Tracks are constructed from electrically conductive materials. Non-limiting examples of electrically-conductive materials include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, tracks include gold, platinum, palladium, iridium, or alloys of these metals, since such noble metals and their alloys are unreactive in biological systems. In some embodiments, the track is a working electrode made of silver and/or silver chloride, and track is an auxiliary electrode that is also made of silver and/or silver chloride and is substantially the same size as the working electrode.

Tracks are isolated from the rest of the electrically conductive surface by laser ablation. Techniques for forming electrodes on a surface using laser ablation are known.

Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE", the disclosure of which is expressly incorporated herein by reference. Tracks are preferably created by removing the electrically conductive material from an area extending around the electrodes. Therefore, tracks are isolated from the rest of the electrically-conductive material on a surface by a gap having a width of about 5 µm to about 500 µm, preferably the gap has a width of about 100 µm to about 200 µm. Alternatively, it is appreciated that tracks may be created by laser ablation alone on bottom substrate. Further, tracks may be laminated, screen-printed, or formed by photolithography.

Multi-electrode arrangements are also possible in accordance with this disclosure. For example, it is contemplated that a biosensor may be formed that includes an additional electrically conductive track. In a three-electrode arrangement such as the arrangement depicted in FIG. 4, the first track is a working electrode, the second is a counter electrode, and the third electrode is a reference electrode. It is also appreciated that an alternative three-electrode arrangement is possible where tracks are working electrodes and a third electrode is provided as an auxiliary or reference electrode. It is appreciated that the number of tracks, as well as the spacing between tracks in array may vary in accordance with this disclosure and that a number of arrays may be formed as will be appreciated by one of skill in the art. In some embodiments, the electrodes are embedded on or attached to a solid support, such as a test strip comprising a plastic and/or paper material.

Micro-electrode arrays are structures generally having two electrodes of very small dimensions, typically with each electrode having a common element and electrode elements or micro-electrodes. If "interdigitated" the arrays are arranged in an alternating, finger-like fashion (See, e.g., U.S. Pat. No. 5,670,031). These are a sub-class of micro-electrodes in general. Interdigitated arrays of micro-electrodes, or IDAs, can exhibit desired performance characteristics; for example, due to their small dimensions, IDAs can exhibit excellent signal to noise ratios.

Interdigitated arrays have been disposed on non-flexible substrates such as silicon or glass substrates, using integrated circuit photolithography methods. IDAs have been used on non-flexible substrates because IDAs have been considered to offer superior performance properties when used at very small dimensions, e.g., with feature dimensions in the 1-3 micrometer range. At such small dimensions, the surface structure of a substrate (e.g., the flatness or roughness) becomes significant in the performance of the IDA. Because non-flexible substrates, especially silicon, can be processed to an exceptionally smooth, flat, surface, these have been used with IDAs. In some embodiments, the at least one electrode is a component of any IDA disclosed herein.

Hydrogel

The hydrogel may be a cross-linked polymeric material that swells in water but does not dissolve. It is envisioned that the hydrogel may be capable of absorbing at least about 1 to about 10 times, and in one embodiment at least about 100 times, its own weight of a liquid. The hydrogel chosen for use in the biosensor should depend directly on the method of functionalization. It is envisioned that the hydrogel may be biocompatible. In some embodiments, the hydrogel comprises sodium alginate. In some embodiments, the hydrogel comprises from about 0.1% to about 5% alginate weight/volume. In some embodiments, the hydrogel comprises from about 0.1% to about 4% alginate weight/volume. In some embodiments, the hydrogel comprises from about 0.1% to about 3% alginate weight/volume. In some embodiments, the hydrogel comprises from about 0.1% to about 2% alginate weight/volume. In some embodiments, the hydrogel comprises from about 0.1% to about 1% alginate weight/volume. In some embodiments, the hydrogel comprises from about 0.1% to about 1% alginate weight/volume. In some embodiments, the hydrogel comprises from about 0.2% to about 1% alginate weight/volume. In some embodiments, the hydrogel comprises sodium alginate. In some embodiments, the hydrogel comprises from about 0.3% to about 1% alginate weight/volume. In some embodiments, the hydrogel comprises from about 0.4% to about 1% alginate weight/volume In some embodiments, the hydrogel comprises from about 0.5% to about 1% alginate weight/volume. In some embodiments, the hydrogel comprises from about 0.6% to about 1% alginate weight/volume. In some embodiments, the hydrogel comprises from about 0.7% to about 1% alginate weight/volume. In some embodiments, the hydrogel comprises from about 0.8% to about 1% alginate weight/volume. In some embodiments, the hydrogel comprises from about 0.9% to about 1% alginate weight/volume. In some embodiments, the hydrogel comprises from about 1.0% to about 3.0% alginate weight/volume. In some embodiments, the hydrogel comprises from about 1.0% to about 2.0% alginate weight/volume. In some embodiments, the hydrogel comprises from about 1.0% to about 1.5% alginate weight/volume. In some embodiments, the hydrogel comprises about 1%, about 2%, or about 3% alginate weight/volume. In some embodiments, the hydrogel comprises sodium alginate. The aliginate may be any individual polymer of alginate used in bulk form or repetitive pattern of monomers, G blocks, M blocks, and/or GM blocks. In some embodiments the alginate comprises the formula:

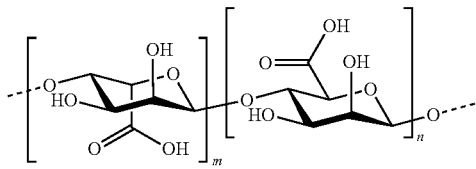

where m and n are any positive integer. In some embodiments, the hydrogel may be polymerized from acrylic monomers. The acrylic monomer may be one or a combination of the following: acrylamido-glycolic acid, acrylamido-methyl-propa-ne-sulfonic acid, acrylamido-ethylphosphate, diethyl-aminoethyl-acrylamide-, trimethyl-amino-propyl-methacrylamide, N-octylacrylamide, N-phenyl-acrylamide and tert-butyl-acrylamide. In embodiments in which the device contains a cross-linking agent, exemplary cross-linking agents may be N,N'-methylene-bis-acrylamide, N,N'-methylene-bismethacrylamide, diallyltatardiamide and poly(ethylene glycol)dimethacrylate. Examples of suitable hydrogels may also include silicon wafers, borosilicate glass substrates, 2-hydroxyethyl methacrylate (HEMA), N-Isopropylacrylamide (NIPAAm), and polyethylene glycol (PEG).

The hydrogel may include any number of molecules. For example, the hydrogel may include a polymerized monomer or hydrogel a cross linking agent and optionally a chemical or UV-light activated inducer agent. Examples of such monomers or dimers include vinyl acetates, vinyl pyrrolidones, vinyl ethers, olefins, styrenes, vinyl chlorides, ethylenes, acrylates, methacrylates, nitriles, acrylamides, maleates, epoxies, epoxides, lactones, ethylene oxides, ethylene glycols, ethyloxazolines, amino acids, saccharides, proteins, anhydrides, amides, carbonates, phenylene oxides, acetals, sulfones, phenylene sulfides, esters, fluoropolymers, imides, amide-imides, etherimides, ionomers, aryletherketones, amines, phenols, acids, benzenes, cinnamates, azoles, silanes, chlorides, and epoxides, N,N'-methylenebisacrylamide, methylenebismethacrylamide ethyleneglycol-dimethacrylate, N,N'-methylenebisacrylamide, polyethyleneglycoldiacrylate (PEGDA), polyethyleneglycoldimethacrylate (PEGDMA), polyethyleneglycoldiacrylate (PEGDA), polyethyleneglycoldimethacrylate (PEGDMA), poly(vinyliden fluoride) (PVdF) based polymer, a polyacrylonitrile (PAN) based polymer, a polymethylmethacrylate (PMMA) based polymer, a polyvinyl chloride (PVC) based polymer, and a mixture of the poly(vinyliden fluoride) (PVdF) based polymer, polyacrylonitrile (PAN) based polymer, polymethylmethacrylate (PMMA) based polymer, and polyvinyl chloride (PVC) based polymer, and mixtures of any two or more thereof. IN some embodiments, the hydrogel does not comprise 3,4-dihydroxybenzoic acid (3, 4-DHB) or an analog thereof.

Cross linking agents and optionally the chemical or UV-light activated inducer agent may include N,N'-methylenebisacrylamide, methylenebismethacrylamide ethyleneglycol-dimethacrylate and agent N,N'-methylenebisacrylamide. Irgacure 2959 (Ciba); 2,2-dimethoxy-2-phenylacetophenone, 2-methoxy-2-phenylacetone, benzyldimethyl-ketal, ammonium sulfate, benzophenone, ethyl benzoin ether, isopropyl benzoin ether, .alpha.-methyl benzoin ether, benzoin phenyl ether, 2,2-diethoxy acetophenone, 1,1-dichloro acetophenone, 2-hydroxy-2-methyl-1-phenylpropane 1-on, 1-hydroxy cyclohexyl phenyl ketone, antraquinone, 2-ethyl antraquinone, 2-chloroantraquinone, tioxantone, isopropyltioxantone, chloro tioxantone, 2,2-chlorobenzophenone, benzyl benzoate, and benzoyl benzoate, TEMED, and ammonium persulfate (APS). In some embodiments, hydrogel comprises a protein, peptide, glycoprotein, proteoglycans, glycosaminoglycans, and/or carbohydrate that is secreted by cells into the extracellular environment. In some embodiments, the secreted protein, peptide, glycoprotein, proteoglycans, glycosaminoglycans, and/or carbohydrate, or structures composed thereof.

In some embodiments, the invention relates to a coated biosensor device comprising at least one coating, wherein the biosensor comprises a metabolic enzyme covalently bound or immobilized to the coating, wherein the metabolic enzyme shares at least 70% sequence identify to SEQ ID NO:1 or SEQ ID NO:2 or shares at least 70% sequence identify to functional fragments of SEQ ID NO:1 or SEQ ID NO:2. In some embodiments, the invention relates to a coated biosensor device comprising at least one coating, wherein the biosensor comprises a metabolic enzyme covalently bound or immobilized within the coating, wherein the coating comprises a composition comprising a hydrogel matrix, said matrix comprising any one or combination of: alginate, trehalose, at least one electron mediator, and at least one reduction agent. In some embodiments, the invention relates to a coated biosensor device comprising at least one coating, wherein the biosensor comprises a metabolic enzyme covalently bound or immobilized to the coating, wherein the coating comprises a composition comprising a hydrogel matrix, said matrix comprising any one or combination of: poly(ethylene glycol)dimethyacrylate with a molecular weight of about 1000 (PEGDMA-1000), 2-hydroxy-2 methyl propiophenone (HMPP) and at least one acrylate, wherein the acrylate is selected from the group consisting of methacrylic acid (MAA) and methyl methacrylate (MMA), wherein the ratio of PEGDMA:Acrylate is from about 10:90 mol % to about 70:30 mol %, and said HMPP is at a concentration of from about 0.2% to about 0.6%, total weight.

In some embodiments, the hydrogel solution prior to curing comprises trehalose or an analog thereof at a concentration from about 1 nM to about 999 mM. In some embodiments, the hydrogel solution prior to curing comprises trehalose at a concentration from about 1 μM to about 10 mM. In some embodiments, the hydrogel solution prior to curing comprises trehalose at a concentration from about 1 μM to about 9 mM. In some embodiments, the hydrogel solution prior to curing comprises trehalose at a concentration from about 1 μM to about 8 mM. In some embodiments, the hydrogel solution prior to curing comprises trehalose at a concentration from about 1 μM to about 7 mM. In some embodiments, the hydrogel solution prior to curing comprises trehalose at a concentration from about 1 μM to about 6 mM. In some embodiments, the hydrogel solution prior to curing comprises trehalose at a concentration from about 1 μM to about 5 mM. In some embodiments, the hydrogel solution prior to curing comprises trehalose at a concentration from about 1 μM to about 4 mM. In some embodiments, the hydrogel solution prior to curing comprises trehalose at a concentration from about 1 μM to about 3 mM. In some embodiments, the hydrogel solution prior to curing comprises trehalose at a concentration from about 1 μM to about 2 mM. In some embodiments, the hydrogel solution prior to curing comprises trehalose at a concentration from about 1 μM to about 1 mM. In some embodiments, the hydrogel solution prior to curing comprises trehalose at a concentration from about 10 μM to about 1 mM. In some embodiments, the hydrogel solution prior to curing comprises trehalose at a concentration from about 100 μM to about 1 mM. In some embodiments, the hydrogel solution prior to curing comprises trehalose at a concentration from about 200 μM to about 1 mM. In some embodiments, the hydrogel solution prior to curing comprises trehalose at a concentration from about 300 μM to about 1 mM. In some embodiments, the hydrogel solution prior to curing comprises trehalose at a concentration from about 400 μM to about 1 mM. In some embodiments, the hydrogel solution prior to curing comprises trehalose at a concentration from about 500 μM to about 1 mM. In some embodiments, the hydrogel solution prior to curing comprises trehalose at a concentration from about 600 μM to about 1 mM. In some embodiments, the hydrogel solution prior to curing comprises trehalose at a concentration from about 700 μM to about 1 mM. In some embodiments, the hydrogel solution prior to curing comprises trehalose at a concentration from about 800 μM to about 1 mM. In some embodiments, the hydrogel solution (prior to contacting with the electrode) comprises trehalose at a concentration from about 900 μM to about 1 mM.

Mediators

In some embodiments, the hydrogel comprises a mediator. In some embodiments, the mediator facilitates transport of electrons to the electrode. In some embodiments, the mediator is attached to the electrode. In some embodiments, the mediator is embedded in the hydrogel. In some embodiments, the hydrogel comprises one or a combination of mediators chosen from: mediator 2-Acrylamido-2-methyl-propanel, sulfonic acid IV, ethacrylic acid, 2-Sulfoethyl methacrylate, and 2-Propene-1-sulfonic acid.

U.S. Pat. No. 4,254,222 (1981; Owen) and U.S. Pat. No. 4,351,899 (1982; Owen) disclose an assay for .beta.-hydroxybutyrate where 3-hydroxybutyrate is oxidized to acetoacetate by .beta.-hydroxybutyrate dehydrogenase (HBDH) in the presence of nicotinamide adenine dinucleotide (NAD.sup.+). The reduced NADH produced from this reaction, in turn, reacts with a tetrazolium dye to form a colored formazan compound. The degree and intensity of the color transition correlates to the concentration of .beta.-hydroxybutyrate in the sample solutions.

U.S. Pat. No. 5,510,245 (1996; Magers) and U.S. Pat. No. 5,326,697 (1994; Magers) disclose an improved calorimetric method that utilizes a reductive pathway based on lipoamide dehydrogenase (LADH) and a thiol-sensitive indicator dye such as Ellman's reagent. It was found the NADH, produced from the .beta.-hydroxybutyrate dehydrogenase enzyme reaction, can interact with lipoamide dehydrogenase (LADH) and D,L-lipoamide to form a thiol compound (6,8-dimercaptooctamide). The 6,8-dimercaptooctamide then interacts with a thiol-responsive indicator dye such as Ellman's reagent. Upon reaction, the thiol-sensitive indicator dye undergoes a detectable color transition that can be used to measure the level of 3-hydrobutyrate in the blood sample. The colorimetric methods for 3-hydrobutyrate suffer the disadvantages of poor stability, interference from co-existing species such as ascorbate, glutathione etc. in the blood, and insufficient sensitivity and accuracy.

NAD- and NADP-dependent enzymes are of great interest insofar as many have substrates of clinical value, such as glucose, D-3-hydroxybutyrate, lactate, ethanol, and cholesterol. Amperometric electrodes for detection of these substrates and other analytes can be designed by incorporating this class of enzymes and establishing electrical communication with the electrode via the mediated oxidation of the reduced cofactors NADH and NADPH.

NAD- and NADP-dependent enzymes are generally intracellular oxidoreductases. The oxidoreductases are further classified according to the identity of the donor group of a substrate upon which they act. The category of oxidoreductases is also broken down according to the type of acceptor utilized by the enzyme. The enzymes of relevance have NAD+ or NADP+ as acceptors. These enzymes generally possess sulphydryl groups within their active sites and hence can be irreversibly inhibited by thiol-reactive reagents such as iodoacetate. An irreversible inhibitor forms a stable compound, often through the formation of a covalent bond with a particular amino acid residue that is essential for enzymatic activity. U.S. Pat. No. 6,541,216 (2003; Wilsey et al.) discloses a biosensor and method to test blood ketone bodies using an amperometric meter. The test strip has a reagent that is reactive with .beta.-hydroxybutyrate in sample solution to generate an electrical output signal, which is related to the concentration of .beta.-hydroxybutyrate in the sample solution. The reagent in this method includes ferricyanide salt as mediator, .beta.-hydroxybutyrate dehydrogenase as the first enzyme operative to catalyze the oxidation of .beta.-hydroxybutyrate, NAD+ as a cofactor corresponding to the first enzyme, and diaphorase as the second enzyme operative to catalyze the oxidation of a reduction form of the cofactor (NADH). The oxidation form of the mediator will accept the electron from the second enzyme and generates an electrical signal at the electrode surface, which is related to the concentration level of .beta.-hydroxybutyrate.

U.S. Pat. No. 6,736,957 (2004; Forrow et al.) and a research paper (N. J. Forrow et. al, Biosensors & Bioelectronics, 2005, 20, 1617-1625) disclose an amperometric biosensor for .beta.-hydroxybutyrate based on the discovery of NAD+ and NADP-mediator compounds that do not bind irreversibly to thiol groups in the active sites of intracellular dehydrogenase enzymes. These mediator compounds such as 1,10-phenanthroline quinone (1,10-PQ), which is used as an electron mediator in their electrochemical measurement system, can increase the stability and reliability response in amperometric electrodes constructed from NAD- and NADP-dependent enzyme. The dry reagents include 1,10-phenanthroline quinone (1,10-PQ), .beta.-hydroxybutyrate dehydrogenase and NAD+ as the cofactor. This sensor shows reliable and sensitive response to the concentration levels of .beta.-hydroxybutyrate in blood samples. Meldola's Blue (MB) was also studied as a mediator in the system, but it was found that MB did not work well in their electrochemical test system due to the inhibition of .beta.-hydroxybutyrate dehydrogenase enzyme activity by MB and poor long term stability of the test strips.

The dehydrogenase enzymes such as, for example, glucose dehydrogenase, D-3-hydroxybutyrate dehydrogenase (HBDH), and lactate dehydrogenase et. al are known to be common dehydrogenases for construction of biosensors. As disclosed by Forrow et al., there are certain mediators that are considered efficient mediators for NADH but are irreversible enzyme inhibitors such as Meldola's blue, 4-methyl-1,2-benzoquinone (4-MBQ), 1-methoxy phenazine methosulphate (1-Meo-PMS) and 2,6-dichloroindophenol (DCIP), which cause losing the activity of enzymes, insensitive response and poor stability in sensors containing dehydrogenase enzymes. In some embodiments, the biosensor, system, or test strip comprise any one or more of the mediators disclosed herein. In some embodiments, the mediator is chosen from one or a combination of: ortho-quinones, para-quinones and quinonimines in their basic structural elements. The representative examples of the quinoid structure type include, but are not limited to, benzo-.alpha.-phenazoxonium chloride, Meldola's Blue (MB), 3,4-methyl-1,2-benzoquinone, 1-methoxy phenazine methosulphate, 1,10-phenanthroline quinone (1,10-PQ). in some embodiments, the at least one mediator is selected from one or a mixture of the following compounds:

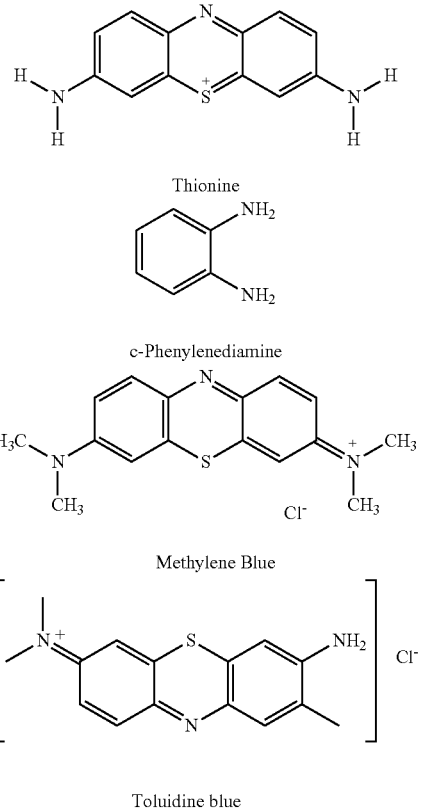

Thionine c-Phenylenediamine

Methylene Blue

Toluidine blue

Cofactors/Reduction Agent

Enzymes

Any one or more metabolic enzymes may be chosen to used with the present invention. Metabolic enzymes that can be used individually or in combination with the biosensor, system or test strip disclosed herein include: any bacterial clone of phenylalanine dehydrogenase, histidine ammonia lyase, mistidine oxidase. phenylalanine lyase, glutamate dehydrogenase. In some embodiments the enzyme is chosen from any one or combination of enzymes disclosed below or their respective functional fragments that are at least 70%, 80%, 85%, 90%, 95%, 96%, 97%, 98%, or 99% homolgous to the full-length enzyme or nucleic acid encoding such enzyme.

| Organism | Enzyme | GenBank Accession No | SEQ ID NO |
| --- | --- | --- | --- |
| Thermoactinomyces intermedius | phenylalanine dehydrogenase | D00631.1 | 2 |
| Solanum lycopersicum | phenylalanine ammonialyase | XM_004246602 | 7 |
| Thermoactinomyces intermedius | phenylalanine dehydrogenase | DD421709.1 | 8 |
| Caenorhabditis remanei | phenylalanine dehydrogenase | XM_003102740 | 9 |
| Arabidopsis thaliana | glutamate dehydrogenase | NM_121822.3 | 10 |
| Spirochaeta africana | Hisitidine ammonia lyase | NC_017098.1 | |

SEQ ID NO: 2

MRDVFEMMDRYGHEQVIFCRHPQTGLKAIIALHNTTAGPALGGCRMIPYA

STDEALEDVLRLSKGMTYKCSLADVDFGGGKMVIIGDPKKDKSPELFRVI

-continued

GRFVGGLNGRFYTGTDMGTNPEDFVHAARESKSFAGLPKSYGGKGDTSIP

TALGVFHGMRATARFLWGTDQLKGRVVAIQGVGKVGERLLQLLVEVGAYC

KIADIDSVRCEQLKEKYGDKVQLVDVNRIHKESCDIFSPCAKGGVVNDDT

IDEFRCLAIVGSANNQLVEDRHGALLQKRSICYAPDYLVNAGGLIQVADE

LEGFHEERVLAKTEAIYDMVLDIFHRAKNENITTCEAADRIVMERLKKLT

DIRRILLEDPRNSARR

SEQ ID NO: 7

MASSIVQNGHVNGEAMDLCKKSINVNDPLNWEMAAESLRGSHLDEVKKMV

DEFRKPIVKLGGETLTVAQVASIANVDNKSNGVKVELSESARAGVKASSD

WVMDSMGKGTDSYGVTTGFGATSHRRTKNGGALQKELIRFLNAGVFGNGT

ESSHTLPHSATRAAMLVRINTLLQGYSGIRFEILEAITKLINSNITPCLP

LRGTITASGDLVPLSYIAGLLTGRPNSKAVGPNGEKLNAEEAFRVAGVTS

GFFELQPKEGLALVNGTAVGSGMASMVLFESNILAVMSEVLSAIFAEVMN

GKPEFTDYLTHKLKHHPGQIEAAAIMEHILDGSSYVKAAQKLHEMDPLQK

PKQDRYALRTSPQWLGPQIEVIRAATKMIEREINSVNDNPLIDVSRNKAL

HGGNFQGTPIGVSMDNTRLALASIGKLMFAQFSELVNDYYNNGLPSNLTA

GRNPSLDYGLKGAEIAMASYCSELQFLANPVTNHVQSAEQHNQDVNSLGL

ISARKTAEAVDILKLMSSTYLVALCQAIDLRHLEENLRSAVKNTVSQVAK

RTLTMGANGELHPARFCEKELLRVVDREYVFAYADDPCSSTYPLMQKLRQ

VLVDHAMKNGESEKNVNSSIFQKIVAFEDELKAVLPKEVESARAVVESGN

PAIPNRITECRSYPLYRLVRQELGSELLTGEKVRSPGEEIDKVFTAMCNG

QIIDPLLECLKSWNGAPLPIC

SEQ ID NO: 8
```
     atgcgcgacg tgtttgaaat gatggaccgc tatggccacg agcaggtcat tttttgccgt
  61 catccgcaaa ccggtctcaa agcgatcatc gccttgcata atacaaccgc ggggccggct
 121 ttgggtggat gccgcatgat cccgtatgct cgacggacg aagccttgga ggatgttttg
 181 cggttgtcca aaggcatgac ctataaatgc agtctggcgg atgtggactt tggcggggga
 241 aaaatggtta tcatcggcga tccgaaaaaa gataaatcgc ggagttgtt tcgcgtgatc
 301 ggccgttttg tgggcgggtt aaacggccgt ttctataccg gaaccgacat gggaaccaat
 361 ccggaagatt ttgtccatgc cgccagggaa tcgaaatctt ttgccggatt gccgaaatcg
 421 tacggcggaa aggggggacac atccattccc accgcgctcg gggtgtttca cggaatgcgg
 481 gccaccgccc ggtttttatg ggggacggat cagctgaaag gcgtgtggt tgccatccaa
 541 ggagtcggca aggtgggaga gcgcttgttg cagcttttgg tcgaagtggg ggcttactgc
 601 aaaattgccg acatcgattc ggtgcgatgc gaacagctga agaaaagta tggcgacaag
 661 gtccaattgg tggatgtgaa ccggattcac aaggagagtt gcgatatttt ctcgccttgc
 721 gccaaaggcg gcgtggtcaa tgatgacacc attgacgagt tccgttgcct ggccattgtc
 781 ggatccgcca acaaccaact ggtggaagac cggcatgggg cactgcttca aaacggagc
 841 atttgttatg cacccgatta tctggtgaat gccggcgggc tgattcaagt ggctgatgaa
 901 ctggaaggct tccatgaaga gagtgctc gccaaaaccg aagcgattta tgacatggtc
 961 ctggatattt tcaccgggc gaaaaatgag aatattacca cttgtgaggc agcggaccgg
1021 atcgtgatgg agcgtttgaa aaagttaacc gatattcgcc ggatcttgtt ggaggatccc
1081 cgcaacagcg caaggaggta a
```

-continued

SEQ ID NO: 9

MDFKAKLLAEMAKKRKAVSGLEVKEGGAKFVRGADLESKRTQEY

EAKQEELAIKKRKADDEILQESTSRAKIVPEVPEAEFDEKTPMPEIHARLRQRGQPIL

LFGESELSVRKRLHQLEIEQPELNEGWENEMQTAMKFIGKEMDKAVVEGTADSATRHD

IALPQGYEEDNWKSIEHASTLLGVGDEMKRDCDIILSICRYILARWARDLNDRPLDVK

KTAQGMHEAAHHKQTTMHLKSLMTSMEKYNVNNDIRHHLAKICRLLVIERNYLEANNA

YMEMAIGNAPWPVGVTRSGIHQRPGSAKAYVSNIAHVLNDETQRKYIQAFKRLMTKLQ

EYFPTDPSKSVEFVKKSV

SEQ ID NO: 10

MNALAATNRNFKLAARLLGLDSKLEKSLLIPFREIKVECTIPKD

DGTLASFVGFRVQHDNARGPMKGGIRYHPEVDPDEVNALAQLMTWKTAVAKIPYGGAK

GGIGCDPSKLSISELERLTRVFTQKIHDLIGIHTDVPAPDMGTGPQTMAWILDEYSKF

HGYSPAVVTGKPIDLGGSLGRDAATGRGVMFGTEALLNEHGKTISGQRFVIQGFGNVG

SWAAKLISEKGGKIVAVSDITGAIKNKDGIDIPALLKHTKEHRGVKGFDGADPIDPNS

ILVEDCDILVPAALGGVINRENANEIKAKFIIEAANHPTDPDADEILSKKGVVILPDI

YANSGGVTVSYFEWVQNIQGFMWEEEKVNDELKTYMTRSFKDLKEMCKTHSCDLRMGA

FTLGVNRVAQATILRGWGA

Solid Support

There are many forms of amino acid measuring devices; one common type is represented by hand-held electronic meters which receive blood samples via enzyme-based test strips. In using these systems, the patient may for example lances a finger or alternate body site to obtain a blood sample, the strip is inserted into a test strip opening in the meter housing, the sample is applied to the test strip and the electronics in the meter convert a current generated by the enzymatic reaction in the test strip to a amino acid concentration value.

Solid supports of the invention may be solid state but are a flexible substrate. According to the invention, the interdigitated array or at least one electrode is disposed proximal to, e.g., on, a flexible substrate. To act as a flexible substrate, a material must be flexible and also insulating, and is typically relatively thin. The substrate should be capable of adhering components of an IDA, or additional components of a sensor, to its surface. Such thin, insulative, flexible substrates are known in the art of flexible circuits and flex circuit photolithography. "Flexible substrates" according to the present disclosure can be contrasted to non-flexible substrates used in integrated circuit (IC) photolithography but not in flexible circuit photolithography. Examples of non-flexible substrates used in IC photolithography include silicon, aluminum oxide, and other ceramics. These non-flexible substrates are chosen to be processable to a very flat surface. Typical flexible substrates for use in the invention are constructed of thin plastic materials, e.g., polyester, especially high temperature polyester materials; polyethylene naphthalate (PEN); and polyimide, or mixtures of two or more of these. Polyimides are available commercially, for example under the trade name Kapton®, from I. E. duPont de Nemours and Company of Wilmington, Del. (duPont). Polyethylene naphthalate is commercially available as Kaladex®, also from duPont. A particularly preferred flexible substrate is 7 mil thick Kaladex® film.

Interdigitated arrays of the invention can be used in applications generally known to incorporate electrodes, especially applications known to involve interdigitated arrays of electrodes. Various applications are known in the arts of electronics and electrochemistry, including applications relating to process and flow monitoring or control, and chemical analytical methods. The arrays may be particularly useful as a component of an electrochemical sensor, where there is added value, benefit, or cost efficiency, to the use of a flexible substrate, or where there is value, benefit, or cost efficiency in having an interdigitated array of dimensions relatively larger than the dimensions of interdigitated arrays conventionally disposed on non-flexible substrates.

An interdigitated array of the invention can, for example, be included in an electrochemical sensor (sometimes referred to as a "biosensor" or simply "sensor") used in electrochemical detection methods. Electrochemical detection methods operate on principles of electricity and chemistry, or electrochemistry, e.g., on principles of relating the magnitude of a current flowing through a substance, the resistance of a substance, or a voltage across the substance given a known current, to the presence of a chemical species within the substance. Some of these methods can be referred to as potentiometric, chronoamperometric, or impedance, depending on how they are practiced, e.g., whether potential difference or electric current is controlled or measured. The methods and sensors, including sensors of the invention, can measure current flowing through a substance due directly or indirectly to the presence of a particular chemical compound (e.g., an analyte or an electroactive compound), such as a compound within blood, serum, interstitial fluid, or another bodily fluid, e.g., to identify levels of amino acids, blood urea, nitrogen, cholesterol, lactate, and the like. Adaptations of some electrochemical methods and electrochemical sensors, and features of their construction, electronics, and electrochemical operations, are described, for example, in U.S. Pat. Nos. 5,698,083, 5,670,031, 5,128,015, and 4,999, 582, each of which is incorporated herein by reference.

Methods

The invention relates to a method of diagnosing or prognosing a clinical outcome of a subject with PKU, maple syrup urine disease, or hyperammonemia, comprising contacting a sensor, system, or test strip disclosed herein with a sample of bodily fluid from the subject, and quantifying a level of amino acid in the sample; and comparing the level of amino acid in the sample to a threshold value of what is considered normal level of amino acid level in the bodily fluid. In some embodiments, the method relates to a method of diagnosing or prognosing a clinical outcome of a subject suspected of having or having been previously diagnosed with at least one aminoacidopathy. In some embodiments, the method relates to a method of diagnosing or prognosing a clinical outcome of a subject suspected of having or having been previously diagnosed with at least one PKU, maple syrup urine disease, or hyperammonemia.

The invention relates to a method of detecting the presence or absence of amino acids in bodily fluids. the invention also relates to a method of quantifying the concentration of amino acids in bodily fluids of a subject. Quantification can occur at the point-of-care due to the quick enzymatic reaction readout caused by the generation of a detectable current within a circuit after. In some embodiments, the device or system described herein may be utilized to detect if a person has abnormally high levels of amino acids in the blood, after which an electronic message or display may then be provided to the user of the device or system or activated on a display by one or more processors that remotely or directly access one or more storage memories comprising one or more concentration values of the subject. In some embodiments, multiple concentration values may be obtained either simultaneously or in series, compared or analyzed by the one or more processors operably connected to the device or system disclosed herein. In some embodiments, multiple concentration values of a subject over a time period may be compared or analyzed by the one or more processors operably connected to the device or system disclosed herein, after which a message comprising the concentration value and/or threshold values are displayed. In some embodiments, the message optionally includes a signal indicating that the subject should seek medical treatment or alter diet to control amino acid levels in the subject.

In some embodiments, the disclosure relates to a computer-implemented method of quantifying amino acid concentration in a sample.

In some embodiments, the disclosure relates to a system comprising a processor that performs a computer-implemented method of quantifying amino acid concentration in a sample of a subject. In some embodiments, the system comprises a processor optionally located at a remote location and accessible by internet connection, operably connected to a computer storage memory that stores subject's concentration values over time. In some embodiments, the subject of the subject' healthcare provider may accesses the internet to communicate with a server linked to the computer storage memory. Subject data reports may be generated and obtained by the subject after initiating a retrieve command through the processor. In some embodiments, the system comprises a computer program-product that performs a function convert current signals generated by a biosensor to concentration of a particular amino acid in a sample. In some embodiments, the disclosure relates to a system including at least one processor and a computer readable memory, said computer readable memory having stored thereon program code for quantifying amino acid concentration in a sample of bodily fluid comprising: means for storing data associated with a subject; means for, responsive to receiving a level of current response from a biosensor or its computer storage memory, presenting a concentration value to a user as part of a user interface. In some embodiments, the user is the subject or healthcare provider of the subject. In some embodiments, the disclosure relates to a system that comprises at least one processor, a program storage, such as memory, for storing program code executable on the processor, and one or more input/output devices and/or interfaces, such as data communication and/or peripheral devices and/or interfaces. In some embodiments, the user device and computer system or systems are communicably connected by a data communication network, such as a Local Area Network (LAN), the Internet, or the like, which may also be connected to a number of other client and/or server computer systems. The user device and client and/or server computer systems may further include appropriate operating system software.

The present invention relates generally to definition and/or use of concentration values that characterize a subject's modification of behavior. in some embodiments, the concentration values corresponding to the concentration of amino acids in a sample of bodily fluid may characterize the degree to which a subject is advised to modify a diet or seek medical treatment.

In some embodiments, the present invention provides biosensors or test strips for use in diagnostic assays. In some embodiments the biosensor and/or test strips are provided as part of a diagnostic or detection kit. In certain embodiments, kits for use in accordance with the present invention may include one or more reference samples; instructions (e.g., for processing samples, for performing tests, for interpreting results, etc.); media; and/or other reagents necessary for performing tests.

The invention provides a test strip comprising: a solid support and a plurality of electrodes, wherein at least one electrode comprises a hydrogel disclosed herein. In some embodiments, the solid support is a slide optionally coated with a polymer. In some embodiments, the solid support is coated with a polymer. In some embodiments, the polymer is polyacrylamide. In some embodiments, the solid support is a material chosen from: polysterene (TCPS), glass, quarts, quartz glass, poly(ethylene terephthalate) (PET), polyethylene, polyvinyl difluoride (PVDF), polydimethylsiloxane (PDMS), polytetrafluoroethylene (PTFE), polymethylmethacrylate (PMMA), polycarbonate, polyolefin, ethylene vinyl acetate, polypropylene, polysulfone, polytetrafluoroethylene, silicones, poly(meth)acrylic acid, polyamides, polyvinyl chloride, polyvinylphenol, and copolymers and mixtures thereof. In some embodiments, the test strip is a paper product. In some embodiments, the at least one electrode is attached to the solid support.

According to some embodiments, the invention provides a software component or other non-transitory computer program product that is encoded on a computer-readable storage medium, and which optionally includes instructions (such as a programmed script or the like) that, when executed, cause operations related to the calculation of amino acid concentration values. In some embodiments, the computer program product is encoded on a computer-readable storage medium that, when executed: quantifies one or more amino acid concentration values; normalizes the one or more amino acid concentration values over a control set of data; creates an amino acid profile or signature of a subject; and displays the profile or signature to a user of the computer program product. In some embodiments, the computer program product is encoded on a computer-readable storage medium that, when executed: calculates one or more amino acid concentration values, normalizes the one or more amino acid concentration values, and creates an amino acid signature, wherein the computer program product optionally displays the amino acid signature and/or one or more amino acid concentration values on a display operated by a user. In some embodiments, the invention relates to a non-transitory computer program product encoded on a computer-readable storage medium comprising instructions for: quantifying one or more amino acid concentration values; and displaying the one or more amino acid concentration values to a user of the computer program product.

In some embodiments, the step of calculating one or more amino acid concentration values comprises quantifying an average and standard deviation of counts on replicate trials of contacting the device or test strip with one or more samples of bodily fluids.

In some embodiments, the one or more hydrogel coated electrodes are attached to a solid phase support. In some embodiments, a solid phase support comprises any solid or semi-solid surface. In some embodiments, a solid phase comprises any traditional laboratory material for growing or maintaining cells in culture including petri dishes, beakers, flasks, test tubes, microtitre plates, and/or culture slides. In some embodiments, a solid phase comprises a glass slide, a plastic slide, a paper test strip, or combination thereof.

In some embodiments, the one or more hydrogel coated electrodes are attached to discrete addressable sites on a solid phase support. In some embodiments, a solid phase comprises polyamides, polyesters, polystyrene, polypropylene, polyacrylates, polyvinyl compounds (e.g. polyvinylchloride), polycarbonate, polytetrafluoroethylene (PTFE), nitrocellulose, cotton, polyglycolic acid (PGA), cellulose, dextran, gelatin, glass, fluoropolymers, fluorinated ethylene propylene, polyvinylidene, polydimethylsiloxane, polystyrene, silicon substrates (such as fused silica, polysilicon, or single silicon crystals) or combinations thereof.

In some embodiments, the invention relates to a catalogue of medical records relating to a subject comprising test results from the one or plurality of methods described herein. Such catalogue, in some embodiments, being stored on a computer readable medium being accessible remotely through a wireless internet connection.

As described above, certain embodiments of the present invention may be used to distinguish between samples of bodily fluid obtained from a subject who does or is suspected of having an aminoacidopathy and a subject who does not have a metabolic disease. This system is potentially useful, for example, when testing blood samples of a subject to determine whether disease is present. Diagnosing a patient using one or more amino acid concentration values would include, for example, comparing one or more amino acid concentration values of a sample from a subject with the measured reference values or threshold values of a subject.

Kits

In some embodiments, kits in accordance with the present disclosure may be used to quantify amino acid concentration is samples of bodily fluid.

The invention further provides for a kit comprising one or a plurality of containers that comprise one or a plurality of the polypeptides or fragments disclosed herein. In some embodiments, the kit comprises a test strip and/or a biosensor comprising a test strip, or any animal-based derivative of serum that enhances the culture or proliferation of cells. In some embodiments, the kit comprises: a biosensor disclosed herein, any test strip disclosed herein, and a computer program product disclosed herein optionally comprising instructions to perform any one or more steps of any method disclosed herein. In some embodiments, the kit does not comprise cell media. In some embodiments, the kit comprises a solid support embedded with at least one electrode disclosed herein. In some embodiments, the kit comprises a device to affix a hydrogel to a solid support.

The kit may contain two or more containers, packs, or dispensers together with instructions for preparation of an array. In some embodiments, the kit comprises at least one container comprising the biosensor or system described herein and a second container comprising a means for maintenance, use, and/or storage of the biosensor such as storage buffer. In some embodiments, the kit comprises a composition comprising any polypeptide disclosed herein in solution or lyophilized or dried and accompanied by a rehydration mixture. In some embodiments, the polypeptides and rehydration mixture may be in one or more additional containers.

The compositions included in the kit may be supplied in containers of any sort such that the shelf-life of the different components are preserved, and are not adsorbed or altered by the materials of the container. For example, suitable containers include simple bottles that may be fabricated from glass, organic polymers, such as polycarbonate, polystyrene, polypropylene, polyethylene, ceramic, metal or any other material typically employed to hold reagents or food; envelopes, that may consist of foil-lined interiors, such as aluminum or an alloy. Other containers include test tubes, vials, flasks, and syringes. The containers may have two compartments that are separated by a readily removable membrane that upon removal permits the components of the compositions to mix. Removable membranes may be glass, plastic, rubber, or other inert material.

Kits may also be supplied with instructional materials. Instructions may be printed on paper or other substrates, and/or may be supplied as an electronic-readable medium, such as a floppy disc, CD-ROM, DVD-ROM, zip disc, videotape, audio tape, or other readable memory storage device. Detailed instructions may not be physically associated with the kit; instead, a user may be directed to an internet web site specified by the manufacturer or distributor of the kit, or supplied as electronic mail.

The invention also provides a kit comprising: a biosensor comprising: a solid support and a plurality of electrodes, wherein at least one electrode comprises a hydrogel disclosed herein. in some embodiments, the hydrogel comprises an immobilized metabolic enzyme or a functional fragment thereof; and optionally comprising a. In some embodiments, the kit further comprises at least one of the following: a sample, and a set of instructions, optionally accessible remotely through an electronic medium.

FIG. 1 depicts a biosensor 10 in accordance with the present invention. Biosensor 10 includes a display 75 formed visible to a user through a outer casing 50. A test strip (optionally removable) 100 from the device 10 comprises a first (working) electrode 300 and a second (counter) electrode 400. The test strip (in this embodiment a electrically conductive surface) also comprises a reference electrode (positioned between the first 300 and second 400 electrode). When in use, a user can contact a sample of bodily fluid 200 to the test strip 100 of the biosensor 10. Due to the hydrogel that coats at least a portion of the working electrode, amino acid analytes/substrates within the sample 200 can be detected at the working electrode surface by simple diffusion to the at least one electrically conductive surface.

Any and all journal articles, patent applications, issued patents, or other cited references disclosed herein are incorporated by reference in their respective entireties.

EXAMPLES

Example 1

Glutamate Dehydrogenase

Two biosensors were made using two different glutamate dehydrogenases, both of which were purchased from a commercial vendor, Sigma-Aldrich®. L-Glutamic Dehydrogenase (NADP) from *Proteus* sp. (CAS 9029-11-2) was hydrated in 1×PBS prior to use. L-Glutamic Dehydrogenase from bovine liver, Type III (CAS Number 9029-12-3, lyophilized powder, >20 units/mg protein was hydrated in 1×PBS prior to use.

Example 2

Glutamate Sensor Fabrication Hydrogel

Figure 5:
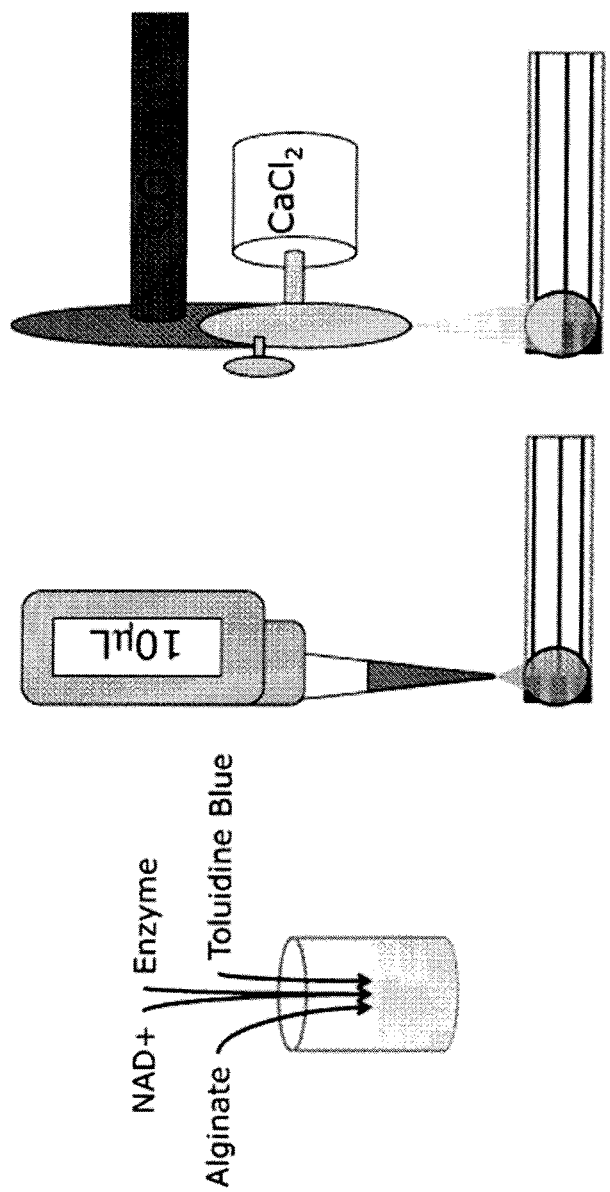
FIG. 5 depicts a general schematic of how hydrogel slurry was mixed and deposited to create the electrode. Far left panel depicts a first step in which alginate slurry was mixed with NAD+, metabolic enzyme, and toluidine blue. Middle panel depicts the deposition of 10 microliters of the slurry onto the electrode surface. The far right panel depicts a third step of the modified electrode being sprayed with nebulized $CaCl_2$ solution in a carbon dioxide mist, which solidifies the alginate on the surface of the electrode.

To fabricate a hydrogel matrix (the schematic for which appears in FIG. 5) a 1 mL stock solution in 1× phosphate buffered saline containing the following was prepared:
   a. 40 units of glutamate dehydrogenase, where a unit reduces 1.0 µmole of α-ketoglutarate to L-glutamate per min at pH 7.3 at 25° C., in the presence of ammonium ions.
   b. 20 mL of 0.05M Toluidine Blue
   c. 5 mM β-Nicotinamide adenine dinucleotide, reduced dipotassium salt
   d. 1% weight/volume sodium alginate from brown algae 10 mL of the pre-gel solution was spread onto a three electrode screen printed carbon electrode. The electrode contains both a counter and working electrode as well as a silver/silver chloride reference electrode. The working electrode acts as the sensing electrode. The pre-gel solution on the electrode were then sprayed with a 0.1M $CaCl_2$ solution using a Badger 200N airbrush at 7.5 psi for 1 second, depositing ~5 mL of the $CaCl_2$ solution. The gel would be allowed to cure for 30 minutes in a humid environment.

The goal of using alginate was to immobilize the enzyme, introducing greater stability to the enzyme and to the electrochemical sensor. The negatively charged nature alginate acts to inhibit the diffusion of uric acid and ascorbic acid. Alginate solution containing the enzyme, cofactor and mediator was deposited onto the electrode. 10 microliters of this solution was used. The alginate concentration would range from 1-3% weight/volume. The hydrogel pre-solution would then have CaCl2 solution nebulized onto its surface causes the system to form a gel. The concentration of CaCl2 ranged from 100-200 mM. Volumes of $CaCl_2$ deposited ranged from 2.5-10 microliters. The alginate hydrogel was optimized to allow the diffusion of the analyte and electrically active NADH but not uric acid. To test optimization NADH solution were applied to the alginate modified electrode to determine whether the NADH diffusion was inhibited by the hydrogel.

Figure 21:
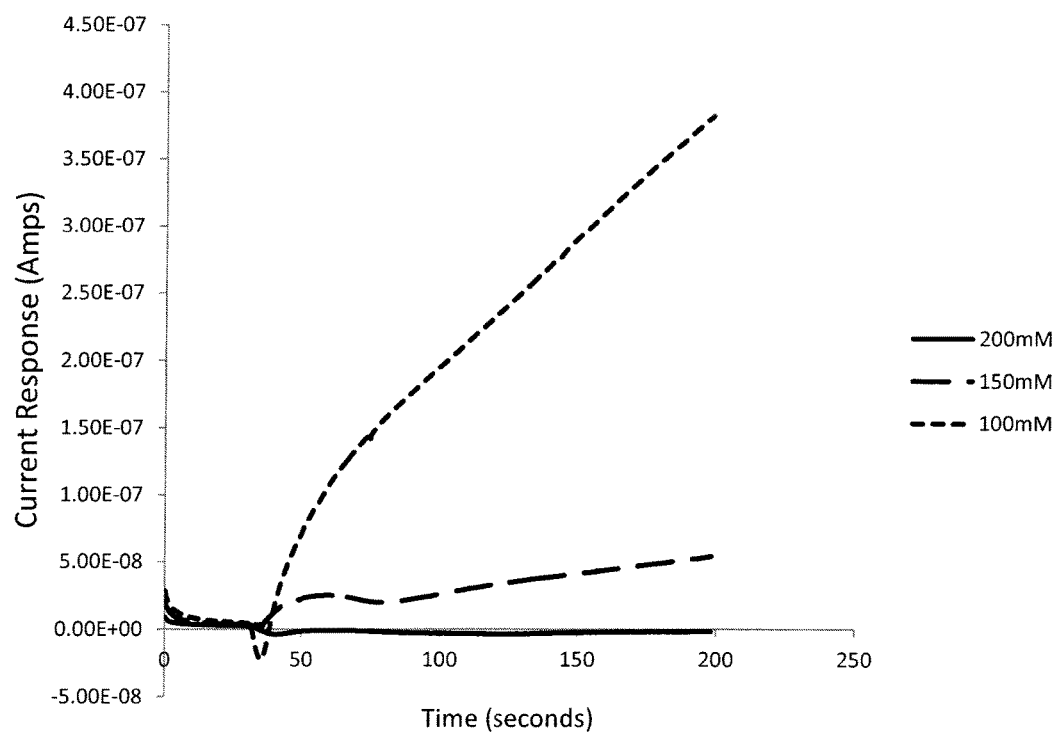
FIG. 21 depicts the effects of current response as a function of blood samples to hydrogel capted electrodes comprising alginate and varying concentrations of $CaCl_2$. Treatment of an electrode with a 1% weight to volume ratio of alginate solution in combination with 100 micromolar $CaCl_2$ allowed for greatly improved signals of glutamate concentrations in the sample.
Figure 22:
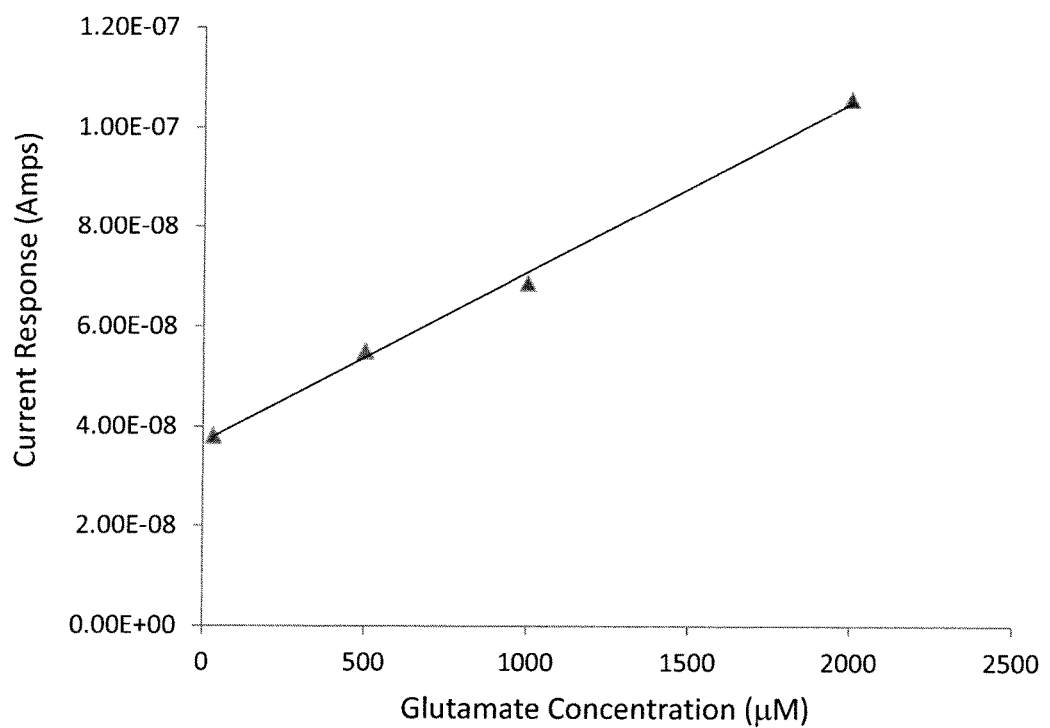
FIG. 22 depicts the current measurements of the biosensor used in FIG. 21 being linearly proportional to the concentrations of glutamate in a given sample.

As seen in FIG. 21, the hydrogel was formed using CaCl2 concentrations of 100, 150 and 200 mM. 200 mM prevented any type of electrochemical response. 150 mM severely inhibited the electrochemical response while about 100 mM allowed a very large electrochemical response. This was performed after contacting the electrode with an about 1% Alginate solution. The data is not shown by concentration of alginate higher than 1% which also prevented or severely inhibited the electrochemical response. The alginate modified electrodes were able to detect a range of glutamate concentrations in plasma as seen in FIG. 22.

Figure 23:
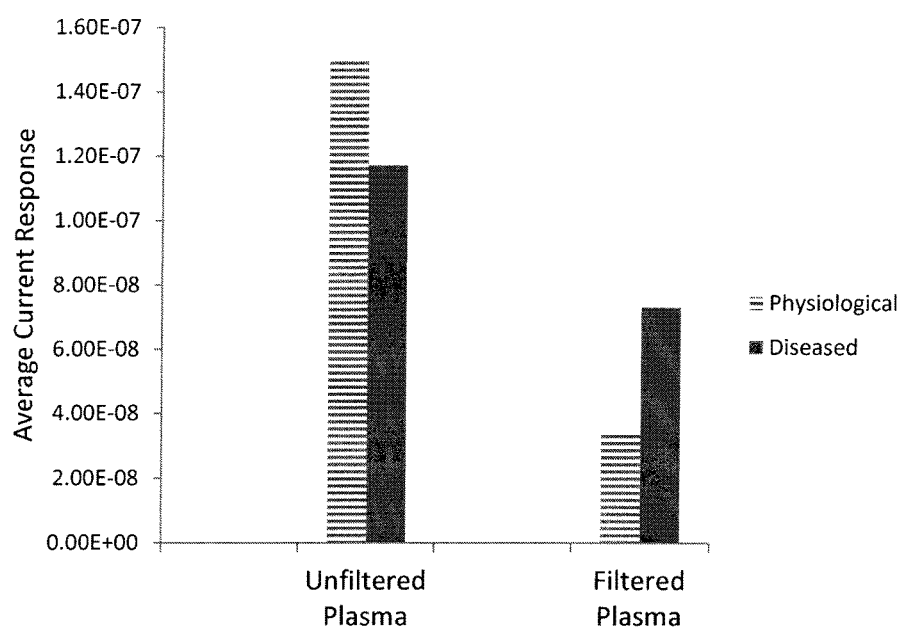
FIG. 23 depicts current measurements of the biosensor used in FIG. 21 (right hand side graph) being tested against a biosensor comprising a hydrogel without alginate (left hand side bar graphs). The data show that the biosensors comprising hydrogel with alginate concentrations at about 1% more create more highly distinguishable current measurements as between blood samples taken from healthy subjects and blood samples taken from subjects diagnosed as having an aminoacidopathy related to glutamate metabolism.

FIG. 23 exhibits the difference between electrochemical responses to both diseases (2000 mM) and physiological (35 mM) levels of glutamate in plasma. In each case either the alginate "filter" is present or not. As seen the amount of interference is dramatically reduced by the presence of the alginate. A large response is seen for higher levels of glutamate in the case where the alginate is present. When the alginate is not present a large degree of interference causes the two signals to be difficult to distinguish.

Example 3

Glutamate Sensor Methods

Figure 3:
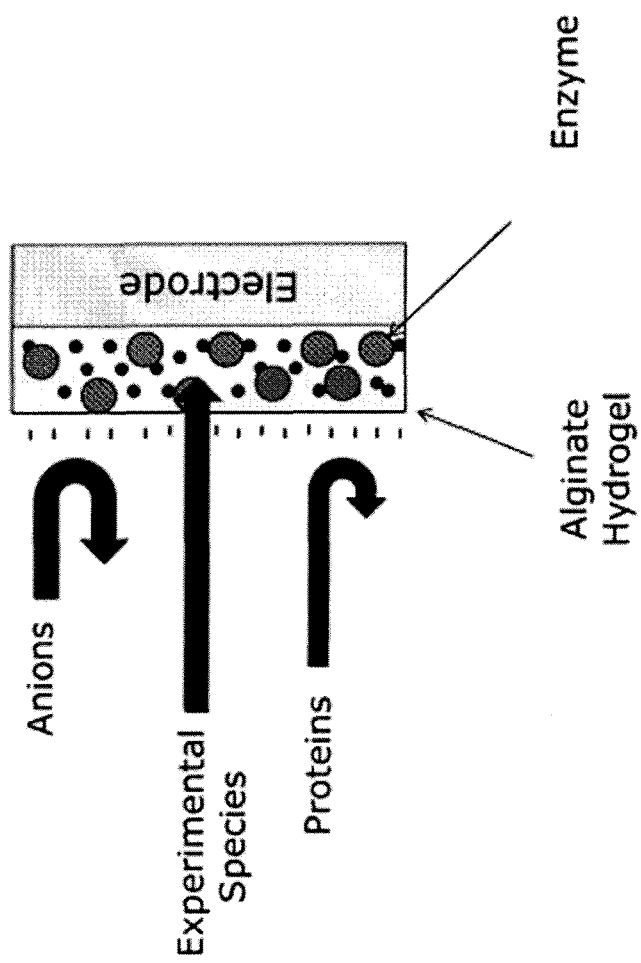
FIG. 3 depicts a simplified schematic of an embodiment wherein the conductive electrode surface is coated with a hydrogel comprising alginate and at least one metabolic enzyme. Negative charge of the electrode surface depicted by "−" signs repels anions in the bodily fluid. Negative charge and alginate gel do not allow high molecular weight proteins from contacting the electrode. Experimental species such as amino acid substrates can access the electrode through diffusion across the hydrogel. The repulsion and steric hindrance of anionic molecules and high molecular weight protein reduces signal interferences propagated in the system.
Figure 4:
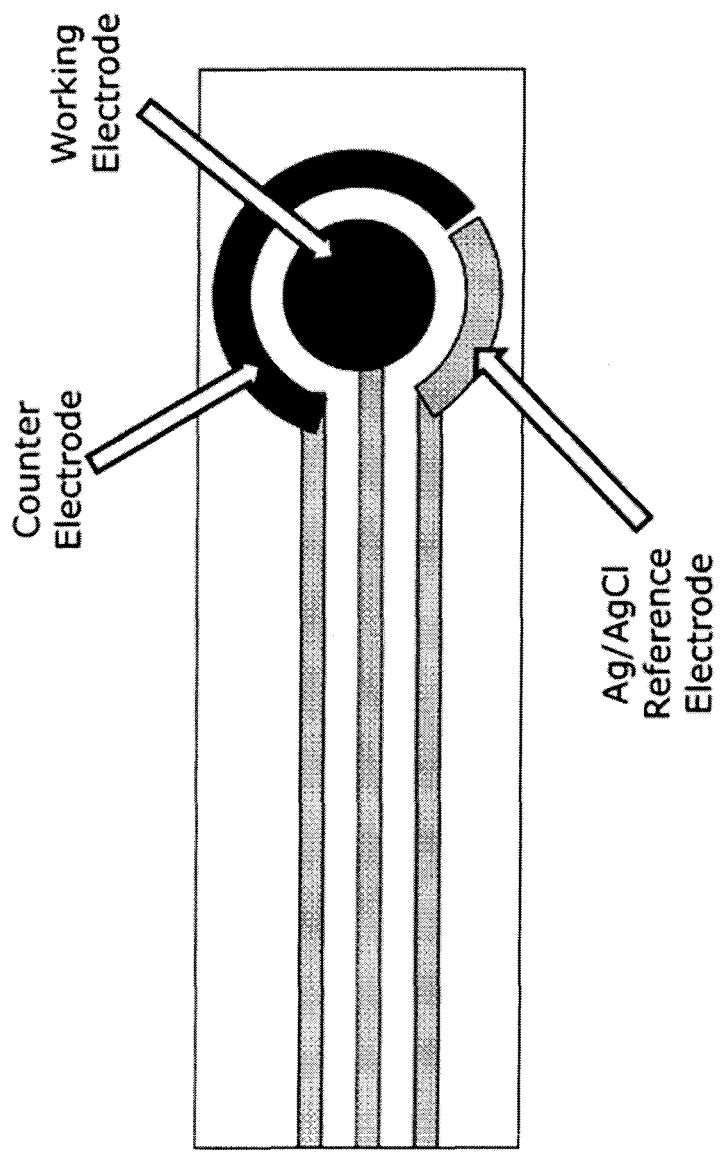
FIG. 4 depicts a basic schematic of the components of the biosensor electrode ran in parallel with a counter electrode (or second electrode). The surface of the reference electrode is not functionalized with hydrogel or other components for sufficient control signals.
Figure 6:
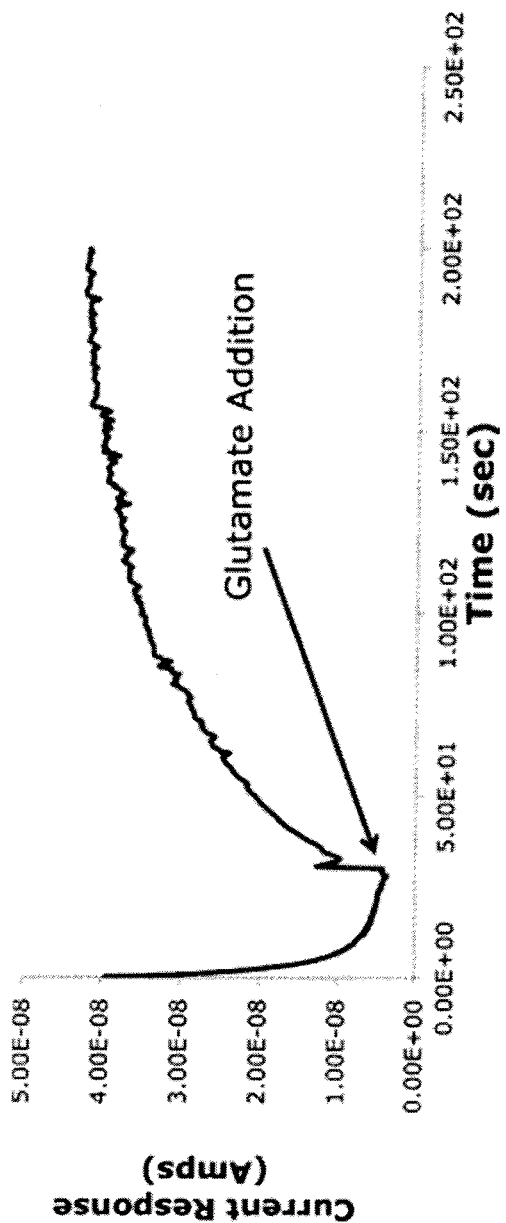
FIG. 6 depicts a measurement obtained from a biosensor comprising immobilized glutamate dehydrogenase. The graph shows how, over time, current response on the modified electrode increases as free glutamate amino acid in solution is contacted with the electrode.
Figure 7:
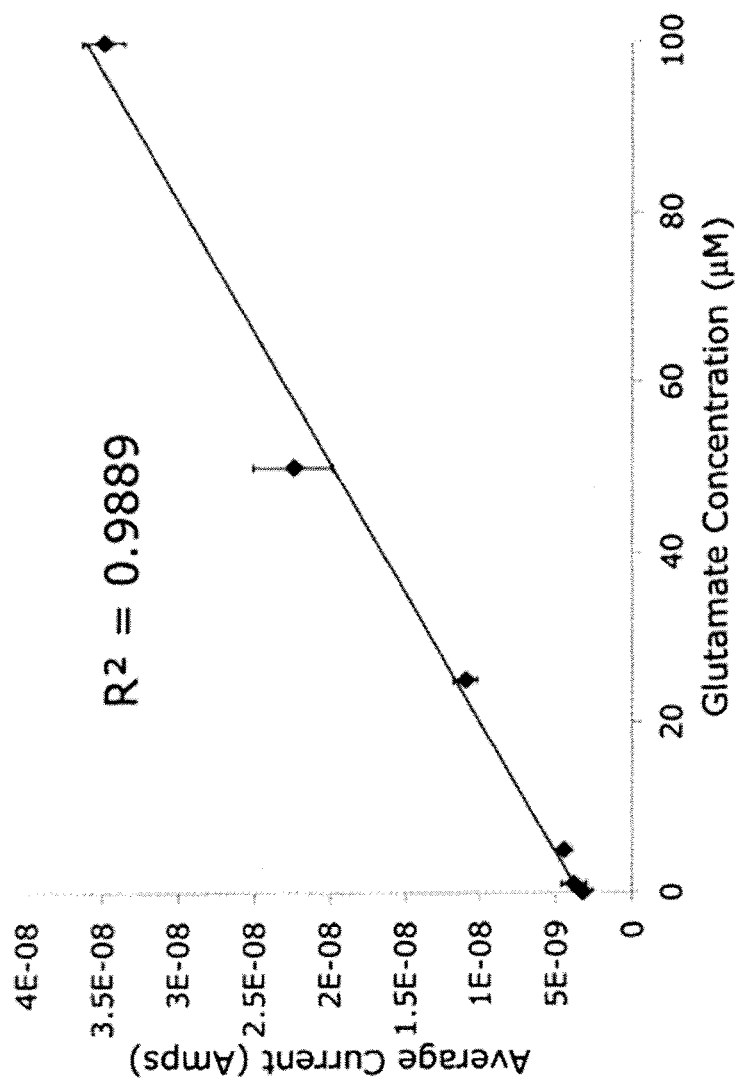
FIG. 7 depicts a graph using data collected on the biosensor utilized in FIG. 6. The graph shows that the average current measurements collected using various concentrations of glutamate resulted in a linear relationship between concentration and signal. These data suggest that a particular current measurement positively correlates to a particular amino acid concentration.

To test this concept an analogous experimental set up was performed with glutamate dehydrogenase for the detection of glutamatein solution using the setup disclosed in FIGS. 3 and 4. A three electrode system comprised of carbon screen-printed electrodes and a silver/silver chloride (FIG. 4) reference was exposed to a solution of glutamate dehydrogenase and NAD+. Various concentrations of glutamate were then added to the solution and the current generated was measured. FIG. 6 depicts the addition of glutamate in a solution of 100 µM and subsequent detection of the glutamate in a sample over time. This current response as well as the results for varying concentrations were then correlated to the glutamate concentration. FIG. 7 shows the results of these experiments. The glutamate could be detected over a range of 1 µM to 100 µM with high degree of correlation between the detected current and the concentration of amino acid in the sample. The results of FIG. 7 show that the average current detected over time linearly relates to the concentration of amino acid in solution.

FIG. 6: Upon addition of the analyte containing glutamate the current exponentially increases due to the redox reaction performed by the enzyme. The current was measured using amperometry.

FIG. 7: Using current values generated by amperometry, a standard curve was developed correlating glutamate concentration and current response. Concentrations ranging from 0-100 µM were tested with a strong degree of linearity and r-squared value of 0.98.

Figure 8:
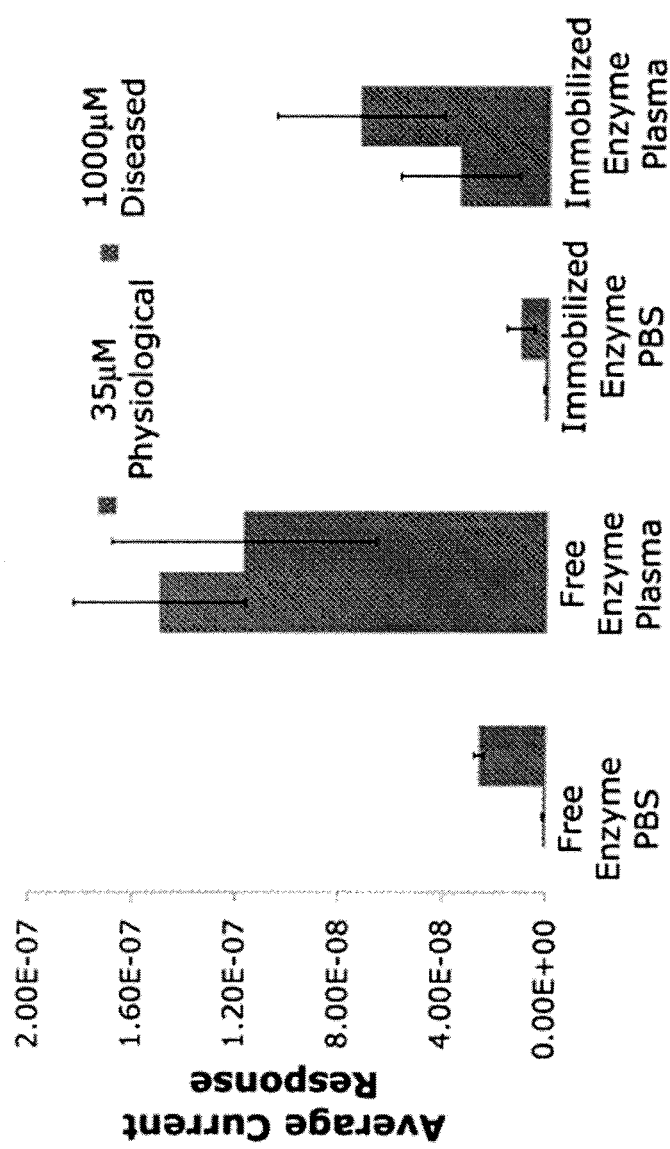
FIG. 8 depicts a set of current measurements using two concentrations of glutamate contacting the biosensor with two variables of experimentation. The data show that glutamate in phosphate buffered saline solution provided very weak current signals/strength as compared to the glutamate signal strength detected in plasma fluid. The results also show that immobilized enzyme more greatly differentiates signal to noise ratio as compared to glutamate dehydrogenase not immobilized to the surface of the hydrogel.

FIG. 8: This figure demonstrates the effectiveness of the alginate hydrogel in reducing the inherit electrical interference in blood. Enzyme in solution on the electrode produced linear responses between low and high concentrations of glutamate. Performing the reaction in absence of the alginate filter in plasma gave a large degree of interference and linearity was lost. Introducing the alginate filter allowed for linear responses for high and low concentrations of glutamate even when exposed to plasma.

Figure 9:
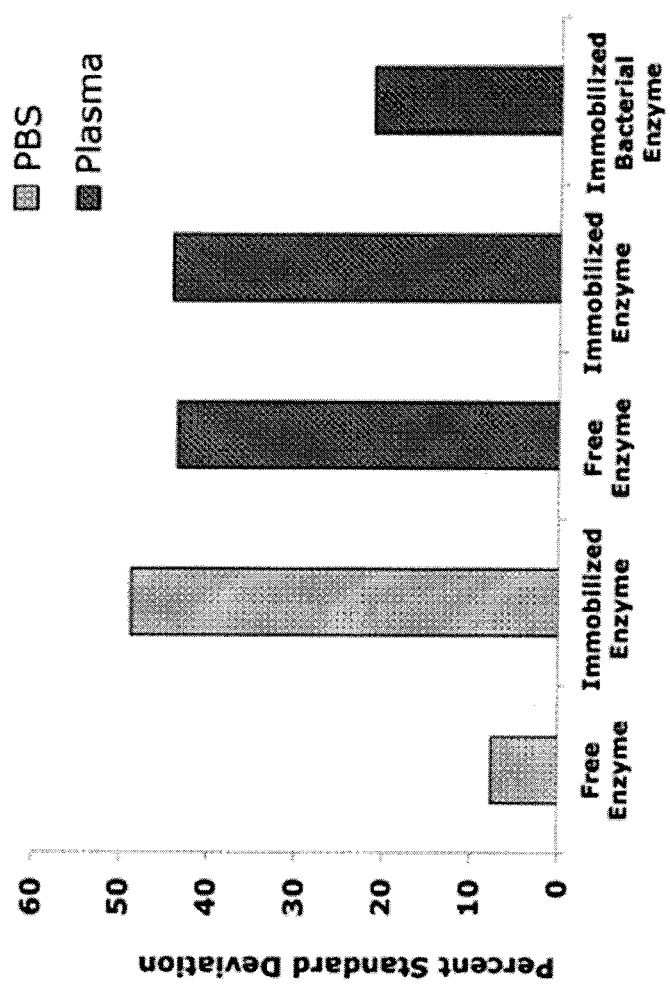
FIG. 9 depicts an experiment performed with the glutamate dehydrogenase biosensor demonstrating how the error in signal, accounted for by standard deviation calculation, is reduced by utilizing immobilized bacterial glutamate dehydrogenase as compared to free an immobilized versions of glutamate dehydrogenase derived from bovine liver.

FIG. 9: Use of a bacterial form of the glutamate dehydrogenase cut error in measurements in half. This is due to the bovine form of glutamate dehydrogenase forming aggregates in solution unlike the bacterial form of the enzyme. This leads to more consistent construction of enzyme electrodes with the bacterial form of the enzyme.

Figure 10:
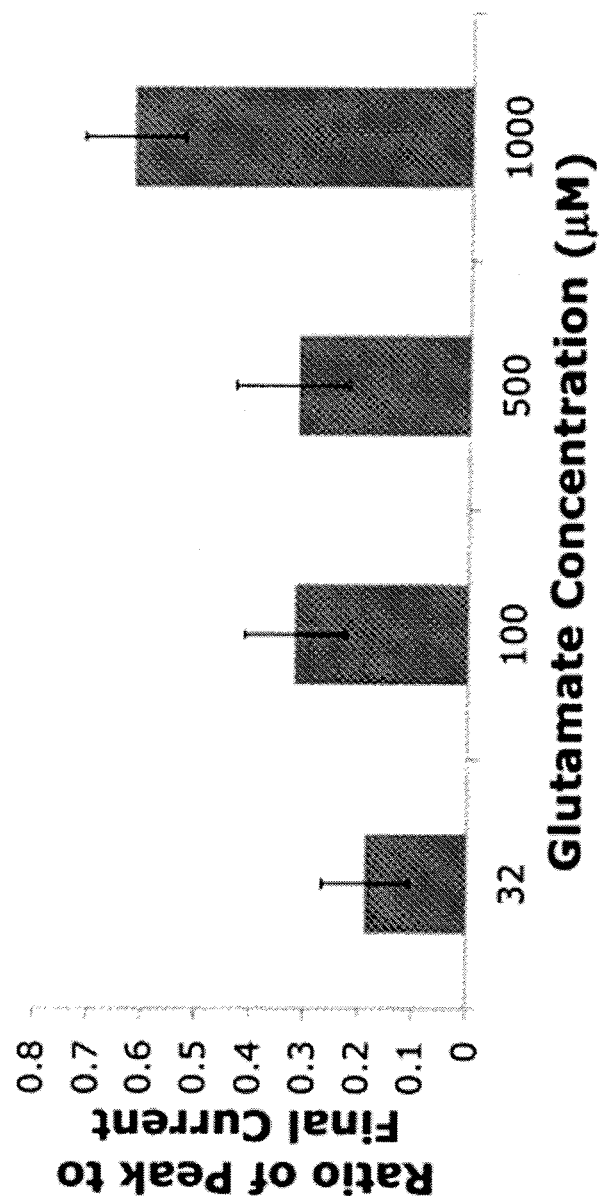
FIG. 10 depicts the ratio of peak to final current in relation to variations of glutamate concentration in the micromolar levels.
Figure 11:
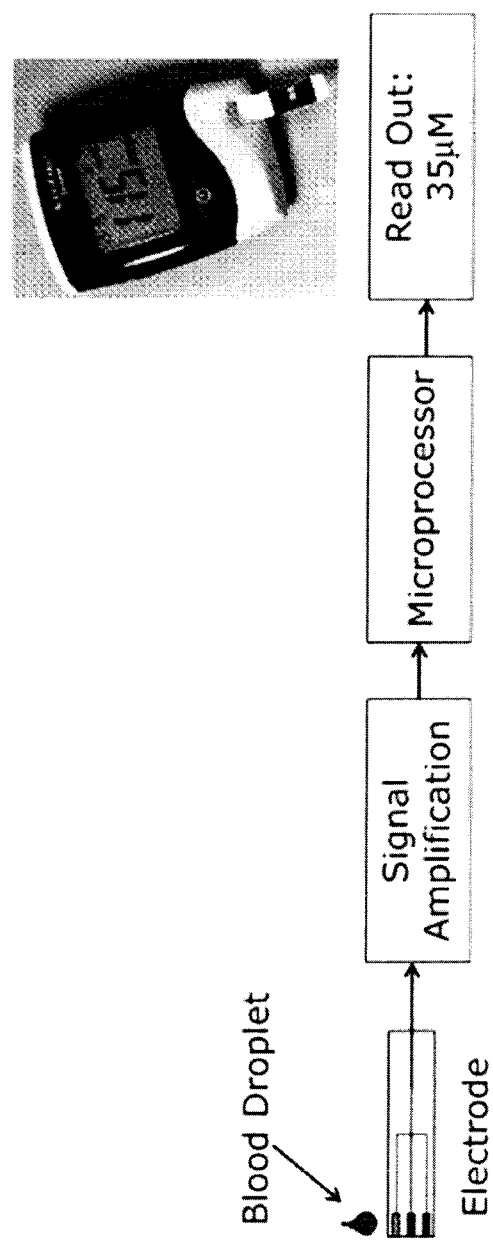
FIG. 11 depicts a general flow diagram of the steps elated to how the current signal detected is amplified to a readout value consistent with the concentration of amino acid in a particular blood sample.
Figure 12:
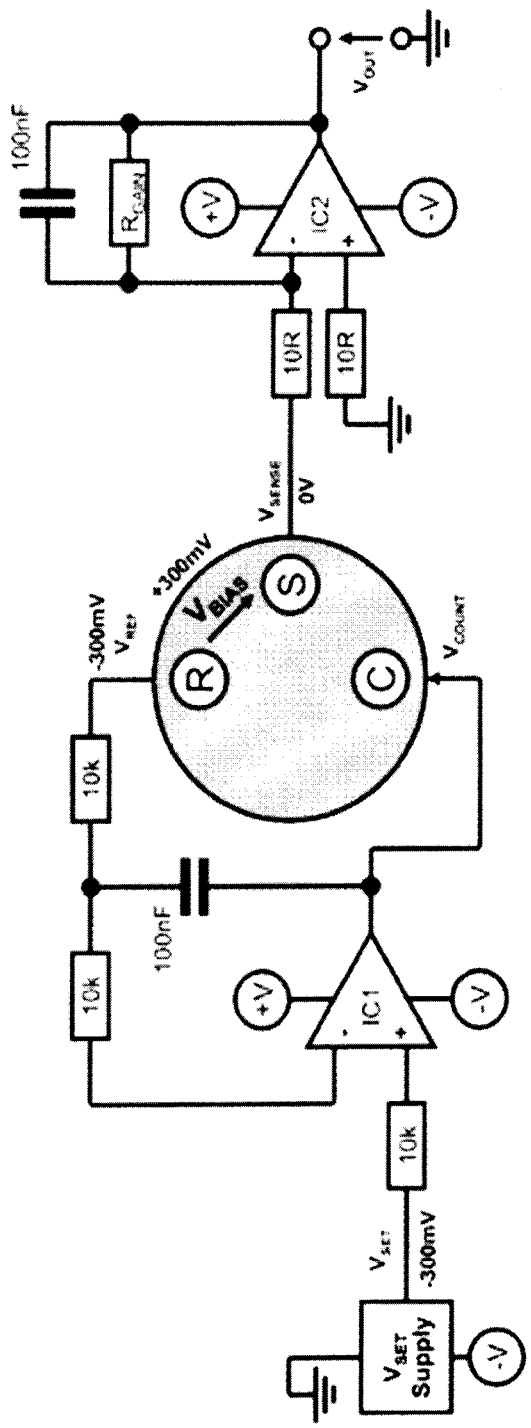
FIG. 12 depicts a simple circuit diagram for how current signals are obtained and amplified within a device.
Figure 13:
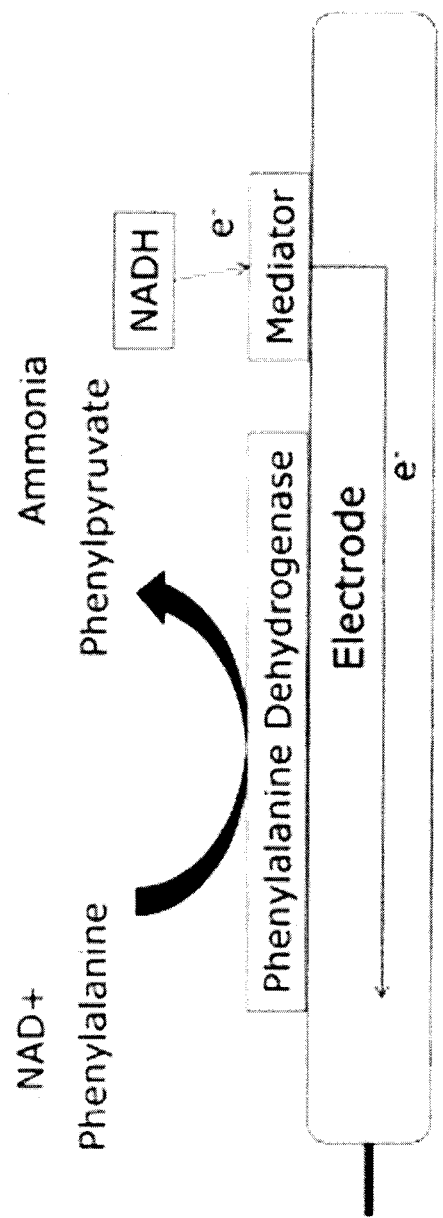
FIG. 13 depicts a general schematic of an embodiment in which phenylalanine concentrations can be detected by replacing glutamate dehydrogenase with phenylalanine dehydrogenase, and exposing the electrode to phenylalanine. Similar to the embodiments utilizing immobilized glutamate dehydrogenase, the biosensor depicted in this embodiment creates electron (e−) current by reduction agents NAD+ transporting electron products that result from enzymatic reaction to an electron mediator to the electrically conductive surface of the electrode.

FIG. 10: Using the bacterial form of glutamate dehydrogenase allowed for linear detection of glutamate in plasma in a concentration range of 35-1000 µM, representing both normal and diseased levels of the amino acid. The alginate filter reduced interference to the point where 35 and 1000 µM were statistically significant from one another.

Example 4

Phenylalanine Dehydrogenase Cloning

To address shortcomings of long day-long wait times for diagnosing PKU, a sensor analogous to a blood glucometer would greatly improve detection time and quality of life for the patient. Development of this type of sensor for ammonia and various amino acids is being currently undergoing. The first metabolite to be investigated will be phenylalanine High serum levels of phenylalanine are generally associated with the aminoacidopathy, phenylketonuria. To determine concentrations of phenylalanine an enzyme based amperornetric electrochemical sensor will be employed. The specific enzyme that will be examined is phenylalanine dehydrogenase.

Figure 18:
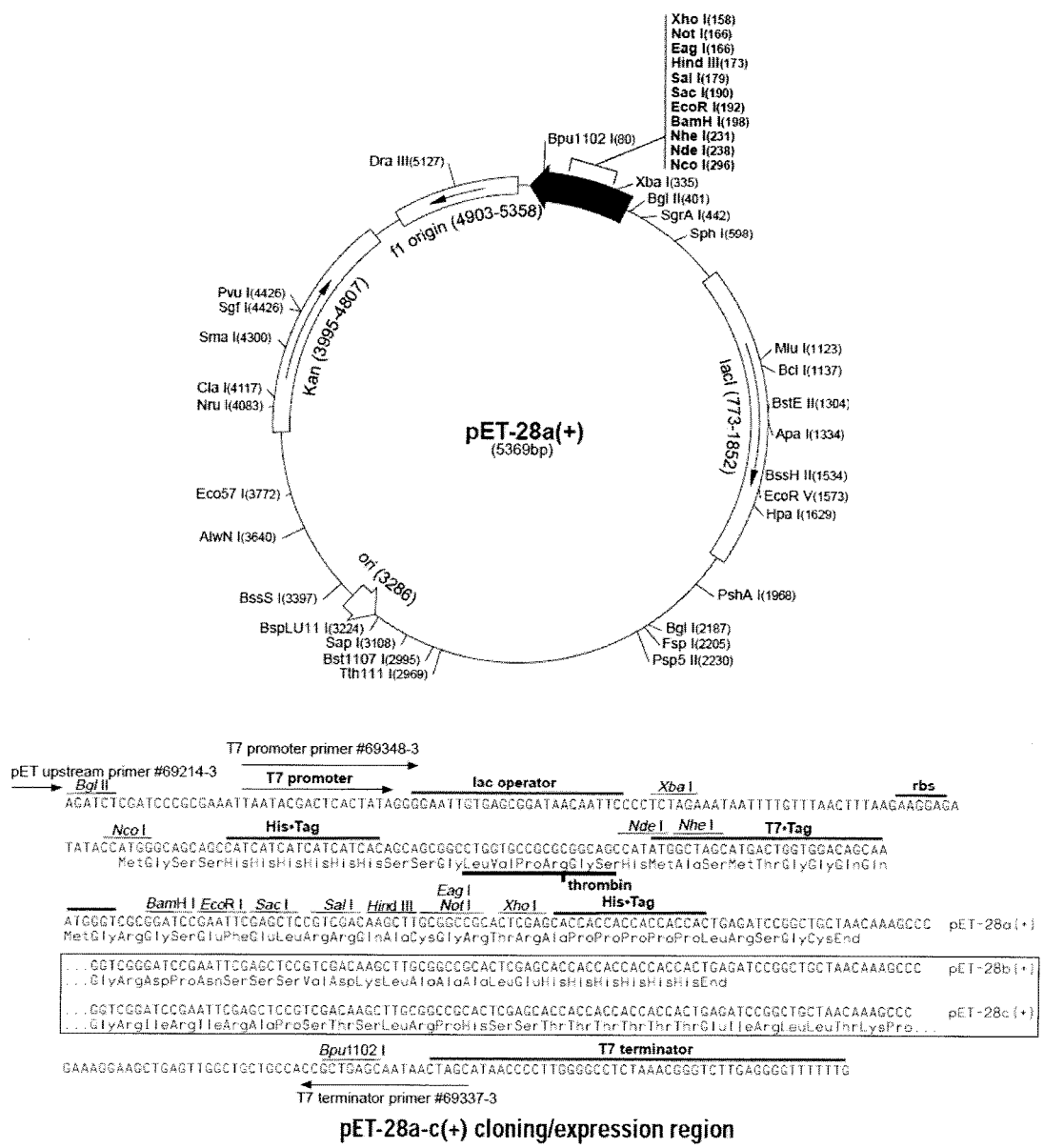
FIG. 18 depicts a restriction map of plasmid pET28a used to recombinantly produce a subcloned version of the metabolic enzyme.
Figure 19:
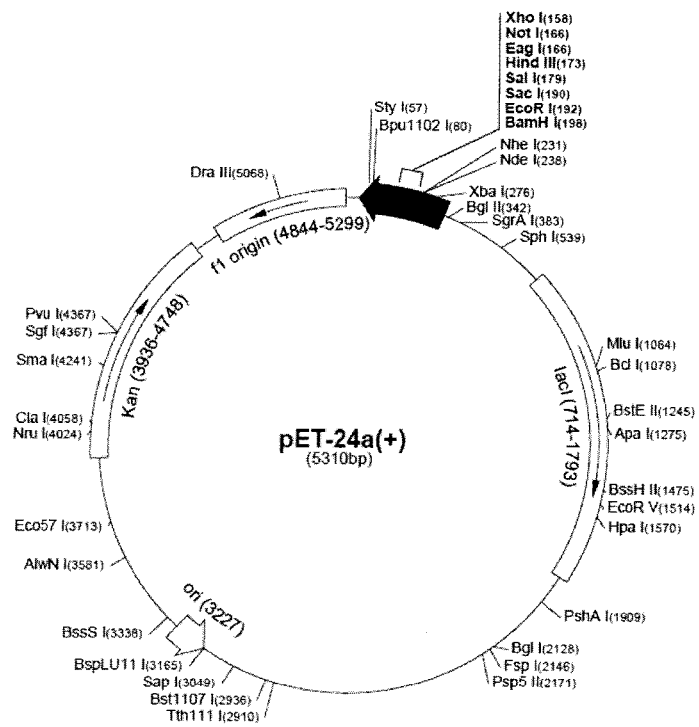
FIG. 19 depicts a restriction map of plasmid pET24a used to recombinantly produce a subcloned version of the metabolic enzyme.
Figure 20:
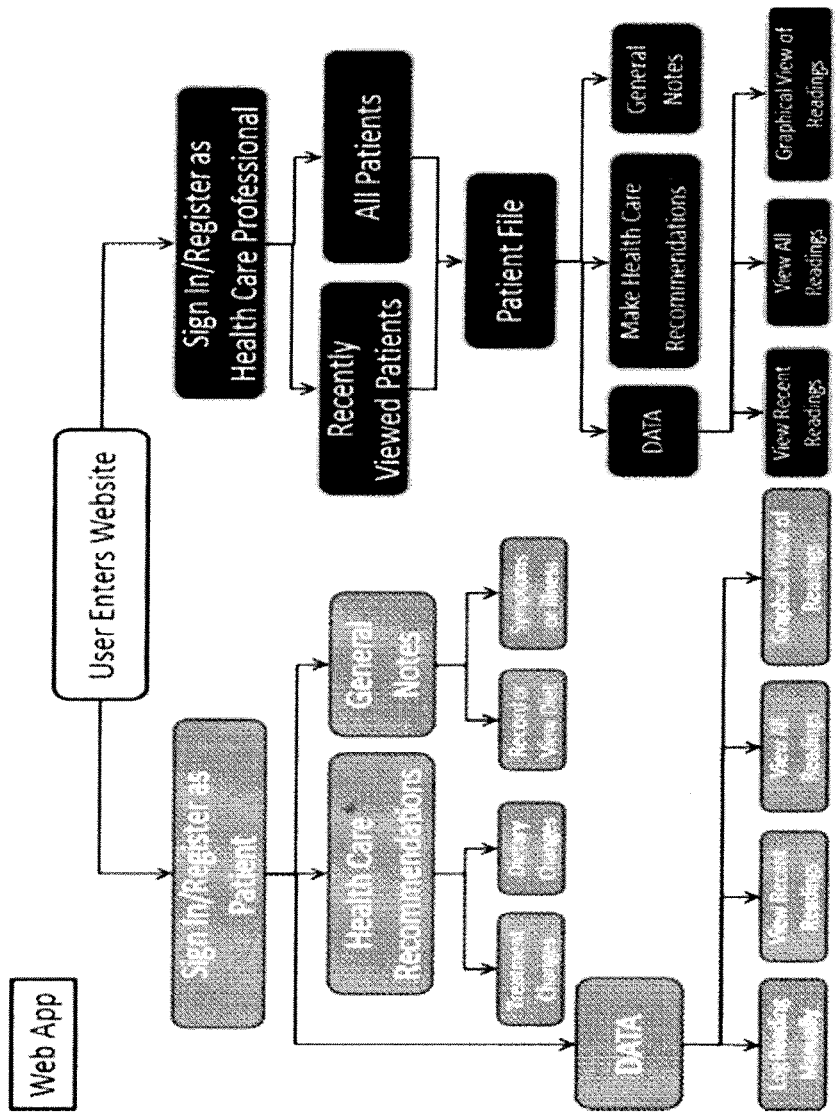
FIG. 20 depicts an electronic interface designed in hierarchical pattern of webpage maps for internet content in which patient information is compiled, stored, and can be accessed by the patient (left hand side of figure) or a healthcare provider (right hand side of diagram).

The gene coding for the phenylalanine dehydrogenase (PheDH) from *Geobacillus thermoglucosidiasius* C56-YS93 was cloned and the protein will be expressed using a bacterial cloning/expression system as shown in FIGS. 18 and 19. Three different versions of the enzyme were generated: N-His tag, C-His tag and No tag by using custom designed primers and different expression vectors (pET24a and pET28a).

Briefly, DNA from *Geobacillus thermoglucosidiasius* was isolated and the PheDH gene was amplified by PCR using the following primers:

```
Foward
                                        (SEQ ID NO: 3)
5'-TGTGCTAGCATGAATACCGTTACCAATCAGTGGAAAGC-3'

Reverse
                                        (SEQ ID NO: 4)
5'-CTCGAGTCATTACCGGCGGATATCCCACTTCG-3'
```

Forward primer introduces a NheI restriction site and the reverse primer introduces two extra STOP codons along with a XhoI restriction site. Amplification product size was determined by agarose electrophoresis. The DNA sequence cloned from the isolated genome sequence encodes the following amino acid sequence that is the PheDH protein from *Geobacillus thermoglucosidiasius*:

```
                                        (SEQ ID NO: 1)
MNTVTNQWKAVDIFTQIRDHEQVVFCNDKNTGLKAIIAIHDTTL

GPALGGCRMYPYATVEDALFDVLRLSKGMTYKCLAADVDFGGGKAVIIGD

PHKDKTPELFRAFGQFVESLNGRFYTGTDMGTTPDDFVHAMKETNCIVGV

PEEYGGSGDSSVPTALGVIYGIQATNKVIWGSDELHGKTYAIQGLGKVGR

KVAERLLKEGADLYVCDIHPTAIEAIVSYAKKLGANVKVVQGTEIYRTDA

-continued
DIFVPCAFGNVVNDNTIHVLKVKAIVGSANNQLLDVRHGQLLKEKGILYA

PDYIVNAGGLIQVADELYGLNKERVLQKTKAIYSTLLHIYSRAEADHITT

IEAANRFCEERLQQRSRRNDFFTHRKQPKWDIRR.
```

PCR product was purified directly from the PCR reaction mixture using the Qiagen® kit using the manufacturer's instructions and subsequently used for subcloning onto pCR-BluntII TOPO vector using the Invitrogen kit with manufacturer's instructions. Subcloning reaction was used to transform TOP10 chemically competent cells (Invitrogen®) and positive colonies were selected by resistance to the antibiotic kanamycin. The plasmids presents in the kanamycin resistant colonies were isolated using the Qiagen® kit using the manufacturer's instructions and screened for the presence of the insert in the plasmid by restriction enzymes (NheI and XhoI). Positive colonies were identified by the presence of a band corresponding to the PCR product size after digestion with the restriction enzymes. One positive colony was selected for isolation of larger amount of plasmid DNA using the Qiagen® maxiprep kit in accordance with manufacturer's instructions. For cloning of the desired gene, destination vectors (expression vectors) pET24a and pET28a (FIGS. 18 and 19) were digested at the same time as the selected positive plasmid with the restriction enzymes NheI and XhoI and the digested fragments to be used were isolated from the agarose gel in which they were separated. For cloning of the gene onto the expression vectors we used a ratio 1:3 vector to insert for the ligation reaction. Once the ligation reaction was concluded it was used directly to transform TOP10 chemically competent cells. Plasmid containing colonies were selected by resistance to the antibiotic kanamycin and positive colonies (those that had the gene inserted onto the plasmid) were screened by digestion with restriction enzymes and the resulting fragments were separated by agarose electrophoresis. On positive colony was selected for isolation of larger amount of plasmid DNA using the Qiagen® maxiprep kit in accordance with manufacturer's instructions.

Positive plasmid was introduced by transformation onto the expressing cell line Rosetta 2 commercially available from Novagen®. Protein production was induced when cells reached mid-log phase by adding a final concentration of 100 µM of IPTG. Protein was purified from inclusion bodies after induction and its activity tested by determining the amount of phenylalanine consumed after 30 minutes at 37° C. by amino acid analysis.

```
pET24a Vector Sequence
                                                    (SEQ ID NO: 5)
  1 atccggatat agttcctcct ttcagcaaaa aaccctcaa gacccgttta gaggcccaa 61 ggggttatgc tagttattgc tcagcggtgg cagcagccaa ctcagcttcc tttcgggctt 121 tgttagcagc cggatctcag tggtggtggt ggtggtgctc gagtgcggcc gcaagcttgt 181 cgacggagct cgaattcgga tcctagaggg gaattgttat ccgctcacaa ttcccctata 241 gtgagtcgta ttaatttcgc gggatcgaga tctcgatcct ctacgccgga cgcatcgtgg 301 ccggcatcac cggcgccaca ggtgcggttg ctggcgccta tatcgccgac atcaccgatg 361 gggaagatcg ggctcgccac ttcgggctca tgagcgcttg tttcggcgtg ggtatggtgg 421 caggccccgt ggccggggga ctgttgggcg ccatctcctt gcatgcacca ttccttgcgg 481 cggcggtgct caacggcctc aacctactac tgggctgctt cctaatgcag gagtcgcata 541 agggagagcg tcgagatccc ggacaccatc gaatggcgca aaacctttcg cggtatggca
```

-continued

```
 601 tgatagcgcc cggaagagag tcaattcagg gtggtgaatg tgaaaccagt aacgttatac
 661 gatgtcgcag agtatgccgg tgtctcttat cagaccgttt cccgcgtggt gaaccaggcc
 721 agccacgttt ctgcgaaaac gcgggaaaaa gtggaagcgg cgatggcgga gctgaattac
 781 attcccaacc gcgtggcaca caactggcg gcaaacagt cgttgctgat tggcgttgcc
 841 acctccagtc tggccctgca cgcgccgtcg caaattgtcg cggcgattaa atctcgcgcc
 901 gatcaactgg gtgccagcgt ggtggtgtcg atggtagaac gaagcggcgt cgaagcctgt
 961 aaagcggcgg tgcacaatct tctcgcgcaa cgcgtcagtg gctgatcat taactatccg
1021 ctggatgacc aggatgccat tgctgtggaa gctgcctgca ctaatgttcc ggcgttattt
1081 cttgatgtct ctgaccagac acccatcaac agtattattt tctcccatga agacggtacg
1141 cgactggcg tggagcatct ggtcgcattg gtcaccagc aaatcgcgct gttagcgggc
1201 ccattaagtt ctgtctcggc gcgtctgcgt ctggctggct ggcataaata tctcactcgc
1261 aatcaaattc agccgatagc ggaacgggaa ggcgactgga gtgccatgtc cggttttcaa
1321 caaaccatgc aaatgctgaa tgagggcatc gttcccactg cgatgctggt tgccaacgat
1381 cagatggcgc tgggcgcaat gcgcgccatt accgagtccg ggctgcgcgt tggtgcggat
1441 atctcggtag tgggatacga cgataccgaa gacagctcat gttatatccc gccgttaacc
1501 accatcaaac aggattttcg cctgctgggg caaaccagcg tggaccgctt gctgcaactc
1561 tctcagggcc aggcggtgaa gggcaatcag ctgttgcccg tctcactggt gaaaagaaaa
1621 accaccctgg cgcccaatac gcaaaccgcc tctccccgcg cgttggccga ttcattaatg
1681 cagctggcac gacaggtttc ccgactggaa agcgggcagt gagcgcaacg caattaatgt
1741 aagttagctc actcattagg caccgggatc tcgaccgatg cccttgagag ccttcaaccc
1801 agtcagctcc ttccggtggg cgcggggcat gactatcgtc gccgcactta tgactgtctt
1861 ctttatcatg caactcgtag gacaggtgcc ggcagcgctc tgggtcattt tcggcgagga
1921 ccgctttcgc tggagcgcga cgatgatcgg cctgtcgctt gcggtattcg gaatcttgca
1981 cgccctcgct caagccttcg tcactggtcc cgccaccaaa cgtttcggcg agaagcaggc
2041 cattatcgcc ggcatggcgg ccccacgggt gcgcatgatc gtgctcctgt cgttgaggac
2101 ccggctaggc tggcggggtt gccttactgg ttagcagaat gaatcaccga tacgcgagcg
2161 aacgtgaagc gactgctgct gcaaaacgtc tgcgacctga gcaacaacat gaatggtctt
2221 cggtttccgt gtttcgtaaa gtctggaaac gcggaagtca gcgccctgca ccattatgtt
2281 ccggatctgc atcgcaggat gctgctggct accctgtgga acacctacat ctgtattaac
2341 gaagcgctgg cattgaccct gagtgatttt tctctggtcc cgccgcatcc ataccgccag
2401 ttgtttaccc tcacaacgtt ccagtaaccg ggcatgttca tcatcagtaa cccgtatcgt
2461 gagcatcctc tctcgtttca tcggtatcat taccccatg aacagaaatc ccccttacac
2521 ggaggcatca gtgaccaaac aggaaaaaac cgcccttaac atgcccgct ttatcagaag
2581 ccagacatta acgcttctgg agaaactcaa cgagctggac gcggatgaac aggcagacat
2641 ctgtgaatcg cttcacgacc acgctgatga gctttaccgc agctgcctcg cgcgtttcgg
2701 tgatgacggt gaaaacctct gacacatgca gctcccggag acggtcacga cttgtctgta
2761 agcggatgcc gggagcagac aagcccgtca gggcgcgtca gcgggtgttg cgggtgtcg
2821 gggcgcagcc atgacccagt cacgtagcga tagcggagtg tatactggct taactatgcg
2881 gcatcagagc agattgtact gagagtgcac catatatgcg gtgtgaaata ccgcacagat
2941 gcgtaaggag aaaataccgc atcaggcgct cttccgcttc ctcgctcact gactcgctgc
3001 gctcggtcgt tcggctgcgg cgagcggtat cagctcactc aaaggcggta atacggttat
```

-continued

```
3061 ccacagaatc agggggataac gcaggaaaga acatgtgagc aaaaggccag caaaaggcca
3121 ggaaccgtaa aaaggccgcg ttgctggcgt ttttccatag gctccgcccc cctgacgagc
3181 atcacaaaaa tcgacgctca agtcagaggt ggcgaaaccc gacaggacta taaagatacc
3241 aggcgtttcc ccctggaagc tccctcgtgc gctctcctgt tccgaccctg ccgcttaccg
3301 gatacctgtc cgcctttctc ccttcgggaa gcgtggcgct ttctcatagc tcacgctgta
3361 ggtatctcag ttcggtgtag gtcgttcgct ccaagctggg ctgtgtgcac gaaccccccg
3421 ttcagcccga ccgctgcgcc ttatccggta actatcgtct tgagtccaac ccggtaagac
3481 acgacttatc gccactggca gcagccactg gtaacaggat tagcagagcg aggtatgtag
3541 gcggtgctac agagttcttg aagtggtggc ctaactacgg ctacactaga aggacagtat
3601 ttggtatctg cgctctgctg aagccagtta ccttcggaaa aagagttggt agctcttgat
3661 ccggcaaaca aaccaccgct ggtagcggtg gttttttttgt ttgcaagcag cagattacgc
3721 gcagaaaaaa aggatctcaa gaagatcctt tgatcttttc tacggggtct gacgctcagt
3781 ggaacgaaaa ctcacgttaa gggattttgg tcatgaacaa taaaactgtc tgcttacata
3841 aacagtaata caaggggtgt tatgagccat attcaacggg aaacgtcttg ctctaggccg
3901 cgattaaatt ccaacatgga tgctgattta tatgggtata aatgggctcg cgataatgtc
3961 gggcaatcag gtgcgacaat ctatcgattg tatgggaagc ccgatgcgcc agagttgttt
4021 ctgaaacatg gcaaaggtag cgttgccaat gatgttacag atgagatggt cagactaaac
4081 tggctgacgg aatttatgcc tcttccgacc atcaagcatt ttatccgtac tcctgatgat
4141 gcatggttac tcaccactgc gatccccggg aaaacagcat tccaggtatt agaagaatat
4201 cctgattcag gtgaaaatat tgttgatgcg ctggcagtgt tcctgcgccg gttgcattcg
4261 attcctgttt gtaattgtcc ttttaacagc gatcgcgtat tcgtctcgc tcaggcgcaa
4321 tcacgaatga ataacggttt ggttgatgcg agtgattttg atgacgagcg taatggctgg
4381 cctgttgaac aagtctggaa agaaatgcat aaacttttgc cattctcacc ggattcagtc
4441 gtcactcatg gtgatttctc acttgataac cttatttttg acgaggggaa attaataggt
4501 tgtattgatg ttggacgagt cggaatcgca gaccgatacc aggatcttgc catcctatgg
4561 aactgcctcg gtgagttttc tccttcatta cagaaacggc ttttttcaaaa atatggtatt
4621 gataatcctg atatgaataa attgcagttt catttgatgc tcgatgagtt tttctaagaa
4681 ttaattcatg agcggataca tatttgaatg tatttagaaa aataaacaaa taggggttcc
4741 gcgcacattt ccccgaaaag tgccacctga aattgtaaac gttaatattt tgttaaaatt
4801 cgcgttaaat ttttgttaaa tcagctcatt ttttaaccaa taggccgaaa tcggcaaaat
4861 cccttataaa tcaaaagaat agaccgagat agggttgagt gttgttccag tttggaacaa
4921 gagtccacta ttaaagaacg tggactccaa cgtcaaaggg cgaaaaaccg tctatcaggg
4981 cgatggccca ctacgtgaac catcacccta atcaagtttt tggggtcga ggtgccgtaa
5041 agcactaaat cggaacccta aagggagccc ccgatttaga gcttgacggg gaaagccggc
5101 gaacgtggcg agaaaggaag ggaagaaagc gaaaggagcg ggcgctaggg cgctggcaag
5161 tgtagcggtc acgctgcgcg taaccaccac acccgccgcg cttaatgcgc cgctacaggg
5221 cgcgtcccat tcgcca
``` pET28a Vector Sequence (SEQ ID NO: 6)

```
   1 atccggatat agttcctcct ttcagcaaaa aaccccctcaa gacccgttta gaggccccaa
  61 ggggttatgc tagttattgc tcagcggtgg cagcagccaa ctcagcttcc tttcgggctt
 121 tgttagcagc cggatctcag tggtggtggt ggtggtgctc gagtgcggcc gcaagcttgt
```

-continued

```
 181 cgacggagct cgaattcgga tccgcgaccc atttgctgtc caccagtcat gctagccata
 241 tggctgccgc gcggcaccag gccgctgctg tgatgatgat gatgatggct gctgcccatg
 301 gtatatctcc ttcttaaagt taaacaaaat tatttctaga ggggaattgt tatccgctca
 361 caattcccct atagtgagtc gtattaattt cgcgggatcg agatctcgat cctctacgcc
 421 ggacgcatcg tggccggcat caccggcgcc acaggtgcgg ttgctggcgc ctatatcgcc
 481 gacatcaccg atggggaaga tcgggctcgc cacttcgggc tcatgagcgc ttgtttcggc
 541 gtgggtatgg tggcaggccc cgtggccggg ggactgttgg gcgccatctc cttgcatgca
 601 ccattccttg cggcggcgt gctcaacggc ctcaacctac tactgggctg cttcctaatg
 661 caggagtcgc ataagggaga gcgtcgagat cccggacacc atcgaatggc gcaaaacctt
 721 tcgcggtatg gcatgatagc gcccggaaga gagtcaattc agggtggtga atgtgaaacc
 781 agtaacgtta tacgatgtcg cagagtatgc cggtgtctct tatcagaccg tttcccgcgt
 841 ggtgaaccag gccagccacg tttctgcgaa aacgcgggaa aaagtggaag cggcgatggc
 901 ggagctgaat tacattccca accgcgtggc acaacaactg gcgggcaaac agtcgttgct
 961 gattggcgtt gccacctcca gtctggccct gcacgcgccg tcgcaaattg tcgcggcgat
1021 taaatctcgc gccgatcaac tgggtgccag cgtggtggtg tcgatggtag aacgaagcgg
1081 cgtcgaagcc tgtaaagcgg cggtgcacaa tcttctcgcg caacgcgtca gtgggctgat
1141 cattaactat ccgctggatg accaggatgc cattgctgtg aagctgcct gcactaatgt
1201 tccggcgtta tttcttgatg tctctgacca gacacccatc aacagtatta ttttctccca
1261 tgaagacggt acgcgactgg gcgtggagca tctggtcgca ttgggtcacc agcaaatcgc
1321 gctgttagcg ggcccattaa gttctgtctc ggcgcgtctg cgtctggctg gctggcataa
1381 atatctcact cgcaatcaaa ttcagccgat agcggaacgg gaaggcgact ggagtgccat
1441 gtccggtttt caacaaacca tgcaaatgct gaatgagggc atcgttccca ctgcgatgct
1501 ggttgccaac gatcagatgg cgctgggcgc aatgcgcgcc attaccgagt ccgggctgcg
1561 cgttggtgcg gatatctcgg tagtgggata cgacgatacc gaagacagct catgttatat
1621 cccgccgtta accaccatca acaggatttt cgcctgctg gggcaaacca gcgtggaccg
1681 cttgctgcaa ctctctcagg ccaggcggt gaagggcaat cagctgttgc ccgtctcact
1741 ggtgaaaaga aaaaccaccc tggcgcccaa tacgcaaacc gcctctcccc gcgcgttggc
1801 cgattcatta atgcagctgg cacgacaggt ttcccgactg gaaagcgggc agtgagcgca
1861 acgcaattaa tgtaagttag ctcactcatt aggcaccggg atctcgaccg atgcccttga
1921 gagccttcaa cccagtcagc tccttccggt gggcgcgggg catgactatc gtcgccgcac
1981 ttatgactgt cttctttatc atgcaactcg taggacaggt gccggcagcg ctctgggtca
2041 ttttcggcga ggaccgcttt cgctggagcg cgacgatgat cggcctgtcg cttgcggtat
2101 tcggaatctt gcacgccctc gctcaagcct tcgtcactgg tcccgccacc aaacgtttcg
2161 gcgagaagca ggccattatc gccggcatgg cggccccacg ggtgcgcatg atcgtgctcc
2221 tgtcgttgag gacccggcta ggctgcggg gttgccttac tggttagcag aatgaatcac
2281 cgatacgcga gcgaacgtga agcgactgct gctgcaaaac gtctgcgacc tgagcaacaa
2341 catgaatggt cttcggtttc cgtgtttcgt aaagtctgga acgcggaag tcagcgccct
2401 gcaccattat gttccggatc tgcatcgcag gatgctgctg gctaccctgt ggaacaccta
2461 catctgtatt aacgaagcgc tggcattgac cctgagtgat ttttctctgg tcccgccgca
2521 tccataccgc cagttgttta ccctcacaac gttccagtaa ccgggcatgt tcatcatcag
2581 taacccgtat cgtgagcatc ctctctcgtt tcatcggtat cattacccccc atgaacagaa
```

-continued

```
2641 atcccccttacacggaggcatcagtgaccaaacaggaaaaaaccgcccttaacatggccc 2701 gctttatcagaagccagacattaacgcttctggagaaaactcaacgagctgdacgcggatg 2761 aacaggcagacatctgtgaatcgcttcacgaccacgctgatgagctttaccgcagctgcc 2821 tcgcgcgtttcggtgatgacggtgaaaacctctgacacatgcagctcccggagacggtca 2881 cagcttgtctgtaagcggatgccgggagcagacaagcccgtcagggcgcgtcagcgggtg 2941 ttggcgggtgtcggggcgcagccatgacccagtcacgtagcgatagcggagtgtatactg 3001 gcttaactatgcggcatcagagcagattgtactgagagtgcaccatatatgcggtgtgaa 3061 ataccgcacagatgcgtaaggagaaaatacgcatcaggcgctcttccgcttcctcgctc 3121 actgactcgctgcgctcggtcgttcggctgcggcgagcggtatcagctcactcaaaggcg 3181 gtaatacggttatccacagaatcaggggataacgcaggaaagaacatgtgagcaaaaggc 3241 cagcaaaaggccaggaaccgtaaaaaggccgcgttgctggcgttttttccataggctccgc 3301 ccccctgacgagcatcacaaaaatcgacgctcaagtcagaggtggcgaaacccgacagga 3361 ctataaagataccaggcgtttccccctggaagctccctcgtgcgctctcctgttccgacc 3421 ctgccgcttaccggatacctgtccgcctttctcccttcggaagcgtggcgctttctcat 3481 agctcacgctgtaggtatctcagttcggtgtaggtcgttcgctccaagctgggctgtgtg 3541 cacgaaccccccgttcagcccgaccgctgcgccttatccggtaactatcgtcttgagtcc 3601 aacccggtaagacacgacttatcgccactggcagcagccactggtaacaggattagcaga 3661 gcgaggtatgtaggcggtgctacagagttcttgaagtggtggcctaactacggctacact 3721 agaaggacagtatttggtatctgcgctctgctgaagccagttaccttcggaaaaagagtt 3781 ggtagctcttgatccggcaaacaaaccaccgctggtagcggtggtttttttgtttgcaag 3841 cagcagattacgcgcagaaaaaaaggatctcaagaagatcctttgatcttttctacgggg 3901 tctgacgctcagtggaacgaaaactcacgttaagggattttggtcatgaacaataaaact 3961 gtctgcttacataaacagtaatacaaggggtgttatgagcatattcaacgggaaacgtc 4021 ttgctctaggccgcgattaaattccaacatggatgctgatttatatgggtataaatgggc 4081 tcgcgataatgtcgggcaatcaggtgcgacaatctatcgattgtatgggaagcccgatgc 4141 gccagagttgtttctgaaacatggcaaaggtagcgttgccaatgatgttacagatgagat 4201 ggtcagactaaactggctgacggaatttatgcctcttccgaccatcaagcattttatccg 4261 tactcctgatgatgcatggttactcaccactgcgatccccgggaaaacagcattccaggt 4321 attagaagaatatcctgattcaggtgaaaatattgttgatgcgctggcagtgttcctgcg 4381 ccggttgcattcgattcctgtttgtaattgtccttttaacagcgatcgcgtatttcgtct 4441 cgctcaggcgcaatcacgaatgaataacggtttggttgatgcgagtgattttgatgacga 4501 gcgtaatggctggcctgttgaacaagtctggaaagaaatgcataaacttttgccattctc 4561 accggattcagtcgtcactcatggtgatttctcacttgataaccttatttttgacgaggg 4621 gaaattaataggttgtattgatgttggacgagtcggaatcgcagaccgataccaggatct 4681 tgccatcctatggaactgcctcggtgagttttctccttcattacagaaacggctttttca 4741 aaaatatggtattgataatcctgatatgaataaattgcagtttcatttgatgctcgatga 4801 gttttttctaagaattaattcatgagcggatacatatttgaatgtatttagaaaaataaac 4861 aaataggggttccgcgcacatttccccgaaaagtgccacctaaattgtaaagcgttaatat 4921 tttgttaaaattcgcgttaaattttgttaaatcagctcatttttaaccaataggccga 4981 aatcggcaaaatcccttataaatcaaaagaatagaccgagatagggttgagtgttgttcc 5041 agtttggaacaagagtccactattaaagaacgtggactccaacgtcaaagggcgaaaaac
```

```
-continued
5101  cgtctatcag ggcgatggcc cactacgtga accatcaccc taatcaagtt ttttggggtc 5161  gaggtgccgt aaagcactaa atcggaaccc taaagggagc ccccgattta gagcttgacg 5221  gggaaagccg gcgaacgtgg cgagaaagga agggaagaaa gcgaaaggag cgggcgctag 5281  ggcgctggca agtgtagcgg tcacgctgcg cgtaaccacc acacccgccg cgcttaatgc 5341  gccgctacag ggcgcgtccc attcgcca
```

Cloning Validation (Prophetic)

Cloned genes will be sequenced for confirmation prior to subcloning onto expression vectors. Proteins will be purified using nickel-affinity chromatography (His-tagged versions) or by precipitation of undesired proteins by heat (No-tagged versions). Enzyme activity will be improved, if necessary, by site directed mutagenesis to increase the affinity for the substrates or the stability. Such modifications will be made based on crystallographic and biochemical studies performed in other members of the dehydrogenases family of enzymes. We will isolate and purify two versions of each of phenylalanine dehydrogenase and glutamate dehydrogenase from G. thermoglucosidiasius and Thermus thermophilus organisms, respectively. Purification can be completed for example after harvesting cell culture, lysing the cells and running the cellular lysate over a Nickel-tagged column that has affinity for His-tagged protein sequences followed by standard elution.

Example 5

Phenylalaine Sensor Fabrication (Prophetic)

Dehydrogenases generally affect amino acids by cleaving off the primary amine thereby generating ammonia. A cofactor to these enzymes is nicotinamide adenine dinucleotide (NAD+). During the catalytic event NAD+ is reduced to NADH. This is advantageous as NADH is a reducing agent that can be detected using electrochemistry. If this reaction is performed on an exposed electrode under a certain voltage, NADH will liberate electrons to the electrode producing a current. The magnitude of this current can then be correlated to the concentration of phenylalanine To fabricate a hydrogel matrix (the schematic for which appears in FIG. 5) a 1 mL stock solution in 1× phosphate buffered saline containing the following will be prepared as follows:
  a. 40 units of phenylalanine dehydrogenase
  b. 20 mL of 0.05M Toluidine Blue (the mediator)
  c. 5 mM β-Nicotinamide adenine dinucleotide, reduced dipotassium salt
  d. 1% weight/volume sodium alginate from brown algae 10 mL of the pre-gel solution will be spread onto a three electrode screen printed carbon electrode. The electrode contains both a counter and working electrode as well as a silver/silver chloride reference electrode. The working electrode acts as the sensing electrode. The pre-gel solution on the electrode will then be sprayed with a 0.1M CaCl2 solution using a Badger 200N airbrush at 7.5 psi for 1 second, depositing ~5 mL of the CaCl2 solution. The gel will be allowed to cure for 30 minutes in a humid environment.

Additional components such as varying concentration of trehalose will be added to the hydrogel matrix mixture above. Additional component of the hydrogel may also include: one or more anionic monomers and crosslinkers.

Anionic Monomers (Prophetic)

Several candidates for enhancement of an anion filter have been identified, each of which contain a negative charge in order to repel any anions that may interfere with the electrode. 2-acrylamido-2- methylpropane sulfonic acid (AMPS) is a sulfonic acid containing monomer with a permanent negative charge that can be polymerized via radical polymerization in solution with the enzyme, cofactors and crosslinker. Other suitable anionic monomer candidates include methacrylic acid, 2-sulfoethyl me1thacrylate, and 2-propene-1-sulfonic acid. Enzyme activity will be verified in conjunction with the other hydrogel components through amperometric detection with a potentiostat for each composition.

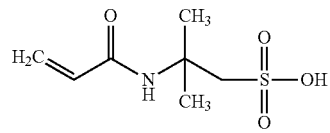

2-Acrylamido-2-methylpropane sulfonic acid

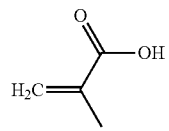

Methacrylic acid

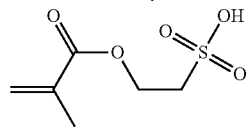

2-Sulfoethyl methacrylate

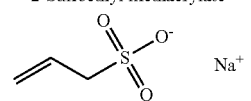

2-Propene-1-sulfonic acid

Easily reduced molecules termed mediators can facilitate propagation of the electrochemical event. Mediators effectively shuttle electrons from the NADH to the electrode allowing for higher sensitivity and protection of the integrity of the electrode surface. Ideally mediator molecules are immobilized close to the electrode surface to eliminate diffusion as a rate-limiting step in the propagation of electrons. Common mediators for shuttling electrons from NADH include thionine, o-phenylenediamine, methylene blue and toluidine blue.

Toluidine blue will be immobilized onto the surface of the electrode by electropolymerization. Additionally if the enzyme is present during this electropolymerization event, the enzyme can be entrapped in the polymerized layer of the mediator and optional alginate solution. The advantage of such an immobilization lies in that the enzyme will produce NADH directly in the vicinity of the polymerized mediator layer, completely eliminating diffusion as a rate limiting step of propagation of the current response.

Crosslinkers (Prophetic)

Polyethylene glycol dimethacrylate (PEGDA) or tetraethylene glycol diacrylate (TEGDA) will be used as optional crosslinkers in the anionic and mediator polymers, creating a hydrogel that serves as a molecular weight cut off filter and an immobilizing mechanism for the enzyme and its cofactors.

Varying the amount and molecular weight of these polyethylene glycol derivatives will yield different enzyme stabilities and kinetics due to diffusion and steric hindrance as well as alter the molecular weight cut off filter mesh size. Polyethylene glycol derivatives are the choice for the crosslinker because they will minimize interactions and modifications with the enzyme preventing adsorption. Both PEGDA and TEGDA will be polymerized in the monomer solution that contains the enzyme and cofactors via free radical polymerization. Enzyme activity will be verified in conjunction with the other hydrogel components.

Upon successful production of phenylalanine dehydrogenase, electrochemical detection of phenylalanine will be performed under ideal conditions in buffered solution. Phenylalanine dehydrogenase concentrations, NAD+, and toluidine blue will be dissolved in phosphate buffered saline (PBS) and placed on screen printed carbon electrodes containing a silver/silver chloride reference electrode, working (or measuring) electrode, and counter electrode. After the electrode equilibrates, stock solutions of phenylalanine in PBS will be: directly added to the enzyme solution on the electrode and current will be measured by amperometric detection using a potentiostat. Detection will be carried out at an operating voltage determined by cyclic voltammetry. Concentrations of phenylalanine ranging in concentrations between 60 and 1200 mM will be used to generate a standard curve within the physiological range of healthy individuals and individuals with PKU. A variety of techniques for data analysis will be utilized to identify the most accurate and reproducible method of correlating current generation to phenylalanine concentration. This task will demonstrate the ability to detect physiological phenylalanine concentrations as well as determine the enzyme and cofactor concentrations necessary for accurate detection in this range.

After the best candidates for immobilization of phenylalanine dehydrogenase and its cofactors are identified, current generation will be quantified via amperometric detection of phenylalanine concentrations in the range of 60 and 1200 mM. This will be used to generate a standard curve within the physiological range of healthy individuals and individuals with PKU. A variety of techniques for data analysis will be utilized to identify the most accurate and reproducible method of corresponding current generation to phenylalanine concentration. Sensor stability will be assessed through long-term storage at room temperature, about 4 degrees Celsius, and about −20 degrees Celsius. Detection sustainability will then be determined at 1, 3, 5, and 10 weeks for each storage condition using stock solutions of phenylalanine in PBS.

Example 6

Alternative Phenylalanine Sensor (Prophetic)

Figure 14:
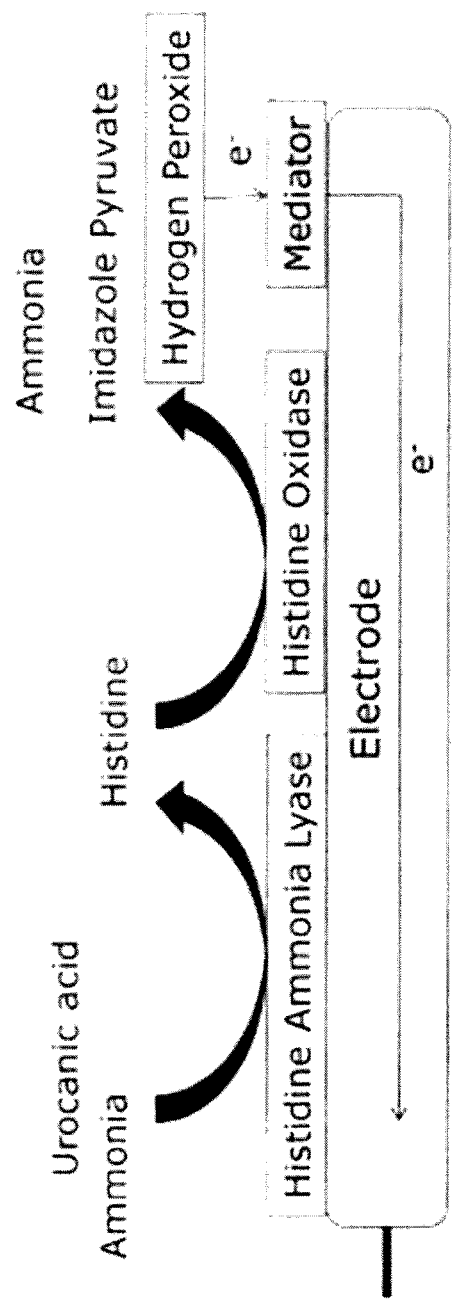
FIG. 14 depicts a general schematic of another embodiment in which histidine levels can be determined by immobilization of two metabolic enzymes and use of hydrogen peroxide as a reduction agent.
Figure 15:
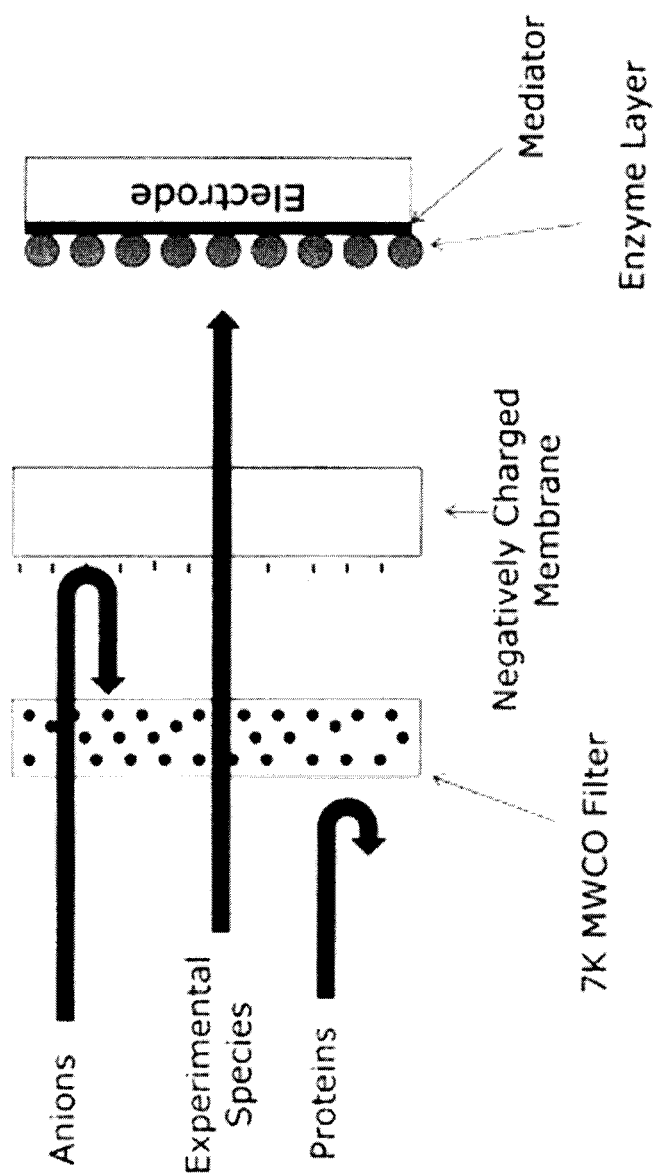
FIG. 15 depicts an embodiment utilizing a negatively charged barrier such as a membrane that physically filters molecules from the electrode system thereby reducing interference of signals.
Figure 16:
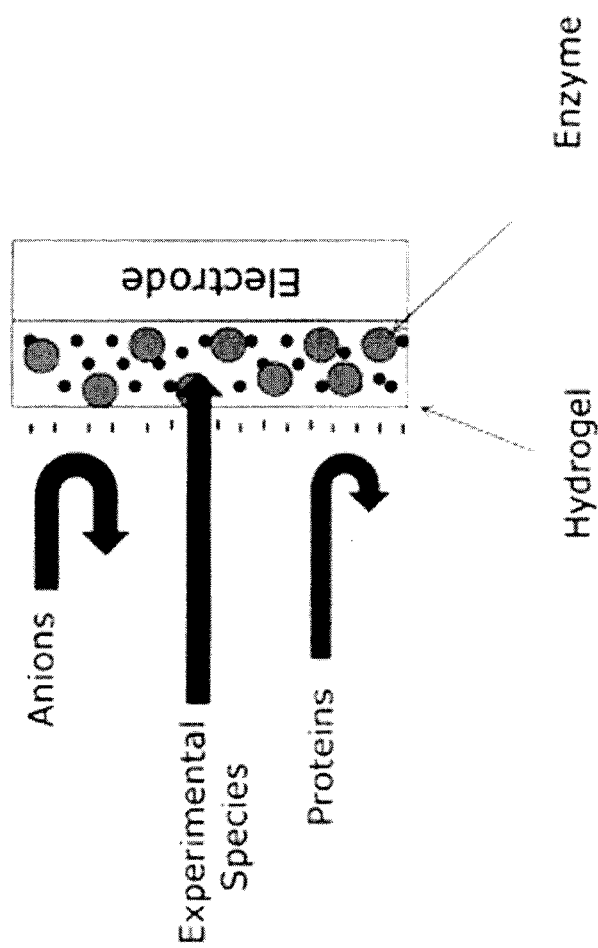
FIG. 16 depicts an embodiment of the invention that does not use a physical membrane filter or molecular weight filter but uses the chemical properties of the hydrogel by itself as a way to reduce interference in signal. Unlike the embodiment depicted in FIG. 3, this embodiment utilizes a hydrogel that does not contain alginate.
Figure 17:
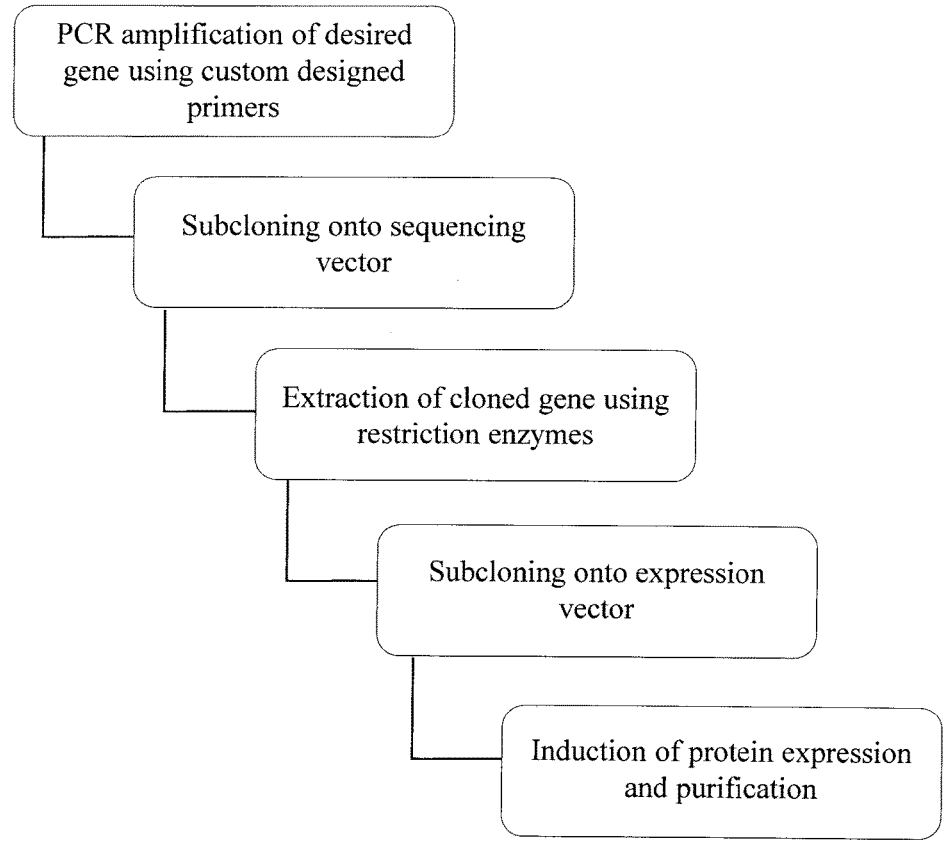
FIG. 17 depicts the cloning strategy and steps taken to isolate the metabolic enzyme of choice.

Rather than rely on only one method to measure the quantity of phenylalanine in a bodily fluid such as a blood sample or plasma, other embodiments of the device will be made utilizing the same deposition chemistry for electrode surface modification with various hydrogels and components described above. Phenylalanine dehydrogenase will be replaced in an embodiment with immobilization of phenylalanine ammonia-lyase (PAL), (SEQ ID NO:7 or functional fragments thereof that are at least 70% homolgous to SEQ ID NO:7). This enzyme will catalyze a reaction of phenylalanine and produce cinnamic acid and ammonia. Cinnamic acid can be measured spectrophotometrically since it produces a blue color in the presence of Fe and KOH. Ammonia release in the presence of hydrogen peroxide will produce an electron transfer to an electrode coated with hydrogel. Current from electron transfers similar to the above-described methods can be detected by the working electrode. (Similar to the electrode depicted in FIG. 14).

Example 7

Phenylalanine Sensor Methods

The hydrogel's ability to act as an anion and molecular weight cut off filter will be verified by measuring phenylalanine levels from platelet poor plasma and whole blood. Phenylalanine will be added to the serum being tested to achieve a range of concentrations and then directly added to the hydrogel-coated electrode. As previously performed, phenylalanine concentrations will be measured by amperometric detection using a potentiostat. All amperometric concentration measurements will be compared to analysis by tandem mass spectrometry to verify accuracy.

Validation of the functionality of the biosensor will also be performed using the following experimental design. The evaluation of the efficacy of the phenylalanine sensor requires the construction of a three carbon electrode modified with an alginate hydrogel consisting of alginate, CaCl2, Toluidine Blue, Phenylalanine Dehydrogenase, and NAD (P)+. The hydrogel will act as a filter to prevent interference from small molecules and proteins in whole blood. Initially 32 whole blood samples will be tested with phenylalanine concentrations ranging from about 35 µM to about 2000 µM. Specifically the following Phe concentrations will be tested on the enzyme electrode: 35, 100, 250, 500, 1000, 1250, 1500, 2000 µM. In this experiment 35 µM will represent a physiologically normal concentration and each other concentration above 100 µM will represent a variety of different diseased concentrations. These concentrations will be generated by doping whole blood of a concentration lower than 35 µM. Additionally, subject samples will be tested to ensure the sensor operates without issues form unforeseen abnormalities with patient whole blood. All phenylalanine concentration will be verified by the use of high performance liquid chromatography (HPLC), which is the gold standard for determining phenylalanine levels in blood. The samples will not require preprocessing. The blood will be taken using sodium heparin vacuum tubes and then used unmodified outside of doping the blood with higher phenylalanine concentrations. The expected detection limit is 35 µM with a range of 35-2000 µM and a resolution of 20 µM. Statistical Evaluations will be performed to assess the reliability of the concentration measurements. The concentration measurements will be analyzed using ANOVA single factor analysis to demonstrate differences between groups assuming a normal data distribution. Confidence intervals will be assessed and the sensitivity and the reproducibility of the method demonstrated. Concentration measurements ranging from normal physiological conditions to diseased conditions with a confidence 95% ($p<0.05$) or higher will be deemed statistically significant. Statistical differences between diseased concentration levels and healthy, physiological concentration levels will first be demonstrated. Subsequent experimentation will be used to validate quantification of over the full range of discrete concentration values.

EQUIVALENTS

Those skilled in the art will recognize, or be able to ascertain using no more than routine experimentation, many

The invention claimed is:

1. A biosensor comprising:
at least one electrically conductive support, the at least one electrically conductive support attached to a hydrogel, the hydrogel comprising at least one electron mediator, at least one reduction agent, and at least one metabolic enzyme from a thermophilic bacterial cell or functional fragment thereof, wherein the hydrogel comprises alginate; and
an amperometer and/or voltmeter operably connected to the at least one electrically conductive support;
wherein the at least one electrically conductive support comprises a phenylalanine dehydrogenase or functional fragments thereof; and
wherein the phenylalanine dehydrogenase or functional fragment thereof comprises at least about 70% sequence identity to SEQ ID NO:1 or SEQ ID NO:2.

2. The biosensor of claim 1, wherein the biosensor comprises at least three electrically conductive supports, wherein at least one electrically conductive support is a silver and silver chloride wire.

3. The biosensor of claim 1, wherein the biosensor comprises at least a first and a second electrically conductive support, wherein the first electrically conductive support is attached to the hydrogel, and wherein said first and second electrically conductive supports are operably connected to said voltmeter and/or amperometer to apply a voltage therebetween.

4. The biosensor of claim 1, wherein the at least one electrically conductive support comprises an electronegative or anionic chemical component.

5. The biosensor of claim 1, wherein the at least one hydrogel comprises trehalose.

6. The biosensor of claim 1, wherein the biosensor does not comprise one or more of the following: (i) uricase or a functional fragment thereof; (ii) a hydrogel comprising dextran or a derivative thereof; (iii) a bacterial cell; (iv) an electronic dipole configured for electrophoresis; and (v)3,4-dihydroxybenzoic acid (3,4-DHB).

7. The biosensor of claim 1, wherein the biosensor is at least 70% biologically active after about thirty days in storage at 4 degrees Celsius.

8. The biosensor of claim 1, wherein the biosensor is not functionally dependent upon exposure to UV light.

9. The biosensor of claim 1, wherein the at least one enzyme or functional fragment thereof comprises at least about 80% sequence identity to SEQ ID NO:1 or SEQ ID NO:2.

10. The biosensor of claim 1, wherein the at least one metabolic enzyme or functional fragment thereof comprises at least about 90% sequence identity to SEQ ID NO: 1.

11. The biosensor of claim 1, wherein the hydrogel comprises trehalose, wherein the hydrogel comprises an alginate concentration from about 1% to about 3% weight to volume of the total volume attached to the at least one electrically conductive support; and wherein the electrically conductive support comprises a wire comprising silver and silver chloride in operable connection to the voltmeter and/or amperometer.

12. The biosensor of claim 1, wherein the hydrogel comprises an alginate comprising a block polymer with a formula:

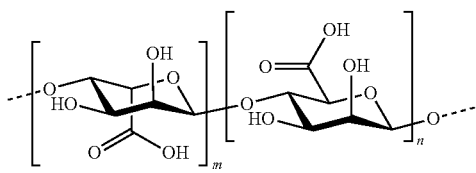

wherein m and n are any positive integer.

13. The biosensor of claim 1, wherein the at least one reduction agent is chosen from: NAD+ or FAD+.

14. A system comprising the biosensor of claim 1 in operable connection to at least one computer storage memory, and a computer processor in operable connection with the at least one computer storage memory.

15. The system of claim 14, further comprising a digital display in operable connection to the at least one electrically conductive support by an electrical circuit capable of carrying an a electrical signal corresponding to a measurement of current and/or voltage differential from the voltmeter and/or amperometer to the digital display, wherein the digital display is configured to display concentration value of an amino acid in a sample when the at least one electrically conductive support is in contact with the sample for a time period sufficient for the at least one metabolic enzyme to catalyze the oxidation of its amino acid substrate.

16. The system of claim 15, wherein the metabolic enzyme is a phenylalanine dehydrogenase immobilized within the hydrogel and wherein the hydrogel comprises an alginate concentration from about 1% to about 3% weight to volume of the total volume attached to the at least one electrically conductive support.

17. A biosensor comprising:
at least one electrically conductive support, the at least one electrically conductive support attached to at least one hydrogel, the hydrogel comprising at least one electron mediator, at least one reduction agent, and at least one metabolic enzyme or functional fragment thereof;

wherein the at least one enzyme or functional fragment thereof has an amino acid sequence at least 70% homologous to SEQ ID NO:1 or at least 70% homologous to a functional fragment of SEQ ID NO:1; and an amperometer and/or voltmeter operably connected to the at least one electrically conductive support.

18. The biosensor of claim 17, wherein the enzyme or functional fragment thereof has an amino acid sequence at least 80% homologous to SEQ ID NO:1 or at least 80% homologous to a functional fragment of SEQ ID NO:1.

19. The biosensor of claim 17, wherein the enzyme or functional fragment thereof has an amino acid sequence at least 90% homologous to SEQ ID NO:1 or at least 90% homologous to a functional fragment of SEQ ID NO:1.

* * * * *

SEQUENCE LISTING

<160> NUMBER OF SEQ ID NOS: 10

<210> SEQ ID NO 1
<211> LENGTH: 378
<212> TYPE: PRT
<213> ORGANISM: Geobacillus thermoglucosidiasius

<400> SEQUENCE: 1

```
Met Asn Thr Val Thr Asn Gln Trp Lys Ala Val Asp Ile Phe Thr Gln
1               5                  10                  15

Ile Arg Asp His Glu Gln Val Val Phe Cys Asn Asp Lys Asn Thr Gly
            20                  25                  30

Leu Lys Ala Ile Ile Ala Ile His Asp Thr Thr Leu Gly Pro Ala Leu
        35                  40                  45

Gly Gly Cys Arg Met Tyr Pro Tyr Ala Thr Val Glu Asp Ala Leu Phe
50                  55                  60

Asp Val Leu Arg Leu Ser Lys Gly Met Thr Tyr Lys Cys Leu Ala Ala
65                  70                  75                  80

Asp Val Asp Phe Gly Gly Gly Lys Ala Val Ile Ile Gly Asp Pro His
                85                  90                  95

Lys Asp Lys Thr Pro Glu Leu Phe Arg Ala Phe Gly Gln Phe Val Glu
            100                 105                 110

Ser Leu Asn Gly Arg Phe Tyr Thr Gly Thr Asp Met Gly Thr Thr Pro
        115                 120                 125

Asp Asp Phe Val His Ala Met Lys Glu Thr Asn Cys Ile Val Gly Val
130                 135                 140

Pro Glu Glu Tyr Gly Gly Ser Gly Asp Ser Ser Val Pro Thr Ala Leu
145                 150                 155                 160

Gly Val Ile Tyr Gly Ile Gln Ala Thr Asn Lys Val Ile Trp Gly Ser
                165                 170                 175

Asp Glu Leu His Gly Lys Thr Tyr Ala Ile Gln Gly Leu Gly Lys Val
            180                 185                 190

Gly Arg Lys Val Ala Glu Arg Leu Leu Lys Glu Gly Ala Asp Leu Tyr
        195                 200                 205

Val Cys Asp Ile His Pro Thr Ala Ile Glu Ala Ile Val Ser Tyr Ala
210                 215                 220

Lys Lys Leu Gly Ala Asn Val Lys Val Val Gln Gly Thr Glu Ile Tyr
225                 230                 235                 240

Arg Thr Asp Ala Asp Ile Phe Val Pro Cys Ala Phe Gly Asn Val Val
                245                 250                 255

Asn Asp Asn Thr Ile His Val Leu Lys Val Lys Ala Ile Val Gly Ser
            260                 265                 270

Ala Asn Asn Gln Leu Leu Asp Val Arg His Gly Gln Leu Leu Lys Glu
        275                 280                 285

Lys Gly Ile Leu Tyr Ala Pro Asp Tyr Ile Val Asn Ala Gly Gly Leu
290                 295                 300

Ile Gln Val Ala Asp Glu Leu Tyr Gly Leu Asn Lys Glu Arg Val Leu
305                 310                 315                 320

Gln Lys Thr Lys Ala Ile Tyr Ser Thr Leu Leu His Ile Tyr Ser Arg
                325                 330                 335

Ala Glu Ala Asp His Ile Thr Thr Ile Glu Ala Ala Asn Arg Phe Cys
            340                 345                 350
```

Glu Glu Arg Leu Gln Gln Arg Ser Arg Arg Asn Asp Phe Thr His
                355                 360                 365

Arg Lys Gln Pro Lys Trp Asp Ile Arg Arg
    370                 375

<210> SEQ ID NO 2
<211> LENGTH: 366
<212> TYPE: PRT
<213> ORGANISM: Thermoactinomyces intermedius

<400> SEQUENCE: 2

Met Arg Asp Val Phe Glu Met Met Asp Arg Tyr Gly His Glu Gln Val
1               5                   10                  15

Ile Phe Cys Arg His Pro Gln Thr Gly Leu Lys Ala Ile Ile Ala Leu
            20                  25                  30

His Asn Thr Thr Ala Gly Pro Ala Leu Gly Gly Cys Arg Met Ile Pro
        35                  40                  45

Tyr Ala Ser Thr Asp Glu Ala Leu Glu Asp Val Leu Arg Leu Ser Lys
    50                  55                  60

Gly Met Thr Tyr Lys Cys Ser Leu Ala Asp Val Asp Phe Gly Gly Gly
65                  70                  75                  80

Lys Met Val Ile Ile Gly Asp Pro Lys Lys Asp Lys Ser Pro Glu Leu
                85                  90                  95

Phe Arg Val Ile Gly Arg Phe Val Gly Gly Leu Asn Gly Arg Phe Tyr
            100                 105                 110

Thr Gly Thr Asp Met Gly Thr Asn Pro Glu Asp Phe Val His Ala Ala
        115                 120                 125

Arg Glu Ser Lys Ser Phe Ala Gly Leu Pro Lys Ser Tyr Gly Gly Lys
    130                 135                 140

Gly Asp Thr Ser Ile Pro Thr Ala Leu Gly Val Phe His Gly Met Arg
145                 150                 155                 160

Ala Thr Ala Arg Phe Leu Trp Gly Thr Asp Gln Leu Lys Gly Arg Val
                165                 170                 175

Val Ala Ile Gln Gly Val Gly Lys Val Gly Glu Arg Leu Leu Gln Leu
            180                 185                 190

Leu Val Glu Val Gly Ala Tyr Cys Lys Ile Ala Asp Ile Asp Ser Val
        195                 200                 205

Arg Cys Glu Gln Leu Lys Glu Tyr Gly Asp Lys Val Gln Leu Val
    210                 215                 220

Asp Val Asn Arg Ile His Lys Glu Ser Cys Asp Ile Phe Ser Pro Cys
225                 230                 235                 240

Ala Lys Gly Gly Val Val Asn Asp Asp Thr Ile Asp Glu Phe Arg Cys
                245                 250                 255

Leu Ala Ile Val Gly Ser Ala Asn Asn Gln Leu Val Glu Asp Arg His
            260                 265                 270

Gly Ala Leu Leu Gln Lys Arg Ser Ile Cys Tyr Ala Pro Asp Tyr Leu
        275                 280                 285

Val Asn Ala Gly Gly Leu Ile Gln Val Ala Asp Glu Leu Glu Gly Phe
    290                 295                 300

His Glu Glu Arg Val Leu Ala Lys Thr Glu Ala Ile Tyr Asp Met Val
305                 310                 315                 320

Leu Asp Ile Phe His Arg Ala Lys Asn Glu Asn Ile Thr Thr Cys Glu
                325                 330                 335

```
Ala Ala Asp Arg Ile Val Met Glu Arg Leu Lys Lys Leu Thr Asp Ile
            340                 345                 350

Arg Arg Ile Leu Leu Glu Asp Pro Arg Asn Ser Ala Arg Arg
        355                 360                 365

<210> SEQ ID NO 3
<211> LENGTH: 38
<212> TYPE: DNA
<213> ORGANISM: Artificial Sequence
<220> FEATURE:
<223> OTHER INFORMATION: 5' Primer for PheDH

<400> SEQUENCE: 3
tgtgctagca tgaataccgt taccaatcag tggaaagc                          38

<210> SEQ ID NO 4
<211> LENGTH: 32
<212> TYPE: DNA
<213> ORGANISM: Artificial Sequence
<220> FEATURE:
<223> OTHER INFORMATION: 3' primer for PheDH

<400> SEQUENCE: 4
ctcgagtcat taccggcgga tatcccactt cg                                32

<210> SEQ ID NO 5
<211> LENGTH: 5236
<212> TYPE: DNA
<213> ORGANISM: Artificial Sequence
<220> FEATURE:
<223> OTHER INFORMATION: pET24a Vector Sequence

<400> SEQUENCE: 5
atccggatat agttcctcct ttcagcaaaa aaccccctca agacccgttta gaggccccaa    60 ggggttatgc tagttattgc tcagcggtgg cagcagccaa ctcagcttcc tttcgggctt   120
tgttagcagc cggatctcag tggtggtggt ggtggtgctc gagtgcggcc gcaagcttgt   180
cgacggagct cgaattcgga tcctagaggg gaattgttat ccgctcacaa ttcccctata   240
gtgagtcgta ttaatttcgc gggatcgaga tctcgatcct ctacgccgga cgcatcgtgg   300
ccggcatcac cggcgccaca ggtgcggttg ctggcgccta tcgcgcgac atcaccgatg   360 gggaagatcg gctcgccac ttcgggctca tgagcgcttg tttcggcgtg ggtatggtgg   420
caggccccgt ggccggggga ctgttgggcg ccatctcctt gcatgcacca ttccttgcgg   480
cggcggtgct caacggcctc aacctactac tgggctgctt cctaatgcag gagtcgcata   540
agggagagcg tcgagatccc ggacaccatc gaatggcgca aaacctttcg cggtatggca   600
tgatagcgcc cggaagagag tcaattcagg gtggtgaatg tgaaaccagt aacgttatac   660
gatgtcgcag agtatgccgg tgtctcttat cagaccgttt cccgcgtggt gaaccaggcc   720
agccacgttt ctgcgaaaac gcgggaaaaa gtggaagcgg cgatggcgga gctgaattac   780
attcccaacc gcgtggcaca acaactggcg gcaaacagt cgttgctgat tggcgttgcc   840
acctccagtc tggccctgca cgcgccgtcg caaattgtcg cggcgattaa atctcgcgcc   900
gatcaactgg gtgccagcgt ggtggtgtcg atggtagaac gaagcggcgt cgaagcctgt   960
aaagcggcgg tgcacaatct tctcgcgcaa cgcgtcagtg ggctgatcat taactatccg  1020
ctggatgacc aggatgccat tgctgtggaa gctgcctgca ctaatgttcc ggcgttattt  1080
cttgatgtct ctgaccagac acccatcaac agtattattt tctcccatga agacggtacg  1140
cgactgggcg tggagcatct ggtcgcattg ggtcaccagc aaatcgcgct gttagcgggc  1200
```

```
ccattaagtt ctgtctcggc gcgtctgcgt ctggctggct ggcataaata tctcactcgc    1260
aatcaaattc agccgatagc ggaacgggaa ggcgactgga gtgccatgtc cggttttcaa    1320
caaaccatgc aaatgctgaa tgagggcatc gttcccactg cgatgctggt tgccaacgat    1380
cagatggcgc tgggcgcaat gcgcgccatt accgagtccg ggctgcgcgt tggtgcggat    1440
atctcggtag tgggatacga cgataccgaa gacagctcat gttatatccc gccgttaacc    1500
accatcaaac aggattttcg cctgctgggg caaaccagcg tggaccgctt gctgcaactc    1560
tctcagggcc aggcggtgaa gggcaatcag ctgttgcccg tctcactggt gaaaagaaaa    1620
accaccctgg cgcccaatac gcaaaccgcc tctccccgcg cgttggccga ttcattaatg    1680
cagctggcac gacaggtttc ccgactggaa agcgggcagt gagcgcaacg caattaatgt    1740
aagttagctc actcattagg caccgggatc tcgaccgatg cccttgagag ccttcaaccc    1800
agtcagctcc ttccggtggg cgcggggcat gactatcgtc gccgcactta tgactgtctt    1860
ctttatcatg caactcgtag gacaggtgcc ggcagcgctc tgggtcattt tcggcgagga    1920
ccgctttcgc tggagcgcga cgatgatcgg cctgtcgctt gcggtattcg gaatcttgca    1980
cgccctcgct caagccttcg tcactggtcc cgccaccaaa cgtttcggcg agaagcaggc    2040
cattatcgcc ggcatggcgg ccccacgggt gcgcatgatc gtgctcctgt cgttgaggac    2100
ccggctaggc tggcggggtt gccttactgg ttagcagaat gaatcaccga tacgcgagcg    2160
aacgtgaagc gactgctgct gcaaaacgtc tgcgacctga gcaacaacat gaatggtctt    2220
cggtttccgt gtttcgtaaa gtctggaaac gcggaagtca gcgccctgca ccattatgtt    2280
ccggatctgc atcgcaggat gctgctggct accctgtgga cacctacat ctgtattaac     2340 gaagcgctgg cattgaccct gagtgatttt tctctggtcc cgccgcatcc ataccgccag    2400
ttgtttaccc tcacaacgtt ccagtaaccg ggcatgttca tcatcagtaa cccgtatcgt    2460
gagcatcctc tctcgtttca tcggtatcat taccccccatg aacagaaatc ccccttacac   2520
ggaggcatca gtgaccaaac aggaaaaaac cgcccttaac atgcccgct ttatcagaag     2580 ccagacatta acgcttctgg agaaactcaa cgagctggac gcggatgaac aggcagacat    2640
ctgtgaatcg cttcacgacc acgctgatga gctttaccgc agctgcctcg cgcgtttcgg    2700
tgatgacggt gaaaacctct gacacatgca gctcccggag acggtcacag cttgtctgta    2760
agcggatgcc gggagcagac aagcccgtca gggcgcgtca gcgggtgttg gcgggtgtcg    2820
gggcgcagcc atgacccagt cacgtagcga tagcggagtg tatactggct taactatgcg    2880
gcatcagagc agattgtact gagagtgcac catatatgcg gtgtgaaata ccgcacagat    2940
gcgtaaggag aaaataccgc atcaggcgct cttccgcttc ctcgctcact gactcgctgc    3000
gctcggtcgt tcggctgcgg cgagcggtat cagctcactc aaaggcggta atacggttat    3060
ccacagaatc aggggataac gcaggaaaga acatgtgagc aaaaggccag caaaaggcca    3120
ggaaccgtaa aaaggccgcg ttgctggcgt ttttccatag gctccgcccc cctgacgagc    3180
atcacaaaaa tcgacgctca agtcagaggt ggcgaaaccc gacaggacta taaagatacc    3240
aggcgtttcc ccctggaagc tccctcgtgc gctctcctgt tccgaccctg ccgcttaccg    3300
gatacctgtc cgcctttctc ccttcgggaa gcgtggcgct ttctcatagc tcacgctgta    3360
ggtatctcag ttcggtgtag tcgttcgct ccaagctggg ctgtgtgcac gaacccccg      3420 ttcagcccga ccgctgcgcc ttatccggta actatcgtct tgagtccaac ccggtaagac    3480
acgacttatc gccactggca gcagccactg gtaacaggat tagcagagcg aggtatgtag    3540
gcggtgctac agagttcttg aagtggtggc ctaactacgg ctacactaga aggacagtat    3600
```

```
ttggtatctg cgctctgctg aagccagtta ccttcggaaa aagagttggt agctcttgat    3660
ccggcaaaca aaccaccgct ggtagcggtg gttttttttgt ttgcaagcag cagattacgc    3720
gcagaaaaaa aggatctcaa gaagatcctt tgatcttttc tacgggtct gacgctcagt     3780 ggaacgaaaa ctcacgttaa gggattttgg tcatgaacaa taaaactgtc tgcttacata    3840
aacagtaata caaggggtgt tatgagccat attcaacggg aaacgtcttg ctctaggccg    3900
cgattaaatt ccaacatgga tgctgattta tatgggtata atgggctcg cgataatgtc     3960 gggcaatcag gtgcgacaat ctatcgattg tatgggaagc ccgatgcgcc agagttgttt    4020
ctgaaacatg gcaaaggtag cgttgccaat gatgttacag atgagatggt cagactaaac    4080
tggctgacgg aatttatgcc tcttccgacc atcaagcatt ttatccgtac tcctgatgat    4140
gcatggttac tcaccactgc gatccccggg aaaacagcat tccaggtatt agaagaatat    4200
cctgattcag gtgaaaatat tgttgatgcg ctggcagtgt tcctgcgccg gttgcattcg    4260
attcctgttt gtaattgtcc ttttaacagc gatcgcgtat ttcgtctcgc tcaggcgcaa    4320
tcacgaatga ataacggttt ggttgatgcg agtgattttg atgacgagcg taatggctgg    4380
cctgttgaac aagtctggaa agaaatgcat aaacttttgc cattctcacc ggattcagtc    4440
gtcactcatg gtgatttctc acttgataac cttatttttg acgaggggaa attaataggt    4500
tgtattgatg ttggacgagt cggaatcgca gaccgatacc aggatcttgc catcctatgg    4560
aactgcctcg gtgagttttc tccttcatta cagaaacggc tttttcaaaa atatggtatt    4620
gataatcctg atatgaataa attgcagttt catttgatgc tcgatgagtt tttctaagaa    4680
ttaattcatg agcggataca tatttgaatg tatttagaaa aataaacaaa tagggggttcc    4740 gcgcacattt ccccgaaaag tgccacctga aattgtaaac gttaatattt tgttaaaatt    4800
cgcgttaaat ttttgttaaa tcagctcatt ttttaaccaa taggccgaaa tcggcaaaat    4860
cccttataaa tcaaaagaat agaccgagat agggttgagt gttgttccag tttggaacaa    4920
gagtccacta ttaaagaacg tggactccaa cgtcaaaggg cgaaaaaccg tctatcaggg    4980
cgatggccca ctacgtgaac catcacccta atcaagtttt ttggggtcga ggtgccgtaa    5040
agcactaaat cggaacccta aagggagccc ccgatttaga gcttgacggg gaaagccggc    5100
gaacgtggcg agaaaggaag ggaagaaagc gaaaggagcg gcgctaggg cgctggcaag     5160 tgtagcggtc acgctgcgcg taaccaccac acccgccgcg cttaatgcgc cgctacaggg    5220
cgcgtcccat tcgcca                                                    5236
```

<210> SEQ ID NO 6
<211> LENGTH: 5368
<212> TYPE: DNA
<213> ORGANISM: Artificial Sequence
<220> FEATURE:
<223> OTHER INFORMATION: pET28a vector sequence

<400> SEQUENCE: 6

```
atccggatat agttcctcct ttcagcaaaa aaccccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacggagct cgaattcgga tccgcgaccc atttgctgtc caccagtcat gctagccata    240
tggctgccgc gcggcaccag gccgctgctg tgatgatgat gatgatggct gctgcccatg    300
gtatatctcc ttcttaaagt taaacaaaat tatttctaga ggggaattgt tatccgctca    360
caattcccct atagtgagtc gtattaattt cgcgggatcg agatctcgat cctctacgcc    420
```

```
ggacgcatcg tggccggcat caccggcgcc acaggtgcgg ttgctggcgc ctatatcgcc      480
gacatcaccg atggggaaga tcgggctcgc cacttcgggc tcatgagcgc ttgtttcggc      540
gtgggtatgg tggcaggccc cgtggccggg ggactgttgg gcgccatctc cttgcatgca      600
ccattccttg cggcggcggt gctcaacggc ctcaacctac tactgggctg cttcctaatg      660
caggagtcgc ataagggaga gcgtcgagat cccggacacc atcgaatggc gcaaaacctt      720
tcgcggtatg gcatgatagc gcccggaaga gagtcaattc agggtggtga atgtgaaacc      780
agtaacgtta tacgatgtcg cagagtatgc cggtgtctct tatcagaccg tttcccgcgt      840
ggtgaaccag gccagccacg tttctgcgaa aacgcgggaa aaagtggaag cggcgatggc      900
ggagctgaat tacattccca accgcgtggc acaacaactg gcgggcaaac agtcgttgct      960
gattggcgtt gccacctcca gtctggccct gcacgcgccg tcgcaaattg tcgcggcgat     1020
taaatctcgc gccgatcaac tgggtgccag cgtggtggtg tcgatggtag aacgaagcgg     1080
cgtcgaagcc tgtaaagcgg cggtgcacaa tcttctcgcg caacgcgtca gtgggctgat     1140
cattaactat ccgctggatg accaggatgc cattgctgtg gaagctgcct gcactaatgt     1200
tccggcgtta tttcttgatg tctctgacca gacacccatc aacagtatta tttttctccca     1260
tgaagacggt acgcgactgg gcgtggagca tctggtcgca ttgggtcacc agcaaatcgc     1320
gctgttagcg ggcccattaa gttctgtctc ggcgcgtctg cgtctggctg gctggcataa     1380
atatctcact cgcaatcaaa ttcagccgat agcggaacgg gaaggcgact ggagtgccat     1440
gtccggtttt caacaaacca tgcaaatgct gaatgagggc atcgttccca ctgcgatgct     1500
ggttgccaac gatcagatgg cgctgggcgc aatgcgcgcc attaccgagt ccgggctgcg     1560
cgttggtgcg gatatctcgg tagtgggata cgacgatacc gaagacagct catgttatat     1620
cccgccgtta accaccatca acaggatttt cgcctgctg gggcaaaacca gcgtggaccg     1680
cttgctgcaa ctctctcagg gccaggcggt gaagggcaat cagctgttgc ccgtctcact     1740
ggtgaaaaga aaaaccaccc tggcgcccaa tacgcaaacc gcctctcccc gcgcgttggc     1800
cgattcatta atgcagctgg cacgacaggt ttcccgactg gaaagcgggc agtgagcgca     1860
acgcaattaa tgtaagttag ctcactcatt aggcaccggg atctcgaccg atgcccttga     1920
gagccttcaa cccagtcagc tccttccggt gggcgcgggg catgactatc gtcgccgcac     1980
ttatgactgt cttctttatc atgcaactcg taggacaggt gccggcagcg ctctgggtca     2040
ttttcggcga ggaccgcttt cgctggagcg cgacgatgat cggcctgtcg cttgcggtat     2100
tcggaatctt gcacgccctc gctcaagcct tcgtcactgg tcccgccacc aaacgtttcg     2160
gcgagaagca ggccattatc gccggcatgg cggccccacg ggtgcgcatg atcgtgctcc     2220
tgtcgttgag gacccggcta ggctggcggg gttgccttac tggttagcag aatgaatcac     2280
cgatacgcga gcgaacgtga agcgactgct gctgcaaaac gtctgcgacc tgagcaacaa     2340
catgaatggt cttcggtttc cgtgtttcgt aaagtctgga aacgcggaag tcagcgccct     2400
gcaccattat gttccggatc tgcatcgcag gatgctgctg ctaccctgt ggaacaccta     2460
catctgtatt aacgaagcgc tggcattgac cctgagtgat ttttctctgg tcccgccgca     2520
tccataccgc cagttgttta ccctcacaac gttccagtaa ccgggcatgt tcatcatcag     2580
taacccgtat cgtgagcatc ctctctcgtt tcatcggtat cattacccccc atgaacagaa     2640
atcccccctta cacggaggca tcagtgacca acaggaaaaa accgcccctt aacatggccc     2700
gctttatcag aagccagaca ttaacgcttc tggagaaact caacgagctg gacgcggatg     2760
aacaggcaga catctgtgaa tcgcttcacg accacgctga tgagctttac cgcagctgcc     2820
```

-continued

```
tcgcgcgttt cggtgatgac ggtgaaaacc tctgacacat gcagctcccg gagacggtca    2880
cagcttgtct gtaagcggat gccgggagca gacaagcccg tcaggcgcg tcagcgggtg     2940 ttggcgggtg tcgggcgca gccatgaccc agtcacgtag cgatagcgga gtgtatactg     3000
gcttaactat gcggcatcag agcagattgt actgagagtg caccatatat gcggtgtgaa    3060
ataccgcaca gatgcgtaag gagaaaatac cgcatcaggc gctcttccgc ttcctcgctc    3120
actgactcgc tgcgctcggt cgttcggctg cggcgagcgg tatcagctca ctcaaaggcg    3180
gtaatacggt tatccacaga atcaggggat aacgcaggaa agaacatgtg agcaaaaggc    3240
cagcaaaagg ccaggaaccg taaaaaggcc gcgttgctgg cgtttttcca taggctccgc    3300
ccccctgacg agcatcacaa aaatcgacgc tcaagtcaga ggtggcgaaa cccgacagga    3360
ctataaagat accaggcgtt tccccctgga agctccctcg tgcgctctcc tgttccgacc    3420
ctgccgctta ccggatacct gtccgccttt ctcccttcgg gaagcgtggc gctttctcat    3480
agctcacgct gtaggtatct cagttcggtg taggtcgttc gctccaagct gggctgtgtg    3540 cacgaaccccc ccgttcagcc cgaccgctgc gccttatccg gtaactatcg tcttgagtcc    3600
aacccggtaa gacacgactt atcgccactg gcagcagcca ctggtaacag gattagcaga    3660
gcgaggtatg taggcggtgc tacagagttc ttgaagtggt ggcctaacta cggctacact    3720
agaaggacag tatttggtat ctgcgctctg ctgaagccag ttaccttcgg aaaaagagtt    3780
ggtagctctt gatccggcaa acaaaccacc gctggtagcg tggtttttt tgtttgcaag    3840 cagcagatta cgcgcagaaa aaaggatct caagaagatc ctttgatctt ttctacgggg    3900
tctgacgctc agtggaacga aaactcacgt taagggattt tggtcatgaa caataaaact    3960
gtctgcttac ataaacagta atacaagggg tgttatgagc catattcaac gggaaacgtc    4020
ttgctctagg ccgcgattaa attccaacat ggatgctgat ttatatgggt ataaatgggc    4080
tcgcgataat gtcgggcaat caggtgcgac aatctatcga ttgtatggga agcccgatgc    4140
gccagagttg tttctgaaac atggcaaagg tagcgttgcc aatgatgtta cagatgagat    4200
ggtcagacta aactggctga cggaatttat gcctcttccg accatcaagc attttatccg    4260
tactcctgat gatgcatggt tactcaccac tgcgatcccc gggaaaacag cattccaggt    4320
attagaagaa tatcctgatt caggtgaaaa tattgttgat gcgctggcag tgttcctgcg    4380
ccggttgcat cgattcctg tttgtaattg tccttttaac agcgatcgcg tatttcgtct    4440
cgctcaggcg caatcacgaa tgaataacgg tttggttgat gcgagtgatt ttgatgacga    4500
gcgtaatggc tggcctgttg aacaagtctg gaaagaaatg cataaacttt tgccattctc    4560
accggattca gtcgtcactc atggtgattt ctcacttgat aaccttattt ttgacgaggg    4620
gaaattaata ggttgtattg atgttggacg agtcggaatc gcagaccgat accaggatct    4680
tgccatccta tggaactgcc tcggtgagtt ttctccttca ttacagaaac ggcttttca    4740 aaaatatggt attgataatc ctgatatgaa taaattgcag tttcatttga tgctcgatga    4800 gttttctaa gaattaattc atgagcggat acatatttga atgtatttag aaaaataaac    4860
aaataggggt tccgcgcaca tttccccgaa aagtgccacc taaattgtaa gcgttaatat    4920
tttgttaaaa ttcgcgttaa attttgtta aatcagctca ttttttaacc aataggccga    4980
aatcggcaaa atcccttata aatcaaaaga atagaccgag atagggttga gtgttgttcc    5040
agtttggaac aagagtccac tattaaagaa cgtggactcc aacgtcaaag ggcgaaaaac    5100
cgtctatcag ggcgatggcc cactacgtga accatcaccc taatcaagtt ttttggggtc    5160
gaggtgccgt aaagcactaa atcggaaccc taaagggagc ccccgattta gagcttgacg    5220
```

-continued

```
gggaaagccg gcgaacgtgg cgagaaagga agggaagaaa gcgaaaggag cgggcgctag    5280
ggcgctggca agtgtagcgg tcacgctgcg cgtaaccacc acacccgccg cgcttaatgc    5340
gccgctacag ggcgcgtccc attcgcca                                        5368
```

<210> SEQ ID NO 7
<211> LENGTH: 721
<212> TYPE: PRT
<213> ORGANISM: Solanum lycopersicum

<400> SEQUENCE: 7

Met Ala Ser Ser Ile Val Gln Asn Gly His Val Asn Gly Glu Ala Met
1               5                   10                  15

Asp Leu Cys Lys Lys Ser Ile Asn Val Asn Asp Pro Leu Asn Trp Glu
            20                  25                  30

Met Ala Ala Glu Ser Leu Arg Gly Ser His Leu Asp Glu Val Lys Lys
        35                  40                  45

Met Val Asp Glu Phe Arg Lys Pro Ile Val Lys Leu Gly Gly Glu Thr
    50                  55                  60

Leu Thr Val Ala Gln Val Ala Ser Ile Ala Asn Val Asp Asn Lys Ser
65                  70                  75                  80

Asn Gly Val Lys Val Glu Leu Ser Glu Ser Ala Arg Ala Gly Val Lys
                85                  90                  95

Ala Ser Ser Asp Trp Val Met Asp Ser Met Gly Lys Gly Thr Asp Ser
            100                 105                 110

Tyr Gly Val Thr Thr Gly Phe Gly Ala Thr Ser His Arg Arg Thr Lys
        115                 120                 125

Asn Gly Gly Ala Leu Gln Lys Glu Leu Ile Arg Phe Leu Asn Ala Gly
    130                 135                 140

Val Phe Gly Asn Gly Thr Glu Ser Ser His Thr Leu Pro His Ser Ala
145                 150                 155                 160

Thr Arg Ala Ala Met Leu Val Arg Ile Asn Thr Leu Leu Gln Gly Tyr
                165                 170                 175

Ser Gly Ile Arg Phe Glu Ile Leu Glu Ala Ile Thr Lys Leu Ile Asn
            180                 185                 190

Ser Asn Ile Thr Pro Cys Leu Pro Leu Arg Gly Thr Ile Thr Ala Ser
        195                 200                 205

Gly Asp Leu Val Pro Leu Ser Tyr Ile Ala Gly Leu Leu Thr Gly Arg
    210                 215                 220

Pro Asn Ser Lys Ala Val Gly Pro Asn Gly Glu Lys Leu Asn Ala Glu
225                 230                 235                 240

Glu Ala Phe Arg Val Ala Gly Val Thr Ser Gly Phe Phe Glu Leu Gln
                245                 250                 255

Pro Lys Glu Gly Leu Ala Leu Val Asn Gly Thr Ala Val Gly Ser Gly
            260                 265                 270

Met Ala Ser Met Val Leu Phe Glu Ser Asn Ile Leu Ala Val Met Ser
        275                 280                 285

Glu Val Leu Ser Ala Ile Phe Ala Glu Val Met Asn Gly Lys Pro Glu
    290                 295                 300

Phe Thr Asp Tyr Leu Thr His Lys Leu Lys His His Pro Gly Gln Ile
305                 310                 315                 320

Glu Ala Ala Ala Ile Met Glu His Ile Leu Asp Gly Ser Ser Tyr Val
                325                 330                 335

```
Lys Ala Ala Gln Lys Leu His Glu Met Asp Pro Leu Gln Lys Pro Lys
                340                 345                 350
Gln Asp Arg Tyr Ala Leu Arg Thr Ser Pro Gln Trp Leu Gly Pro Gln
            355                 360                 365
Ile Glu Val Ile Arg Ala Ala Thr Lys Met Ile Glu Arg Glu Ile Asn
        370                 375                 380
Ser Val Asn Asp Asn Pro Leu Ile Asp Val Ser Arg Asn Lys Ala Leu
385                 390                 395                 400
His Gly Gly Asn Phe Gln Gly Thr Pro Ile Gly Val Ser Met Asp Asn
                405                 410                 415
Thr Arg Leu Ala Leu Ala Ser Ile Gly Lys Leu Met Phe Ala Gln Phe
            420                 425                 430
Ser Glu Leu Val Asn Asp Tyr Tyr Asn Asn Gly Leu Pro Ser Asn Leu
        435                 440                 445
Thr Ala Gly Arg Asn Pro Ser Leu Asp Tyr Gly Leu Lys Gly Ala Glu
450                 455                 460
Ile Ala Met Ala Ser Tyr Cys Ser Glu Leu Gln Phe Leu Ala Asn Pro
465                 470                 475                 480
Val Thr Asn His Val Gln Ser Ala Glu Gln His Asn Gln Asp Val Asn
                485                 490                 495
Ser Leu Gly Leu Ile Ser Ala Arg Lys Thr Ala Glu Ala Val Asp Ile
            500                 505                 510
Leu Lys Leu Met Ser Ser Thr Tyr Leu Val Ala Leu Cys Gln Ala Ile
        515                 520                 525
Asp Leu Arg His Leu Glu Glu Asn Leu Arg Ser Ala Val Lys Asn Thr
530                 535                 540
Val Ser Gln Val Ala Lys Arg Thr Leu Thr Met Gly Ala Asn Gly Glu
545                 550                 555                 560
Leu His Pro Ala Arg Phe Cys Glu Lys Glu Leu Leu Arg Val Val Asp
                565                 570                 575
Arg Glu Tyr Val Phe Ala Tyr Ala Asp Asp Pro Cys Ser Ser Thr Tyr
            580                 585                 590
Pro Leu Met Gln Lys Leu Arg Gln Val Leu Val Asp His Ala Met Lys
        595                 600                 605
Asn Gly Glu Ser Glu Lys Asn Val Asn Ser Ser Ile Phe Gln Lys Ile
610                 615                 620
Val Ala Phe Glu Asp Glu Leu Lys Ala Val Leu Pro Lys Glu Val Glu
625                 630                 635                 640
Ser Ala Arg Ala Val Val Glu Ser Gly Asn Pro Ala Ile Pro Asn Arg
                645                 650                 655
Ile Thr Glu Cys Arg Ser Tyr Pro Leu Tyr Arg Leu Val Arg Gln Glu
            660                 665                 670
Leu Gly Ser Glu Leu Leu Thr Gly Glu Lys Val Arg Ser Pro Gly Glu
        675                 680                 685
Glu Ile Asp Lys Val Phe Thr Ala Met Cys Asn Gly Gln Ile Ile Asp
690                 695                 700
Pro Leu Leu Glu Cys Leu Lys Ser Trp Asn Gly Ala Pro Leu Pro Ile
705                 710                 715                 720
Cys

<210> SEQ ID NO 8
<211> LENGTH: 1101
<212> TYPE: DNA
<213> ORGANISM: Thermoactinomyces intermedius
```

<400> SEQUENCE: 8

```
atgcgcgacg tgtttgaaat gatggaccgc tatggccacg agcaggtcat tttttgccgt      60
catccgcaaa ccggtctcaa agcgatcatc gccttgcata atacaaccgc ggggccggct     120
ttgggtggat gccgcatgat cccgtatgct tcgacggacg aagccttgga ggatgttttg     180
cggttgtcca aaggcatgac ctataaatgc agtctggcgg atgtggactt tggcggggga     240
aaaatggtta tcatcggcga tccgaaaaaa gataaatcgc cggagttgtt tcgcgtgatc     300
ggccgttttg tgggcgggtt aaacggccgt ttctataccg gaaccgacat gggaaccaat     360
ccggaagatt ttgtccatgc cgccagggaa tcgaaatctt ttgccggatt gccgaaatcg     420
tacgcggaa  aggggacac  atccattccc  accgcgctcg  gggtgtttca  cggaatgcgg   480
gccaccgccc ggtttttatg ggggacggat cagctgaaag gcgtgtggt  tgccatccaa    540
ggagtcggca aggtgggaga cgcttgttg  cagcttttgg tcgaagtggg ggcttactgc     600
aaaattgccg acatcgattc ggtgcgatgc gaacagctga agaaaagta  tggcgacaag     660
gtccaattgg tggatgtgaa ccggattcac aaggagagtt gcgatatttt ctcgccttgc     720
gccaaaggcg gcgtggtcaa tgatgacacc attgacgagt ccgttgcct  ggccattgtc    780
ggatccgcca caaccaact  ggtggaagac cggcatgggg cactgcttca aaaacggagc     840
atttgttatg caccgatta  tctggtgaat gccggcgggc tgattcaagt ggctgatgaa     900
ctggaaggct tccatgaaga gagtgctc  gccaaaaccg aagcgattta tgacatggtc      960
ctggatattt ttcaccgggc gaaaaatgag aatattacca cttgtgaggc agcggaccgg    1020
atcgtgatgg agcgtttgaa aaagttaacc gatattcgcc ggatcttgtt ggaggatccc    1080
cgcaacagcg caaggaggta a                                              1101
```

<210> SEQ ID NO 9
<211> LENGTH: 352
<212> TYPE: PRT
<213> ORGANISM: Caenorhabditis remanei

<400> SEQUENCE: 9

```
Met Asp Phe Lys Ala Lys Leu Leu Ala Glu Met Ala Lys Lys Arg Lys
1               5                   10                  15

Ala Val Ser Gly Leu Glu Val Lys Glu Gly Gly Ala Lys Phe Val Arg
            20                  25                  30

Gly Ala Asp Leu Glu Ser Lys Arg Thr Gln Glu Tyr Glu Ala Lys Gln
        35                  40                  45

Glu Glu Leu Ala Ile Lys Lys Arg Lys Ala Asp Asp Glu Ile Leu Gln
    50                  55                  60

Glu Ser Thr Ser Arg Ala Lys Ile Val Pro Glu Val Pro Glu Ala Glu
65                  70                  75                  80

Phe Asp Glu Lys Thr Pro Met Pro Glu Ile His Ala Arg Leu Arg Gln
                85                  90                  95

Arg Gly Gln Pro Ile Leu Leu Phe Gly Glu Ser Glu Leu Ser Val Arg
            100                 105                 110

Lys Arg Leu His Gln Leu Glu Ile Glu Gln Pro Glu Leu Asn Glu Gly
        115                 120                 125

Trp Glu Asn Glu Met Gln Thr Ala Met Lys Phe Ile Gly Lys Glu Met
    130                 135                 140

Asp Lys Ala Val Val Glu Gly Thr Ala Asp Ser Ala Thr Arg His Asp
145                 150                 155                 160
```

```
Ile Ala Leu Pro Gln Gly Tyr Glu Glu Asp Asn Trp Lys Ser Ile Glu
            165                 170                 175

His Ala Ser Thr Leu Leu Gly Val Gly Asp Glu Met Lys Arg Asp Cys
        180                 185                 190

Asp Ile Ile Leu Ser Ile Cys Arg Tyr Ile Leu Ala Arg Trp Ala Arg
            195                 200                 205

Asp Leu Asn Asp Arg Pro Leu Asp Val Lys Lys Thr Ala Gln Gly Met
    210                 215                 220

His Glu Ala Ala His His Lys Gln Thr Thr Met His Leu Lys Ser Leu
225                 230                 235                 240

Met Thr Ser Met Glu Lys Tyr Asn Val Asn Asn Asp Ile Arg His His
            245                 250                 255

Leu Ala Lys Ile Cys Arg Leu Leu Val Ile Glu Arg Asn Tyr Leu Glu
        260                 265                 270

Ala Asn Asn Ala Tyr Met Glu Met Ala Ile Gly Asn Ala Pro Trp Pro
    275                 280                 285

Val Gly Val Thr Arg Ser Gly Ile His Gln Arg Pro Gly Ser Ala Lys
        290                 295                 300

Ala Tyr Val Ser Asn Ile Ala His Val Leu Asn Asp Glu Thr Gln Arg
305                 310                 315                 320

Lys Tyr Ile Gln Ala Phe Lys Arg Leu Met Thr Lys Leu Gln Glu Tyr
            325                 330                 335

Phe Pro Thr Asp Pro Ser Lys Ser Val Glu Phe Val Lys Lys Ser Val
        340                 345                 350

<210> SEQ ID NO 10
<211> LENGTH: 411
<212> TYPE: PRT
<213> ORGANISM: Arabidopsis thaliana

<400> SEQUENCE: 10

Met Asn Ala Leu Ala Ala Thr Asn Arg Asn Phe Lys Leu Ala Ala Arg
1               5                   10                  15

Leu Leu Gly Leu Asp Ser Lys Leu Glu Lys Ser Leu Leu Ile Pro Phe
            20                  25                  30

Arg Glu Ile Lys Val Glu Cys Thr Ile Pro Lys Asp Asp Gly Thr Leu
        35                  40                  45

Ala Ser Phe Val Gly Phe Arg Val Gln His Asp Asn Ala Arg Gly Pro
    50                  55                  60

Met Lys Gly Gly Ile Arg Tyr His Pro Glu Val Asp Pro Asp Glu Val
65                  70                  75                  80

Asn Ala Leu Ala Gln Leu Met Thr Trp Lys Thr Ala Val Ala Lys Ile
            85                  90                  95

Pro Tyr Gly Gly Ala Lys Gly Gly Ile Gly Cys Asp Pro Ser Lys Leu
        100                 105                 110

Ser Ile Ser Glu Leu Glu Arg Leu Thr Arg Val Phe Thr Gln Lys Ile
    115                 120                 125

His Asp Leu Ile Gly Ile His Thr Asp Val Pro Ala Pro Asp Met Gly
    130                 135                 140

Thr Gly Pro Gln Thr Met Ala Trp Ile Leu Asp Glu Tyr Ser Lys Phe
145                 150                 155                 160

His Gly Tyr Ser Pro Ala Val Val Thr Gly Lys Pro Ile Asp Leu Gly
            165                 170                 175

Gly Ser Leu Gly Arg Asp Ala Ala Thr Gly Arg Gly Val Met Phe Gly
        180                 185                 190
```

```
                                -continued

Thr Glu Ala Leu Leu Asn Glu His Gly Lys Thr Ile Ser Gly Gln Arg
        195                 200                 205

Phe Val Ile Gln Gly Phe Gly Asn Val Gly Ser Trp Ala Ala Lys Leu
        210                 215                 220

Ile Ser Glu Lys Gly Gly Lys Ile Val Ala Val Ser Asp Ile Thr Gly
225                 230                 235                 240

Ala Ile Lys Asn Lys Asp Gly Ile Asp Ile Pro Ala Leu Leu Lys His
                245                 250                 255

Thr Lys Glu His Arg Gly Val Lys Gly Phe Asp Gly Ala Asp Pro Ile
                260                 265                 270

Asp Pro Asn Ser Ile Leu Val Glu Asp Cys Asp Ile Leu Val Pro Ala
                275                 280                 285

Ala Leu Gly Gly Val Ile Asn Arg Glu Asn Ala Asn Glu Ile Lys Ala
        290                 295                 300

Lys Phe Ile Ile Glu Ala Ala Asn His Pro Thr Asp Pro Asp Ala Asp
305                 310                 315                 320

Glu Ile Leu Ser Lys Lys Gly Val Val Ile Leu Pro Asp Ile Tyr Ala
                325                 330                 335

Asn Ser Gly Gly Val Thr Val Ser Tyr Phe Glu Trp Val Gln Asn Ile
                340                 345                 350

Gln Gly Phe Met Trp Glu Glu Glu Lys Val Asn Asp Glu Leu Lys Thr
                355                 360                 365

Tyr Met Thr Arg Ser Phe Lys Asp Leu Lys Glu Met Cys Lys Thr His
        370                 375                 380

Ser Cys Asp Leu Arg Met Gly Ala Phe Thr Leu Gly Val Asn Arg Val
385                 390                 395                 400

Ala Gln Ala Thr Ile Leu Arg Gly Trp Gly Ala
                405                 410
```